(12) United States Patent  
Courtney et al.

(10) Patent No.: US 8,784,321 B2  
(45) Date of Patent: *Jul. 22, 2014

(54) IMAGING PROBE WITH COMBINED ULTRASOUND AND OPTICAL MEANS OF IMAGING

(75) Inventors: Brian Courtney, Toronto (CA); Nigel Robert Munce, Toronto (CA); Amandeep Singh Thind, Toronto (CA); Victor Xiao Dong Yang, Toronto (CA); Francis Stuart Foster, Toronto (CA)

(73) Assignee: Sunnybrook Health Sciences Centre, Toronto (CA)

( * ) Notice: Subject to any disclaimer, the term of this patent is extended or adjusted under 35 U.S.C. 154(b) by 1045 days.

This patent is subject to a terminal disclaimer.

(21) Appl. No.: 12/010,208

(22) Filed: Jan. 22, 2008

(65) Prior Publication Data

US 2008/0177183 A1 Jul. 24, 2008

Related U.S. Application Data

(60) Provisional application No. 60/881,169, filed on Jan. 19, 2007.

(51) Int. Cl.
*A61B 5/05* (2006.01)

(52) U.S. Cl.
USPC ........... 600/463; 600/109; 600/137; 600/407; 600/459; 600/462

(58) Field of Classification Search
USPC ......... 600/137, 160, 178, 459, 462–463, 466, 600/407, 476, 478, 427, 473
See application file for complete search history.

(56) References Cited

U.S. PATENT DOCUMENTS

| | | | |
|---|---|---|---|
| 4,697,577 A | 10/1987 | Forkner | |
| 4,794,931 A | 1/1989 | Yock | |
| 4,869,258 A | 9/1989 | Hetz | |
| 4,895,158 A | 1/1990 | Kawabuchi et al. | |
| 4,951,677 A | 8/1990 | Crowley | |
| 4,972,839 A | 11/1990 | Angelsen | |

(Continued)

FOREIGN PATENT DOCUMENTS

| | | |
|---|---|---|
| EP | 1972262 | 9/2008 |
| JP | 11-056752 | 2/1999 |

(Continued)

OTHER PUBLICATIONS

Brezinski et al, "Assessing atherosclerotic plaque morphology: comparison of optical coherence tomography and high frequency intravascular ultrasound", BMJ Heart, May 1997, p. 397-403, vol. 77(5), http://80-gatewayl.ovid.com.lane-proxy.stanford.org/ovidweb.cgi 12 pages.

(Continued)

*Primary Examiner* — Unsu Jung  
*Assistant Examiner* — Daniel Huntley  
(74) *Attorney, Agent, or Firm* — Hill & Schumacher

(57) ABSTRACT

The present invention provides an imaging probe for imaging mammalian tissues and structures using high resolution imaging, including high frequency ultrasound and optical coherence tomography. The imaging probes structures using high resolution imaging use combined high frequency ultrasound (IVUS) and optical imaging methods such as optical coherence tomography (OCT) and to accurate co-registering of images obtained from ultrasound image signals and optical image, signals during scanning a region of interest.

52 Claims, 28 Drawing Sheets

(56) References Cited

U.S. PATENT DOCUMENTS

| | | | |
|---|---|---|---|
| 5,152,293 | A | 10/1992 | Vonesh et al. |
| 5,373,845 | A | 12/1994 | Gardineer |
| 5,373,849 | A | 12/1994 | Maroney |
| 5,375,602 | A | 12/1994 | Lancee |
| 5,379,772 | A | 1/1995 | Imran |
| 5,427,107 | A | 6/1995 | Milo |
| 5,429,136 | A | 7/1995 | Milo |
| 5,465,724 | A | 11/1995 | Sliwa, Jr. et al. |
| 5,469,853 | A | 11/1995 | Law et al. |
| 5,485,845 | A | 1/1996 | Verdonk |
| 5,505,088 | A | 4/1996 | Chandraratna et al. |
| 5,606,975 | A | 3/1997 | Liang |
| 5,647,367 | A | 7/1997 | Lum et al. |
| 5,651,366 | A | 7/1997 | Liang |
| 5,682,895 | A | 11/1997 | Ishiguro |
| 5,718,231 | A | 2/1998 | Dewhurst |
| 5,779,643 | A | 7/1998 | Lum et al. |
| 5,817,021 | A | 10/1998 | Reichenberger |
| 5,916,210 | A | 6/1999 | Winston |
| 6,035,229 | A | 3/2000 | Silverstein |
| 6,110,121 | A | 8/2000 | Lenker |
| 6,134,003 | A | 10/2000 | Tearney |
| 6,171,247 | B1 | 1/2001 | Seward et al. |
| 6,178,346 | B1 | 1/2001 | Amundson |
| 6,200,268 | B1 | 3/2001 | Vince |
| 6,264,610 | B1 | 7/2001 | Zhu |
| 6,315,732 | B1 | 11/2001 | Suorsa |
| 6,390,978 | B1 | 5/2002 | Irion et al. |
| 6,445,939 | B1 | 9/2002 | Swanson et al. |
| 6,450,964 | B1 | 9/2002 | Webler |
| 6,485,413 | B1 | 11/2002 | Boppart |
| 6,546,272 | B1 * | 4/2003 | MacKinnon et al. ......... 600/407 |
| 6,583,914 | B1 | 6/2003 | Muller et al. |
| 6,592,526 | B1 | 7/2003 | Lenker |
| 6,626,834 | B2 | 9/2003 | Dunne et al. |
| 6,690,958 | B1 | 2/2004 | Walker et al. |
| 6,949,072 | B2 | 9/2005 | Furnish et al. ............... 600/466 |
| 6,975,898 | B2 | 12/2005 | Seibel |
| 7,077,808 | B2 | 7/2006 | Couvillon |
| 7,289,842 | B2 | 10/2007 | Maschke |
| 7,366,376 | B2 | 4/2008 | Shishkov et al. |
| 7,761,139 | B2 | 7/2010 | Tearney et al. |
| 7,935,060 | B2 | 5/2011 | Schmitt et al. |
| 2003/0023019 | A1 | 1/2003 | Kondou |
| 2005/0020926 | A1 | 1/2005 | Wiklof |
| 2005/0075574 | A1 | 4/2005 | Furnish et al. |
| 2005/0101859 | A1 * | 5/2005 | Maschke ....................... 600/427 |
| 2006/0058614 | A1 | 3/2006 | Tsujita |
| 2006/0116571 | A1 | 6/2006 | Maschke |
| 2006/0287595 | A1 | 12/2006 | Maschke |
| 2007/0016062 | A1 | 1/2007 | Park |
| 2007/0161893 | A1 | 7/2007 | Milner |
| 2007/0282197 | A1 | 12/2007 | Bill et al. |
| 2008/0287810 | A1 * | 11/2008 | Park et al. ..................... 600/478 |
| 2009/0088648 | A1 | 4/2009 | Jaffe et al. |
| 2009/0203991 | A1 | 8/2009 | Papaioannou et al. |

FOREIGN PATENT DOCUMENTS

| | | |
|---|---|---|
| JP | 11056786 | 2/1999 |
| JP | 2004209268 | 7/2004 |
| JP | 2004290548 | 10/2004 |
| JP | 2005224399 | 8/2005 |
| JP | 2008-142454 | 6/2008 |
| WO | 9616600 | 6/1996 |
| WO | 9732182 | 9/1997 |
| WO | 0033120 | 6/2000 |
| WO | 03/067526 | 8/2003 |
| WO | 2004/010856 | 2/2004 |
| WO | 2004/096049 | 11/2004 |
| WO | 2006/121851 | 11/2006 |
| WO | 2007123518 | 11/2007 |
| WO | 2008057573 | 5/2008 |

OTHER PUBLICATIONS

Nair et al, "Coronary Plaque Classification With Intravascular Ultrasound Radiofrequency Data Analysis", Circulation, 2002;106:2200-2206.

Funovics et al, "Catheter-based in Vivo Imaging of Enzyme Activity and Gene Expression: Feasibility Study in Mice", Radiology, 2004; 231:659-666.

Picano et al, "Angle dependence of ultrasonic backscatter in arterial tissues: a study in vitro", Circulation 1985; 72; pp. 572-576.

Kubo et al, "Assessment of Culprit Lesion Morphology in Acute Myocardial Infarction", J Amer Col Cardiology, vol. 50, No. 10, 2007, pp. 933-939.

Motz et al, "In vivo Raman spectral pathology of human atherosclerosis and vulneravle plaque", J. Bio Optics, 11(2), 021003, Mar./Ap 2005, 9 pages.

Mao et al, "Graded-index fiber lens proposed for ultrasmall probes used in biomedical imaging", Applied Optics, vol. 46, No. 23, Aug. 10, 2007, pp. 5887-5894.

Klingensmith et al, "Evaluation of Three-Dimensional Segmentation Algorithms for the Identification of Luminal and Medial-Adventitial Borders in Intravascular Ultrasound Images", IEEE Transactions on Medical Imaging, vol. 19, No. 10, Oct. 2000, pp. 996-1011.

Goretz et al, "Contrast Harmonic Intravascular Ultrasound, A Feasibility Study for Vasa Vasorum Imaging", Investigative Radiology, vol. 41, No. 8, Aug. 2006, pp. 631-638.

De Korte et al, "Identification of Atherosclerotic Plaque Components With Intravascular Ultrasound Elastography in Vivo: A Yucatan Pig Study", Circulation, 2002; 105; 1627-1630.

Daniels et al, "Sonoluminescence in Water and Agar Gels During Irradiation With 0.75 MHz Continuous-Wave Ultrasound", Ultrasound in Med. & Biol. vol. 17, No. 3. pp. 297-308, 1991.

Kawasaki et al, "Diagnostic Accuracy of Optical Coherence Tomography and Integrated Backscatter Intravascular Ultrasound Images for Tissue Characterization of Human Coronary Plaques", J. Amer. Col. Cardiology, vol. 48, No. 1, 2006, pp. 81-88.

Courtney et al, "Effects of Transducer Position on Backscattered Intensity in Coronary Arteries", Ultrasound in Med. Biol, vol. 28, No. 1, pp. 81-91, 2002.

Hoff, Harm ten. "Scannings mechanisms for intravascular ultrasound imaging: a flexible approach" Diss. Erasmus University, Rotterdam. 1993. Print: 117-151, 195-199.

Caplan JD et al, "Near-infrared spectroscopy for the detection of vulnerable coronary artery plaques". J Am Coll Cardiol. Apr. 18, 2006:47(8Suppl):C92-C96.

Extended European Search Report (Appl. No. 0870623T8—1660/2111165 PCT/CA2008000089) dated Sep. 9, 2013.

* cited by examiner

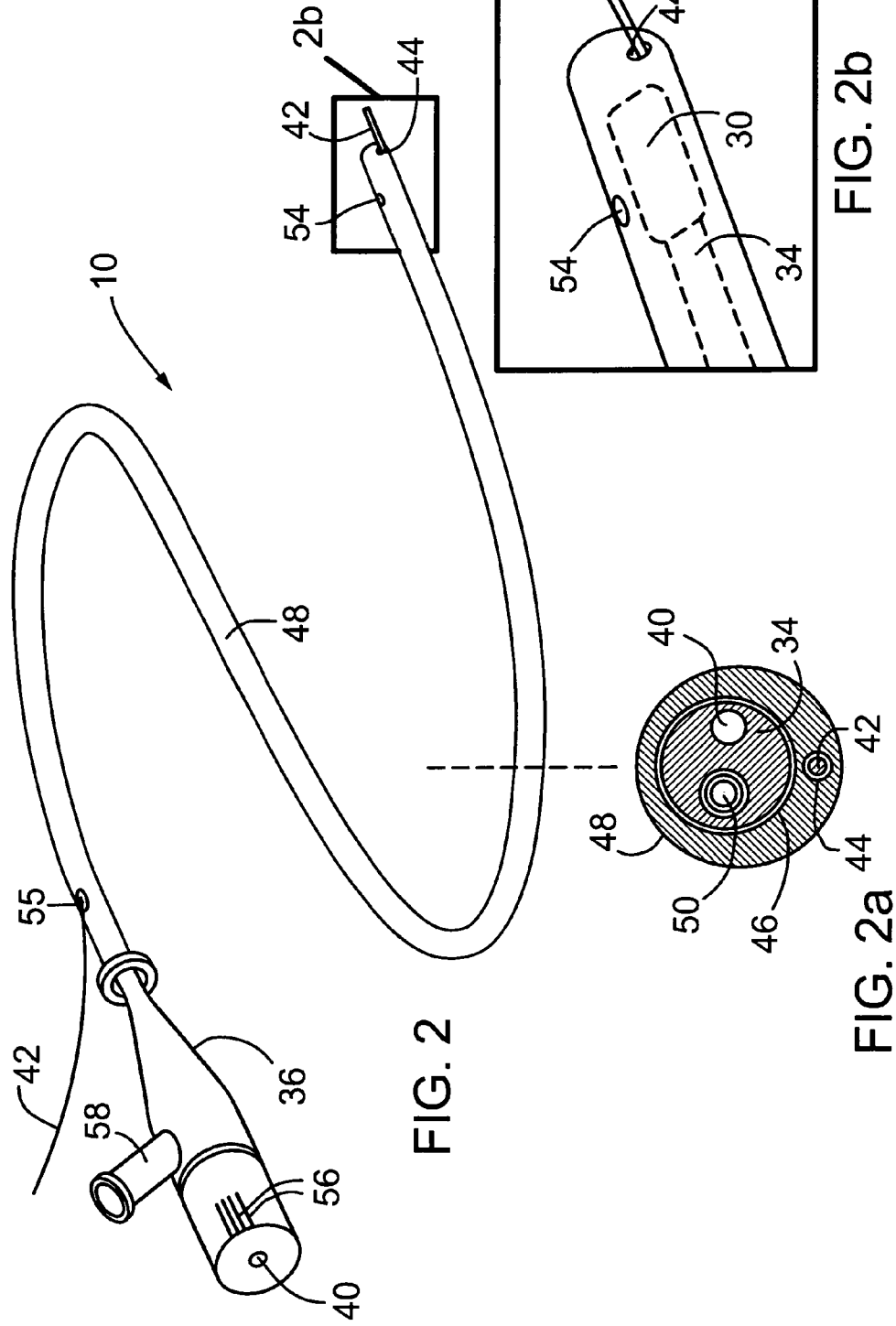

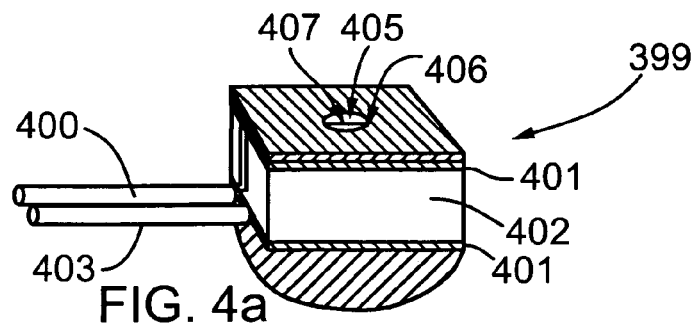
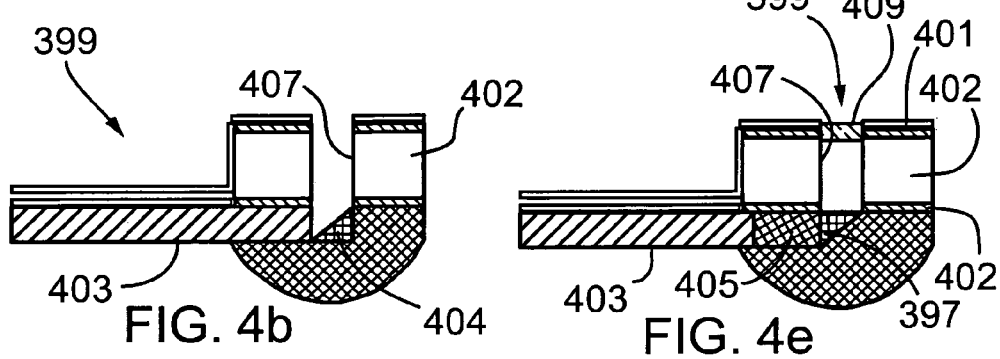
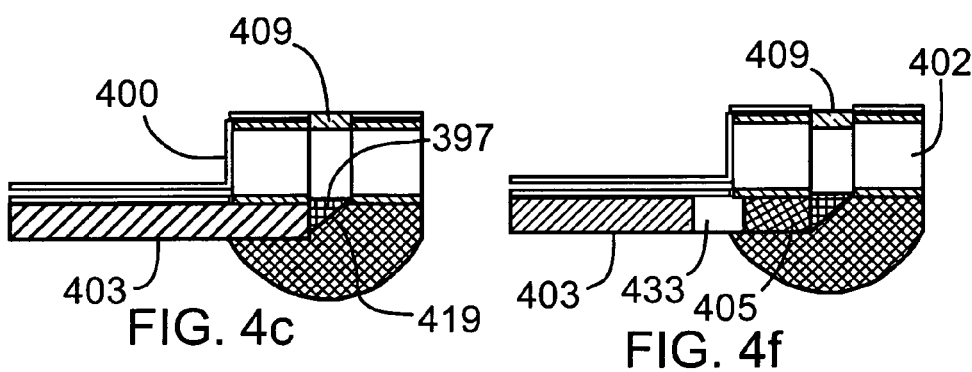
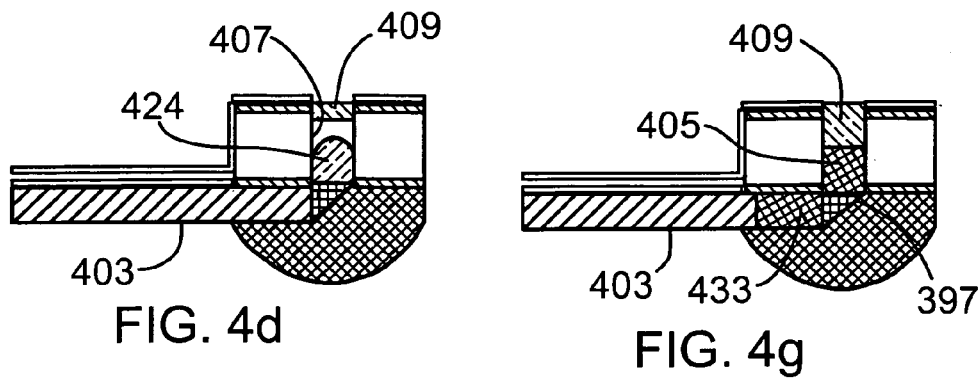

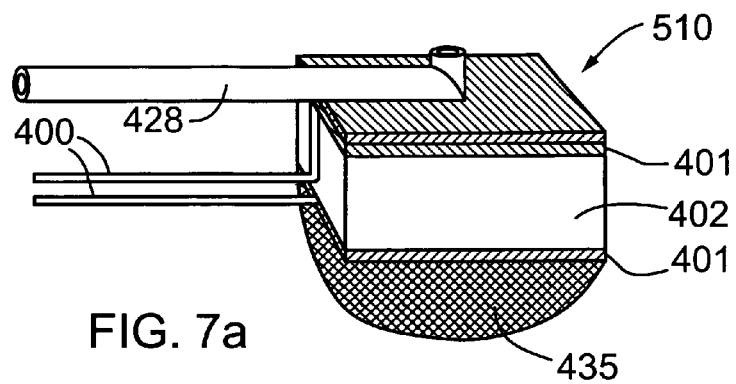
FIG. 7a
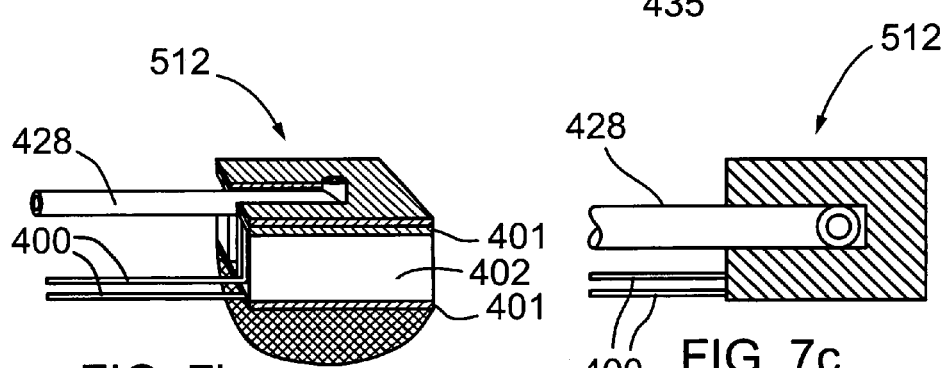
FIG. 7b
FIG. 7c
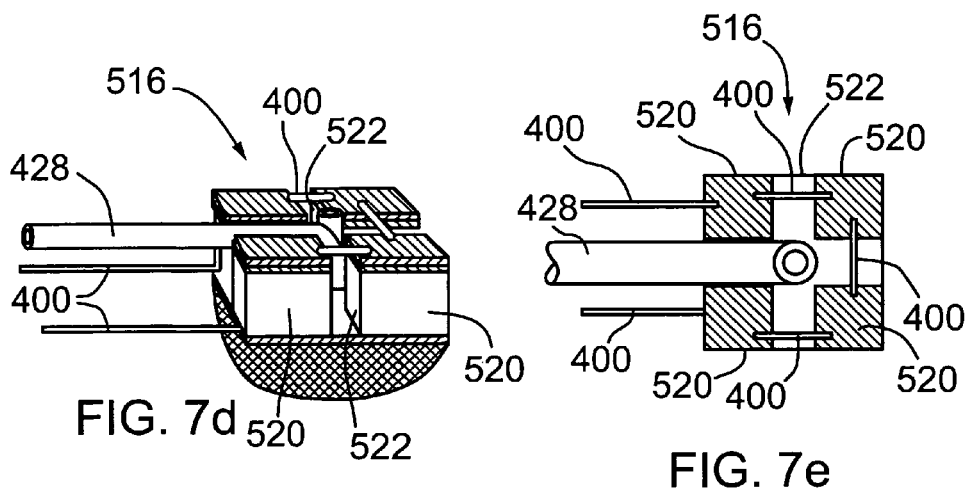
FIG. 7d
FIG. 7e

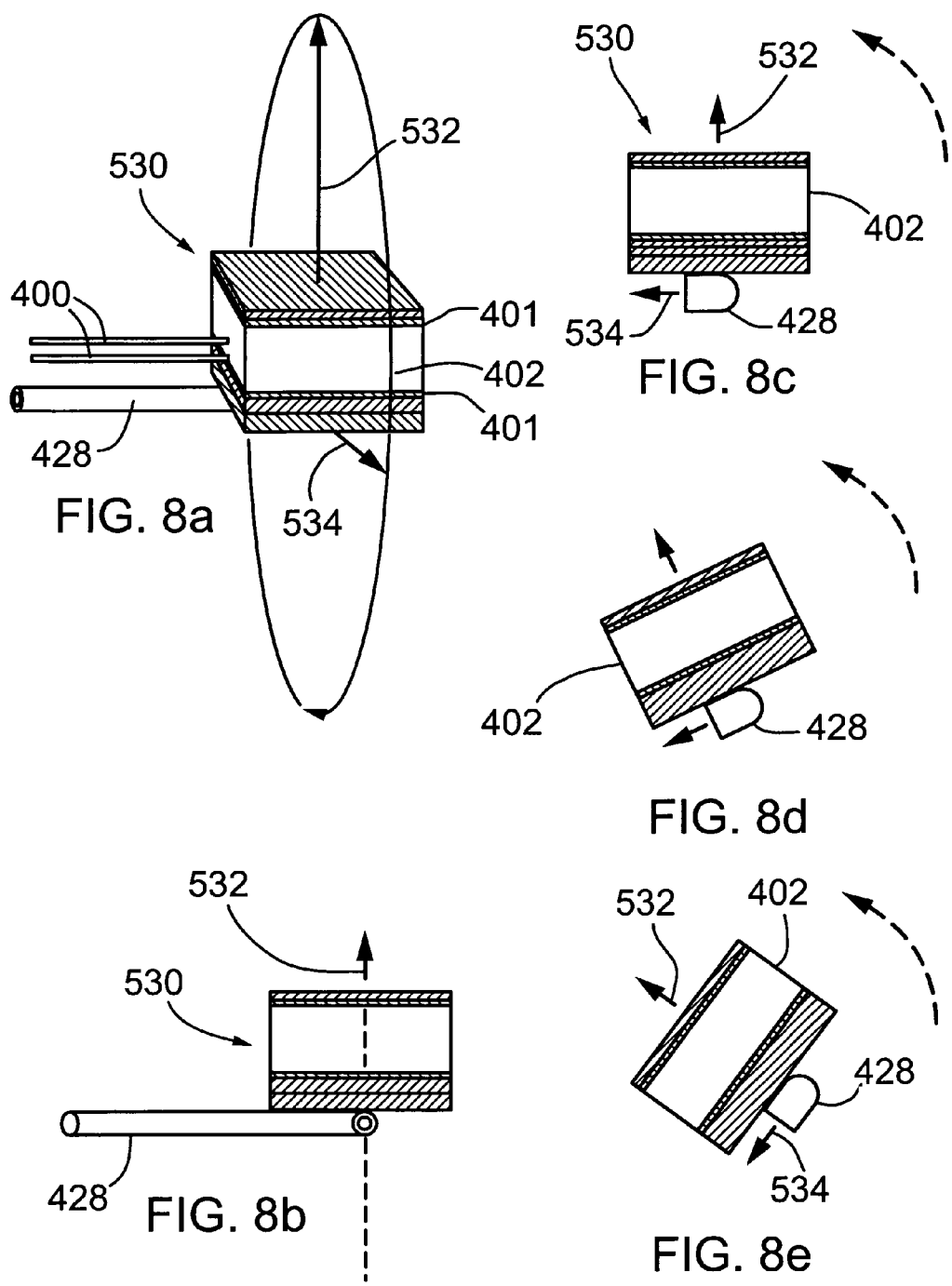

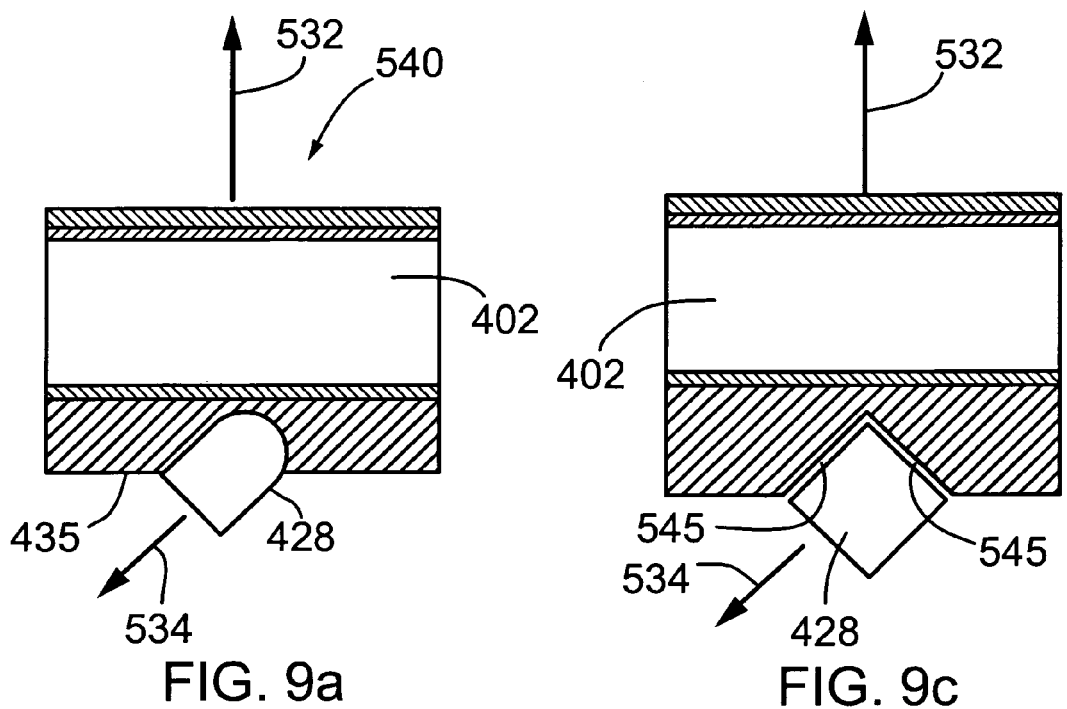
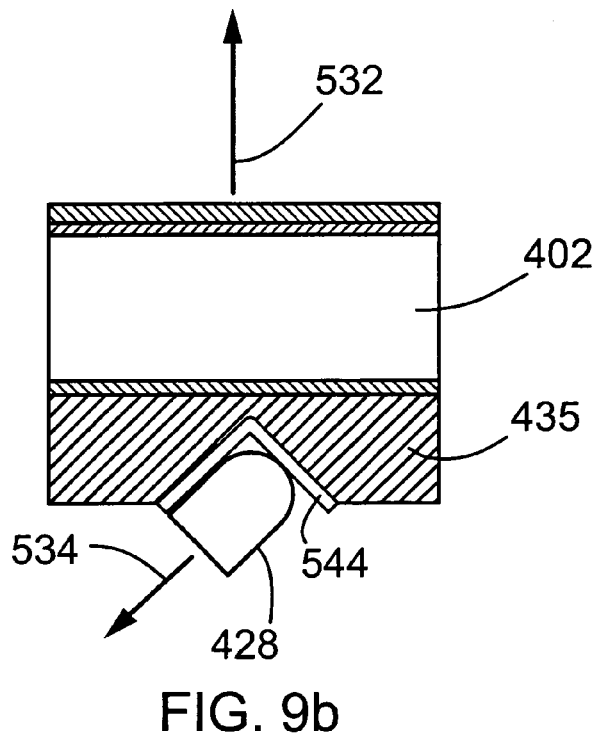
FIG. 9a
FIG. 9c
FIG. 9b

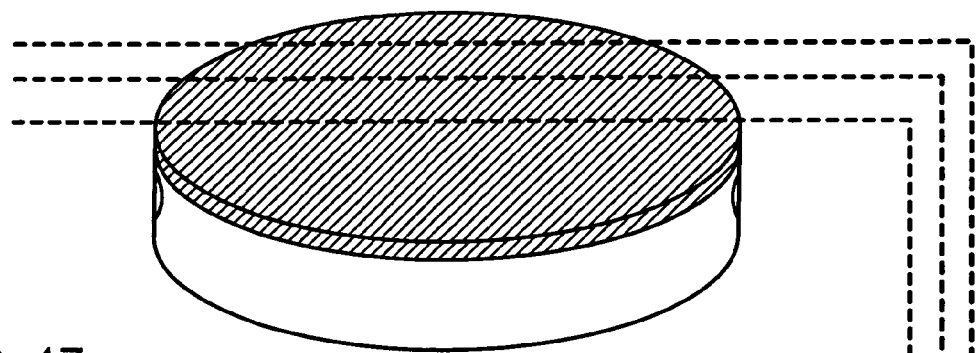
FIG. 17a
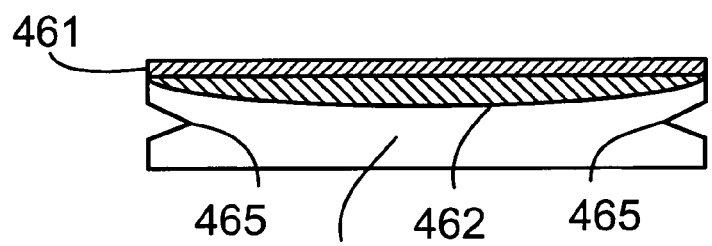
FIG. 17b
FIG. 17c
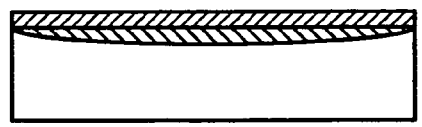
FIG. 17d

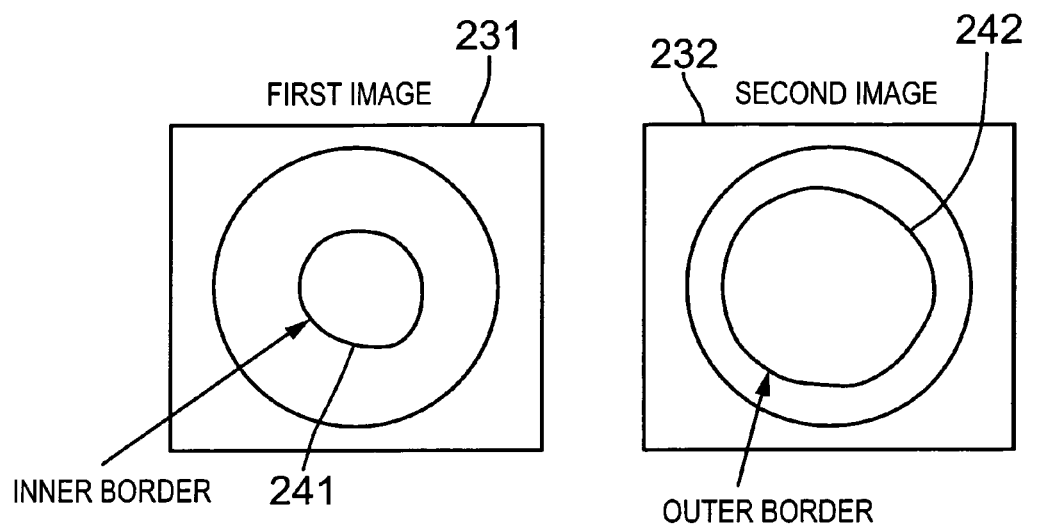
FIG. 24a
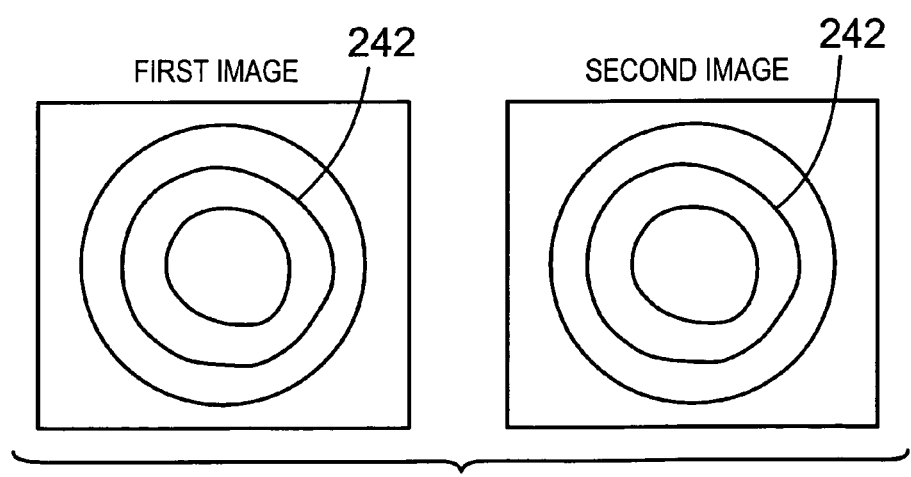
FIG. 24b

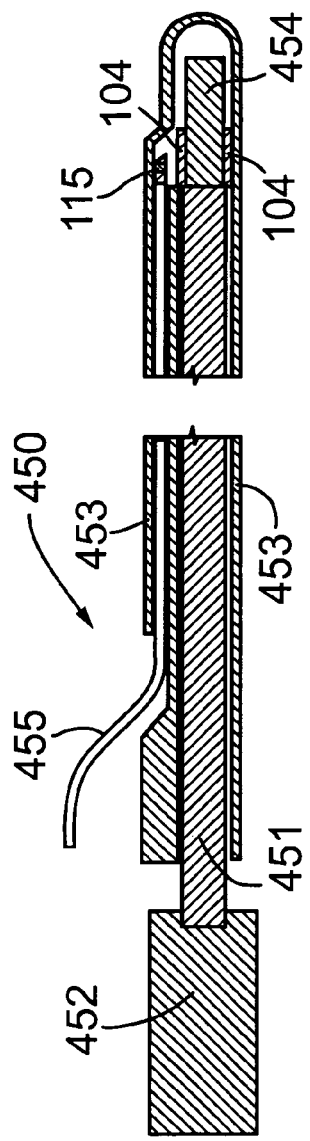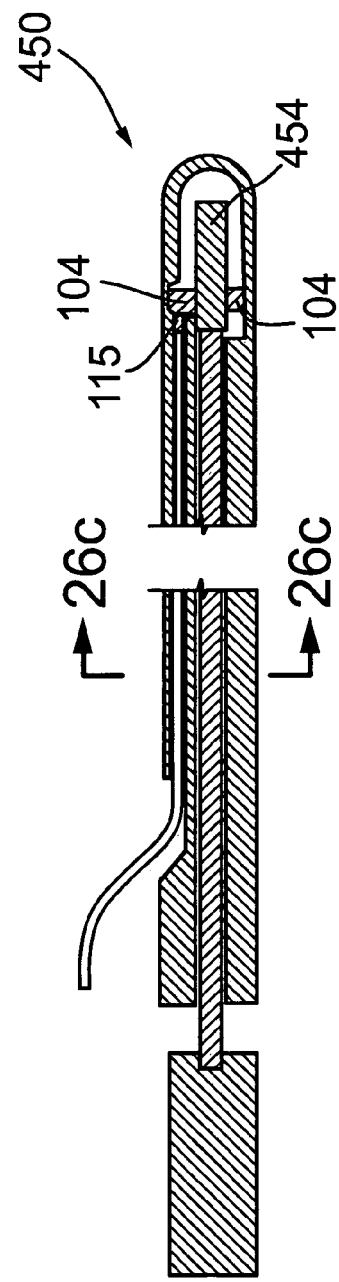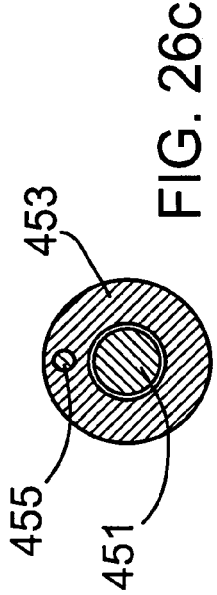
FIG. 26a
FIG. 26b
FIG. 26c

IMAGING PROBE WITH COMBINED ULTRASOUND AND OPTICAL MEANS OF IMAGING

CROSS REFERENCE TO RELATED U.S. APPLICATIONS

This patent application relates to, and claims the priority benefit from, U.S. Provisional Patent Application Ser. No. 60/881,169 filed on Jan. 19, 2007, in English, entitled IMAGING PROBE, which is incorporated herein by reference in its entirety.

FIELD OF THE INVENTION

The present invention relates generally to the field of imaging mammalian tissues and structures using high resolution imaging using combined high frequency ultrasound (IVUS) and optical imaging methods such as optical coherence tomography (OCT) and to accurate co-registering of images obtained from ultrasound image signals and optical image signals during scanning a region of interest.

BACKGROUND OF THE INVENTION

High resolution imaging of the interior of the body (or for dermatologic or ophthalmology applications not restricted to the interior) serves multiple purposes, including any of i) assessing tissue structures, anatomy and composition; ii) planning and/or guiding interventions on localized regions of the body; and iii) assessing the result of interventions that alter the structure, composition or other properties of the localized region. High resolution imaging in this particular case refers to high frequency ultrasound and optical imaging methods. For the purposes of this invention, high frequency ultrasound typically refers to imaging with frequencies of greater than 3 MHz, and more typically in the range of 9 to 100 MHz.

High frequency ultrasound is very useful for intravascular and intracardiac procedures. For these applications, the ultrasound transducers are incorporated into a catheter or other device that can be inserted into the body. By way of example, two particularly important implementations of high frequency ultrasound are intravascular ultrasound (IVUS), for imaging blood vessels, and intracardiac echocardiography (ICE) for imaging cardiac chambers. Both ICE and IVUS are minimally invasive, and involve placing one or more ultrasound transducers inside a blood vessel or cardiac chamber to take high quality images of these structures.

Optical imaging methods based on fiber optic technology used in the field of medicine include optical coherence tomography (OCT), angioscopy, near infrared spectroscopy, Raman spectroscopy and fluorescence spectroscopy. These modalities typically require the use of one or more optical fibers to transmit light energy along a shaft between an imaging site and an imaging detector. Optical coherence tomography is an optical analog of ultrasound, and provides imaging resolutions on the order of 1 to 30 microns, but does not penetrate as deeply into tissue as ultrasound in most cases. Fiber optics can also be used to deliver energy for therapeutic maneuvers such as laser ablation of tissue and photodynamic therapy.

Additional forms of imaging related to this invention include angioscopy, endoscopy and other similar imaging mechanisms that involves imaging a site inside the patient using a probe to take pictures based on the back-reflection of light.

High resolution imaging means have been implemented in many forms for assessing several different regions of mammalian anatomy, including the gastrointestinal system, the cardiovascular system (including coronary, peripheral and neurological vasculature), skin, eyes (including the retina), the genitourinary systems, breast tissue, liver tissue and many others. By way of example, imaging of the cardiovascular system with high frequency ultrasound or optical coherence tomography has been developed for assessing the structure and composition of arterial plaque.

High-resolution imaging has been used to measure vessel or plaque geometry, blood flow through diseased arteries, the effects of interventions on arterial plaque (such as by atherectomy, angioplasty and/or stenting). Attempts have also been made using high resolution imaging to identify vascular lesions that have not led to clinical symptoms, but are at increased risk of rupturing or eroding and causing an acute myocardial infarction. These so-called "vulnerable plaques" are an area of interest as the prospect of treating such plaques to pre-empt adverse clinical events is conceptually appealing.

Chronic total occlusions are a specific subset of vascular lesions where the entire lumen of the vessel has been occluded (based on the angiographic appearance of the lesion) for over approximately one month. Most intravascular imaging modalities are "side-viewing" and require passage of an intravascular imaging device through a lesion. In order to image chronic total occlusions, methods of high resolution imaging would be more useful if they were adapted to a "forward-looking" rather than "side-viewing" configuration.

Several of these high resolution imaging means are dependent on the use of a rotary shaft to transmit torque to an imaging device near the distal end of the probe. These rotary shafts are often long, thin and flexible, such that they can be delivered through anatomical conduits, such as the vasculature, genitourinary tracts, respiratory tracts and other such bodily lumens. Ideally, when a continuous torque is applied to the cable in a specified direction the torque cable develops a property of having a close relation between the degree of rotation at its proximal and distal ends. This allows the simplification of the design of the ultrasound catheter by making the angle of rotation at the distal end of the torque cable (within the body) a reasonable approximation of the angle of rotation at the proximal end of the torque cable (outside of the body).

The rotation of the torque cable or shaft at the point from which the imaging occurs may not be identical to the rotation occurs at the proximal end of the torque cable or shaft. This occurs especially when the flexible shaft is delivered through tortuous passageways and is, at least in part, due to inertia and friction between the rotating components and stationary components of the imaging shaft. The assumption that the rotational speed of the proximal and distal ends of the rotary shaft are equal to each other is also less likely to be valid if the rotational speed varies over time. The undesirable result of not knowing the true angular velocity of the imaging probe at the point from which the imaging beam is directed towards the tissue leads to an artifact referred to non-uniform rotational distortion (NURD). NURD can lead to significant distortion of the image and a concomitant reduction in the geometric accuracy of the image. Knowledge of a more precise estimation of the true rotary speed of the distal rotary shaft or an imaging assembly attached to the rotary shaft can help overcome such distortion by providing more accurate information for image reconstruction. A better estimation of the rotary speed can also help improve the accuracy of co-registration of images when more than one imaging modality is implemented on the imaging probe (such as combined ultrasound and optical imaging).

While use of more than one type of imaging technique, such ultrasound and optical techniques, have both proved valuable in medical applications for high resolution imaging, they are not commonly used in tandem. As described in the Summary of the related art below, there are some designs that exist for the combination of optical and ultrasound technologies. However, the limitations in these designs have prevented their acceptance.

Namely, designs that incorporate optical and ultrasound technologies offset the ultrasound and optical imaging mechanisms, such as disclosed in (Maschke, U.S. Pat. No. 7,289,842 resulting in the acquisition of unaligned ultrasound and optical signals. Alignment of the resultant data from these two imaging means requires movement of the imaging mechanisms and is prone to registration errors due to (i) non-uniform rotational distortion (NURD), (ii) motion of the object occurring between successive imaging of the same location using the two imaging means, (iii) variability in the object being imaged, and (iv) difficulty in accurately tracking the location of the imaging means. All these effects result in inaccurate co-registration which limits the usefulness of the acquisition of data from the two imaging means.

SUMMARY OF THE RELATED ART

A catheter-based system for intravascular ultrasound is described by Yock (U.S. Pat. No. 4,794,931) to provide high resolution imaging of structures in blood vessels. This system comprises an outer sheath, within which there is an ultrasound transducer near the distal end of a long torque cable. When a motor rotates the torque cable and ultrasound transducer assembly, 2D cross-sectional images of anatomical structures, such as blood vessels, can be made. Linear translation of the catheter or the torque cable and ultrasound transducer in combination with the rotational motion of the ultrasound transducer allows for acquisition of a series of 2D images along the length of the catheter.

Milo et al (U.S. Pat. No. 5,429,136) and Lenker et al (U.S. Pat. Nos. 6,110,121 and 6,592,526) describe reciprocating and vibrating means for scanning an ultrasound imaging beam in circumferential or longitudinal directions at the end of the catheter. Reciprocating or vibrating means obviates the need to use a mechanism such as a slip ring to provide an electrical connection to a probe that rotates more than a few rotations in a particular direction, such as more than one or two rotations. Similarly, certain implementations of optical imaging can avoid the use of optical rotary joints using reciprocating or vibrating means.

Liang et al. (U.S. Pat. Nos. 5,606,975 and 5,651,366) describe means of implementing forward-looking intravascular ultrasound where ultrasound is directed towards a mirror that causes the ultrasound beam to propagate at an angle from the longitudinal axis of a rotating torque cable advanced within the vasculature. Liang et al. also describe means of varying the angle of deflection of the mirror using either a micromotor, a gear clutch mechanism, steering cables or bimorph elements such a shape memory alloys, piezoelectric files or conductive polymers. FIG. 13 of U.S. Pat. No. 5,651, 366 shows a diagram of a forward looking ultrasound probe combined with a fiber optic to deliver laser ablation energy via a fiber and mirror in a coaxial direction to the ultrasound imaging beam, but does not relate to combined optical and acoustic imaging or provide for optical focusing elements which would be of benefit for imaging purposes.

The use of intravascular ultrasound (IVUS) has since become commonplace, with many improvements and adaptations to the technology. A flexible torque cable (Crowley, U.S. Pat. No. 4,951,677) improves the fidelity of the transmission of rotational torque along the length of an IVUS catheter, minimizing an artifact known as non-uniform rotational distortion.

The center frequency of IVUS lies within the range of 3 to 100 MHz and more typically in the range of 20 to 50 MHz. Higher frequencies provide higher resolution but result in worse signal penetration and thus a smaller field of view. Depth of penetration can range from less than a millimeter to several centimeters depending on several parameters such as center frequency and geometry of the transducer, the attenuation of the media through which the imaging occurs and implementation-specific specifications that affect the signal to noise ratio of the system.

Variations of high frequency ultrasound exist, where the signal acquisition and/or analysis of the backscattered signal is modified to facilitate obtaining or inferring further information about the imaged tissue exist. These include elastography, where the strain within tissue is assessed as the tissue is compressed at different blood pressures (de Korte et al Circulation. 2002 Apr. 9; 105(14):1627-30); Doppler imaging which assesses motion such as blood flow within anatomic structures; virtual histology, which attempts to infer the composition of tissue using the radio-frequency properties of the backscattered signal combined with a pattern recognition algorithm (Nair, U.S. Pat. No. 6,200,268); second harmonic imaging (Goertz et al, Invest Radiol. 2006 Aug; 41(8):631-8) and others. Each of these forms of imaging can be improved upon by means described in the present invention.

Ultrasound transducers themselves are improving considerably, including the use of single crystal ultrasound transducers and composite ultrasound transducers.

Hossack et al (WO/2006/121851) describe a forward looking ultrasound transducer using a CMUT transducer and a reflective surface.

Tearney et al (U.S. Pat. No. 6,134,003) describe several embodiments that enable optical coherence tomography to provide higher resolution imaging than is readily obtained by high frequency ultrasound or IVUS.

Boppart et al (U.S. Pat. No. 6,485,413) describe several embodiments of optical coherence tomography imaging, including forward-looking implementations. Either an optical fiber or a gradient index (GRIN) lens are displaced using a mechanism such as a motor, a piezoelectric, a moveable wire, inflation means and others.

Mao et al (Appl Opt. 2007 Aug. 10; 46(23):5887-94) describe methods for creating ultrasmall OCT probes using single mode fiber, coupled to a small length of GRIN fiber which acts as a lens. Including an optical spacer between the fiber and the lens can alter the working distance of the fiber-lens system. Furthermore, adding a small length of no-clad fiber to the distal end, and cutting the no-clad fiber at an angle can add a deflecting element to the end of the fiber-lens system. This deflecting element enables side-viewing imaging, which could also be accomplished using a small prism or mirror.

Variations of optical coherence tomography (OCT) include polarization sensitive OCT (PS-OCT) where the birefringent properties of tissue components can be exploited to obtain additional information about structure and composition; spectroscopic OCT which similarly provides improved information regarding the composition of the imaged structures; Doppler OCT which provides information regarding flow and motion; elastography via OCT; and optical frequency domain imaging (OFDI), which allows for a markedly more rapid acquisition of imaging data and therefore enables imaging to occur over a larger volume of interest in less time. Again, each of these forms of imaging can be improved upon by means of the present invention.

Several other forms of fiber-optic based imaging exist other than OCT. Amundson et al describe a system for imaging through blood using infra-red light (U.S. Pat. No. 6,178, 346). The range of the electromagnetic spectrum that is used for their imaging system is selected to be one which optimizes penetration through blood, allowing optical imaging through blood similar to that afforded by angioscopy in the visible spectrum, but without the need to flush blood away from the region being imaged.

Dewhurst (U.S. Pat. No. 5,718,231) discloses a forward looking probe for intravascular imaging where a fiber optic travels through an ultrasound transducer to shine light on a target tissue straight in front of the end of the probe. The light then interacts with the target tissue and makes ultrasound waves, which are received by the ultrasound sensor and the images are photoacoustic images only as the system is not configured to receive and process optical images. The ultrasound sensor used in the Dewhurst device is limited to thin film polymeric piezoelectrics, such as thin film PVDF, and is used only to receive ultrasound energy, not to convert electrical energy to ultrasound.

Angioscopy, endoscopy, bronchoscopy and many other imaging devices have been described which allow for the visualization of internal conduits and structures (such as vessels, gastrointestinal lumens and the pulmonary system) in mammalian bodies based on the principle of illuminating a region within the body near the distal end of a rigid or flexible shaft. Images are then created by either having a photodetector array (such as a CCD array) near the end of the shaft or by having a bundle of fiber optics transmit the received light from the distal end of the shaft to the proximal end where a photodetector array or other system that allows the operator to generate or look at an image representative of the illuminated region. Fiber bundles are bulky and reduce the flexibility of the shaft among other disadvantages.

Other fiber optic based modalities for minimally invasive assessment of anatomic structures include Raman spectroscopy as described by Motz et al (J Biomed Opt. 2006 Mar-Apr; 11 (2)), near infrared spectroscopy as described by Caplan et al (J Am Coll Cardiol. 2006 Apr. 18; 47(8 Suppl): C92-6) and fluorescence imaging, such as tagged fluorescent imaging of proteolytic enzymes in tumors (Radiology. 2004 June; 231(3):659-66).

The ability to combine ultrasound and optical coherence tomography onto a single catheter would be extremely advantageous. Kubo et al presented an interesting in vivo study of coronary arteries using OCT, IVUS and angioscopy to assess the morphology of lesions that have caused an acute myocardial infarction (Journal of American College of Cardiology, Sep. 4, 2007, 10(50):933-39). They demonstrate that there are benefits to imaging with each of these modalities. However, in order to execute their study, they had to use separate catheters for each of IVUS, OCT and angioscopy imaging modalities as no catheters that combine these functions have been commercialized to date. Kawasaki et al previously compared OCT, conventional IVUS and a variant of IVUS known as integrated backscatter IVUS on cadaveric specimens of coronary arteries using separate probes for the OCT and IVUS components. Brezinski et al (Heart. 1997 May; 77(5): 397-403) had previously demonstrated ex vivo studies on dissected aortic specimens where IVUS and OCT images were compared, again using separate probes. The OCT probes in this latter study were not suitable for in vivo use.

Optical coherence tomography generally has superior resolution to ultrasound and has the potential to better identify some structures or components in vascular and other tissues than ultrasound. For example, fibrous cap thickness or the presence of inflammatory or necrotic regions near the surface of arteries may be better resolved with optical coherence tomography. However, optical coherence tomography is limited by its small penetration depth (on the order of 500 to 3000 microns) in most biologic media. Most such media are not optically transparent.

Meanwhile, ultrasound has the ability to better penetrate through biological media such as blood and soft tissues and has a depth of penetration that typically extends several millimeters or centimeters beyond that of optical coherence tomography. The ability to image with either or both methods of imaging using a combined imaging device provides advantages with respect to selecting the required resolution and depth of penetration. Furthermore, much of the information acquired by optical coherence tomography is complementary to that acquired by ultrasound and analysis or display of information acquired by both imaging methods would improve the ability to better understand the interrogated tissue, such as with respect to its composition.

These differences between IVUS and OCT are well known in the art. Maschke (United States Patent Publication No. 2006/0116571 corresponding to U.S. patent application Ser. No. 11/291,593) describes an embodiment of a guidewire with both OCT and IVUS imaging transducers mounted upon it. The described invention has several shortcomings. Guidewires are typically 0.014" to 0.035" in diameter (approximately 350 microns to 875 microns), yet ultrasound transducers typically are at least 400 microns×400 microns and generally are larger in size for the frequencies in the 20 to 100 MHz range. If the transducer is too small, the beam is poorly focused and has poor signal properties. In Maschke the IVUS and OCT imaging mechanisms are located at different positions along the length of the guidewire and a drawback to this type of configuration having the IVUS and OCT imaging means located at different positions along the length of an imaging shaft does not allow for optimal co-registration of images.

U.S. Pat. No. 7,289,842) issued to Maschke describes an imaging system that combines IVUS and OCT on a catheter where the IVUS and OCT imaging elements are longitudinally displaced from each other along the length of a catheter that rotates around its longitudinal axis. Maschke also describes generating images where the center portion of the images are substantially derived from the output of the higher resolution OCT imaging portion of the system while the outer portion of the images are substantially derived from the output of the ultrasound imaging portion of the system, to make use of ultrasound's greater depth of penetration in combination with OCT's higher resolution for tissues close to the catheter.

Park et al (U.S. patent application Ser. No. 11/415,848) also briefly refers to the notion of having a catheter that combines IVUS and OCT imaging onto a single catheter.

However, the integration of means for combined acoustic and optical imaging, such as combined IVUS and OCT imaging, onto a single device is not trivial. Having an optical imaging element and an acoustic imaging element longitudinally separated from each other on a primarily rotating catheter does not provide an ideal configuration for combined imaging. A more ideal configuration would enable the acquisition of high quality acoustic and optical signals from which ultrasound and optical-based images could be made while enabling the acoustic and optical images to be registered with each other in a highly precise manner.

For example, by simply placing an IVUS imaging element in line with an OCT imaging element along the length of the catheter, the center of the imaging planes of the IVUS and OCT images will be separated from one another by a distance of at least approximately half the length of the ultrasound transducer and half the length of the optical imaging elements.

Mechanical IVUS transducers for vascular imaging are typically more than 400 microns in length. The separation between the IVUS and OCT planes of imaging in a configuration such as that proposed by Maschke would require at least 250 microns of separation between the optical and acoustic imaging planes. Typically, mechanical IVUS rotates at 30 frames per second with a pullback rate of 0.5 mm/s, meaning that from a given time point $t_0$, at least 15 imaging frames or 500 milliseconds would elapse between the time that the more distally placed imaging means would translate to the same position at which the more proximally placed imaging means was originally positioned at time $t_0$. This separation of several hundred milliseconds or several rotations of the imaging probe makes it difficult to precisely register the imaging data from one imaging means with the other.

This is particularly relevant given the fact that the catheter can undergo significant unintentional lateral and longitudinal displacements within body lumen in that time period, such as those displacements that occur as a result of cardiac contraction and pulsatile flow. Non-uniform rotational distortion (NURD) can also have an impact on the ability to accurately register images acquired several rotations apart from each other. Any imprecision of the registration of the two data sets is even more significant when one considers the scale at which important pathologies, such as vulnerable plaques can be found. Dramatic differences in the appearance of an arterial plaque's composition (e.g. the thickness of a fibrous cap, the presence of a calcified nodule or the extent of an atheromatous deposit) can be observed in as little as a few hundreds microns along the length of a vessel. Similarly, small but potentially relevant sidebranches of anatomic conduits, such as blood vessels, can have dimensions on the order of less than a hundred microns.

Previous experiments and implementations of IVUS and OCT or other combinations of acoustic and optical imaging have not been provided that enable significant precision in the registration of the imaging data from the two or more imaging means in a manner that is suitable for minimally invasive imaging, such as intravascular imaging.

To the best of our knowledge, previous experiments and implementations of IVUS and OCT or other combinations of acoustic and optical imaging have not been provided that enable significant precision in the registration of the imaging data from the two or more imaging means in a manner that is suitable for minimally invasive imaging, such as intravascular imaging.

It would be very advantageous to also provide high resolution imaging probes that combine acoustic and optical imaging onto "forward-looking" probes rather than "side-viewing" probes. It would also be helpful to provide similar probes that can look backwards, or from multiple angles in a generally side-viewing configuration.

It would also be advantageous to provide high-resolution imaging probes that combine ultrasound imaging with one or more optical imaging means.

It would also be advantageous to provide minimally invasive imaging probes that can be used for photoacoustic imaging or sonoluminescent imaging.

It would also be advantageous to provide minimally invasive imaging means where on of the imaging means provides helpful information regarding the direction in which the other imaging means is acquiring imaging data.

SUMMARY OF THE INVENTION

The present invention provides embodiments of imaging probes for combining acoustic and optical imaging means in a manner that facilitates simultaneous imaging by two or more imaging methods. The embodiments enable methods to accurately co-register the images obtained from each of the modalities. In some embodiments, the current invention provides embodiments for combining acoustic imaging means with the delivery of therapeutic energy, such as ultraviolet light for photodynamic therapy or laser energy for ablation procedures.

The present invention also provides embodiments where one form of imaging is used to help with the reconstruction of the second form of imaging. This is more specifically related to monitoring the position or orientation of a component in the image probe that subsequently determines the position or orientation of the imaged region.

The present invention provides methods for combining high frequency ultrasound and optical coherence tomography into a combined imaging system.

The present invention provides novel means for implementing a combined ultrasound and optical imaging system where the volume scanned includes a region either forward of, or behind, the location of the imaging transducers.

The present invention provides the ability to take images similar to those produced by angioscopy, endoscopy and similar imaging techniques using a single optic or a small number of fiber optics, in combination with means to acquire ultrasound images. These optical images can also be acquired using infrared and/or visible wavelengths.

The present invention provides means for combining high frequency ultrasound and optical coherence tomography where the volumes scanned include regions either forward of, or behind, the locations of the imaging transducers.

Embodiments of the present invention are able to scan a region for the purposes of imaging or delivery of therapeutic energy the region accessed by a shaft where changes in the rotation velocity of the shaft causes changes in the direction of either an emitter and/or receiver of acoustic and/or optical energy.

The present invention also facilitates certain forms of high resolution imaging that use acoustic energy to create optical energy (sonoluminescence imaging) or optical energy to create acoustic energy (photoacoustic imaging).

An embodiment of the present invention provides an imaging probe for insertion into bodily lumens and cavities for imaging an interior of said bodily lumens and cavities or imaging exterior surfaces of a body, comprising:

a) an hollow shaft having a longitudinal axis having distal and proximal end sections and an midsection, an imaging assembly being located in said hollow shaft, said imaging assembly being connected to a first end of an imaging conduit, said imaging conduit extending through the hollow shaft and being connectable at a second end thereof to an image processing and display system through the proximal end section, said imaging conduit including a fiber optic having a distal end and said imaging assembly including an optical emitter/collector including light directing and receiving means associated with said distal end of a fiber optic for directing light imaging energy out of a distal end of said fiber optic and receiving reflected light imaging energy signals and directing said received reflected light energy signals back to said image processing and display system, said imaging assembly including an ultrasound transducer and said ultrasound transducer emitting and receiving reflected ultrasound imaging energy signals and said imaging conduit including an electrical conductor for electrically coupling the ultrasound transducer to an ultrasound signal generator connectable to said second end of said imaging conduit, said imaging conduit being connectable at said second end to a source of light;

b) said imaging assembly including a scanning mechanism configured to deliver said light from the optical emitter/collector and ultrasound from said ultrasound transducer along pre-selected paths out of said hollow shaft, the ultrasound transducer and the optical emitter/collector being positioned and oriented relative to each other to enable accurate co-registering of received reflected light imaging energy signals and reflected ultrasound imaging energy signals during scanning a region of interest; and c) drive mechanism for imparting motion to said imaging conduit and said imaging assembly, said drive mechanism being connectable to a controller which is connectable to said image processing and display system.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

FIG. 2 is a perspective drawing of a flexible imaging probe with an adapter, conduit and imaging assembly;

FIG. 2a is a cross sectional view of the mid section of the imaging probe of FIG. 2 taken along the dotted line;

FIG. 2b is an expanded perspective drawing of the distal region of the imaging probe of FIG. 2;

FIG. 3a shows one embodiment of an over-the-wire configuration for an external sheath that may be incorporated with the imaging probe if a guidewire lumen is included;

FIG. 3b shows a cross-section through the imaging probe to demonstrate the guidewire lumen configuration.

FIG. 3c shows a rapid access configuration for an external sheath that may be incorporated with the imaging probe if a guidewire lumen is included;

FIG. 3d shows a cross-section through a portion of the imaging probe that does not contain a guidewire lumen;

FIG. 3e shows a cross-section through a portion of the imaging probe that does contain a guidewire lumen;

FIGS. 4a to 4l are examples of ultrasound transducers that contain a hole for allowing transmission of optical energy through the transducer that enables optical and acoustic imaging of regions that are precisely aligned with each other, as well as means to deflect the path of the imaging light;

FIGS. 7a to 7e show examples of ultrasound transducers that have an optical apparatus for transmitting and/or receiving optical imaging energy either on top of or recessed within an acoustic transducer;

FIG. 8a is a perspective view of an imaging assembly suitable for side viewing with both acoustic and optical imaging;

FIG. 8b is a side view of the imaging assembly in FIG. 8a;

FIGS. 8c to 8e are end views of the imaging assembly in FIG. 8a in different rotated positions;

FIGS. 9a to 9c depict configurations whereby an optical imaging emitter/receiver is embedded into the backing material 435 of an acoustic transducer.

FIG. 16b is a view along the line 16b-16b of FIG. 16a;

FIG. 17a is a perspective drawing of a deflecting component that comprises a flat optically reflective layer and a shaped acoustically reflective layer;

FIGS. 17b through 17d depict cross-sections of the deflecting component of FIG. 17a;

FIGS. 24a and 24b demonstrate how a contour feature in a first image can be mapped into another image with is co-registered with the first image and vice versa;

FIG. 26a to 26c shows cross sectional views of an imaging probe with a rotary encoder.

DETAILED DESCRIPTION OF THE INVENTION

Without limitation, the majority of the systems described herein are directed to an imaging probe that enables imaging by both optical and acoustic means. As required, embodiments of the present invention are disclosed herein. However, the disclosed embodiments are merely exemplary, and it should be understood that the invention may be embodied in many various and alternative forms.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an imaging probe that enables imaging by both optical and acoustic means.

As used herein, the term "about", when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region. For example, in embodiments of the present invention dimensions of components of an imaging probe are given but it will be understood that these are not meant to be limiting.

As used herein, the phrase "co-registration of images" refers to the process of identifying a subset of imaging data acquired by one imaging means with a subset of imaging data acquired using another imaging means where the identified imaging data from the two means was acquired by detecting a form of imaging energy (e.g. photons or ultrasound) from the same object (or tissue in the case of the present invention). Each co-registered point in the first subset can then be mapped to a corresponding point in the second subset such that the two points from the two different imaging means are thought to have been acquired from a similar focal region of the imaged object (or tissue).

Successful and accurate co-registration of images, or portions thereof, between images acquired using two (2) or more imaging means is helpful in that it can provide multiple opportunities to assess features of interest of the imaged object by more than one imaging means.

Figure 1:
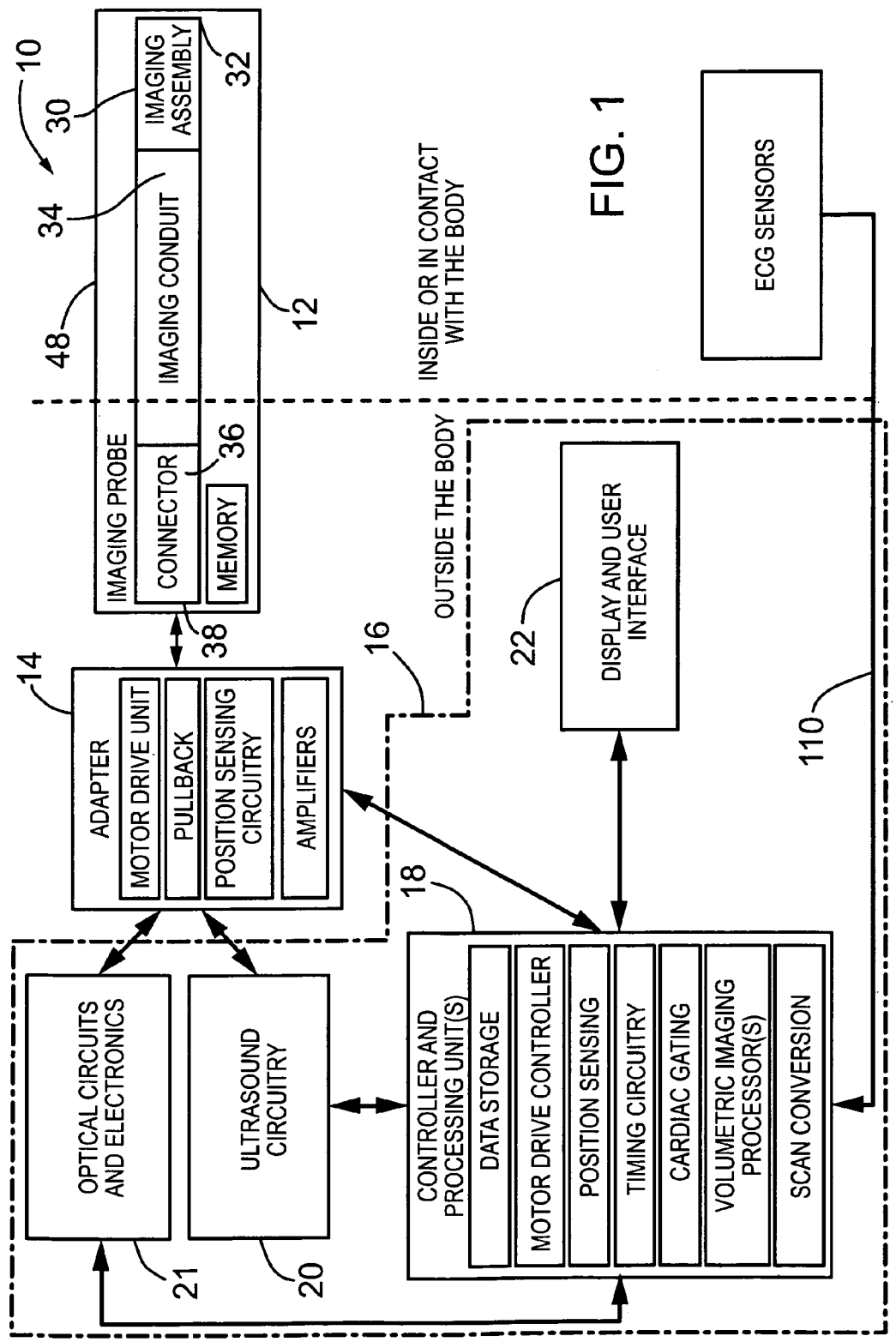
FIG. 1 is a schematic of an imaging system including ultrasound and optical imaging components.

FIG. 1 represents an overview of an exemplary imaging system constructed in accordance with the present invention shown generally at 10. It comprises an imaging probe 12, which connects via an adapter 14 to an image processing and display system 16. The image processing and display system 16 comprises the necessary hardware to support one or more of the following imaging modalities: 1) ultrasound, 2) optical coherence tomography, 3) angioscopy, 4) infrared imaging, 5) near infrared imaging, 6) Raman spectroscopy-based imaging and 7) fluorescence imaging.

Implementations of the optical coherence tomography, ultrasound, angioscopy and infrared imaging circuitry have been described in the prior art.

The system herein described further typically comprises a controller and processing unit 18 to facilitate the coordinated activity of the many functional units of the system, and may further comprise a display and/or user interface and may further comprise electrode sensors to acquire electrocardiogram signals from the body of the patient being imaged. The electrocardiogram signals may be used to time the acquisition of imaging data in situations where cardiac motion may have an impact on image quality. The optical circuits and electronics 21 forming image processing and display system, if included in a particular implementation of the present invention, may include any or all of the following components: interferometer components, one or more optical reference arms, optical multiplexors, optical demultiplexors, light sources, photodetectors, spectrometers, polarization filters, polarization controllers, timing circuitry, analog to digital converters and other components known to facilitate any of the optical imaging techniques described in the background and prior art sections. The ultrasound circuitry 20 may include any or all of the following components: pulse generators, electronic filters, analog to digital converters, parallel processing arrays, envelope detection, amplifiers including time gain compensation amplifiers and other components known to facilitate any of the acoustic imaging techniques described in the background and prior art sections.

The controller and processing units 18, if included in a particular implementation of the present invention, serve multiple purposes and the components would be markedly adapted based on the needs of a particular imaging system. It could include one or a combination of motor drive controller, data storage components (such as memory, hard drives, removable storage devices, readers and recorders for portable storage media such as CDs and DVDs), position sensing circuitry, timing circuitry, cardiac gating functionality, volumetric imaging processors, scan converters and others. A display and user interface 22 is also optionally provided for either real time display or display of data at a time later than the time at which imaging data is acquired.

The imaging probe 12 comprises an imaging assembly 30 near its distal end 32, an optional conduit 34 along a substantial portion of its length, and a connector 36 at its proximal end 38. For the purposes of this invention, an imaging assembly 30 generally refers to the component of the imaging probe 12 from which the signals (acoustic or optical (or both)) are collected for the purposes of imaging a region that is proximate to the imaging assembly 30. The imaging assembly 30 includes at least one or more emitters of imaging energy and at least one or more receivers of imaging energy. For the purposes of this invention, "imaging energy" refers to both light and acoustic energy. Specifically, light refers to electromagnetic waves that span the ultraviolet, visible and infrared spectrum of wavelengths. For example, for acoustic imaging, the imaging assembly 30 contains an ultrasound transducer that is both an emitter and receiver of acoustic energy.

For optical imaging, the imaging assembly 30 typically contains the distal tip of a fiber optic, as well as a combination of optical components such as a lens (such as a ball lens or GRIN lens), which collectively serve the purpose of acting as an optical receiver and may also serve as an optical emitter. A mirror and/or a prism are often incorporated as part of an optical emitter and/or receiver. The imaging assembly 30, connector 36 and/or imaging conduit 34 may be liquid-filled, such as with saline and may be flushed.

The imaging probe 12 may contain ports at one or more points along its length to facilitate flushing. For optical imaging, it is possible to consider a gas filled imaging probe 12. Preferably, the gas would substantially comprise carbon dioxide or another readily dissolved gas. Alternatively, the imaging assembly may be compartmentalized such that there is at least one gas-filled compartment or lumen for optical imaging and at least one fluid-filled compartment or chamber for acoustic imaging.

The imaging conduit 34 comprises at least one optical waveguide and at least one conductive wire (preferably two or more) that connect an emitter and/or receiver via a connector to an adapter. The imaging conduit 34 may also act as a mechanical force transmission mechanism for rotating or translating the imaging assembly. For example, the imaging conduit 34 may comprise a fiber optic, wrapped by two layers of electrical wire that are insulated by each other. The imaging conduit 34 may further be reinforced by other structural features, such as helically wrapped wires or other designs used to construct imaging torque cables for rotating scan mechanisms, as described in the prior art.

The adapter 14 facilitates transmission of signals within any fibers and/or wires to the appropriate image processing units. The adapter 14 may also incorporate a pullback mechanism 49 (FIG. 2d) or a reciprocating push-pull mechanism to facilitate longitudinal translation of the imaging assembly. Such longitudinal translation of the imaging assembly 30 may occur in conjunction with the longitudinal translation of an external shaft that surrounds the imaging conduit 34, or may occur within a relatively stationary external shaft.

Additional sensors may be incorporated as part of the adapter 14, such as position sensing circuitry, for example to sense the angle of rotation of a rotary component within the imaging probe 12. The imaging probe 12 may also include a memory component such as an EEPROM or other programmable memory device that includes information regarding the imaging probe to the rest of the imaging system. For example, it may include specifications regarding the identification of specifications of the imaging probe 12 and may also include calibration information regarding the probe 12.

While precise alignment of the acoustic and optical imaging data is highly desired, it is also important to recognize the need to optimize the geometry of a minimally invasive probe so that it is as small as reasonably possible to achieve its desired purpose. Current IVUS probes are approximately 0.9 to 2 mm in diameter and the smaller sizes of probes can be delivered more distally within the vascular tree of the coronary anatomy as the vessel size tapers down. Thus, smaller sizes generally allow for interrogation of a larger portion of the coronary anatomy. It is therefore desirable to have embodiments of a probe that combines optical and acoustic imaging in arrangements that minimize certain dimensions of the probe, such as the diameter of the probe.

FIG. 2 is a perspective drawing of a flexible catheter containing a fiber optic 40 and a co-axial electrical wire 50. The proximal connector contains fiber optic 40 that can be received by the adapter to optically couple the imaging fiber optic 40 to the optical imaging system "back-end". There are also electrical connectors 56 that allow the one or more electrical conduits to be connected to the ultrasound circuitry 20 and/or controller and processing units 18. In embodiments where the imaging conduit rotates around its longitudinal axis, there may be a need to couple the rotating components of the imaging fiber optic with the relatively stationary fiber optic that connects to the optical imaging system's back-end 21. The coupling of a rotating fiber optic probe can be accomplished using a fiber optic rotary joint incorporated either as part of the proximal connector of the imaging probe 10 or as part of the adapter 14. Similarly, in embodiments where the imaging conduit rotates around its longitudinal axis, there may be a need to couple the conductive wires that rotate with the imaging conduit with the relatively stationary conductors of the ultrasound circuitry 20 and/or controller and processing units 18, preferably by means of slip rings. These slip rings can be incorporated as part of the proximal connector of the imaging probe 36 or as part of the adapter 14.

FIG. 2a shows a cross sectional view of the mid section of the imaging probe of FIG. 2 taken along the dotted line which shows a fiber optic 40, guidewire port 44 and guide wire 42, imaging conduit 34, imaging conduit lumen 46, external sheath 48 which is a hollow, flexible elongate shaft made of a physiologically compatible material and having a diameter suitable to permit insertion of the hollow elongate shaft into bodily lumens and cavities, and coaxial electrical wiring 50. The expanded detailed view of the end of the imaging probe 10 shown in FIG. 2b shows the distal end of the guidewire 42 extended beyond the end of the outer sheath 48 and a flush port 54 at the end of the sheath 48. In FIG. 2 the proximal end of the imaging probe 10 includes another guidewire port 55 into which guidewire 42 is inserted and the connector assembly 36 which includes a flush port 58 and electrical contacts 56 along the connector body.

Figure 2C:
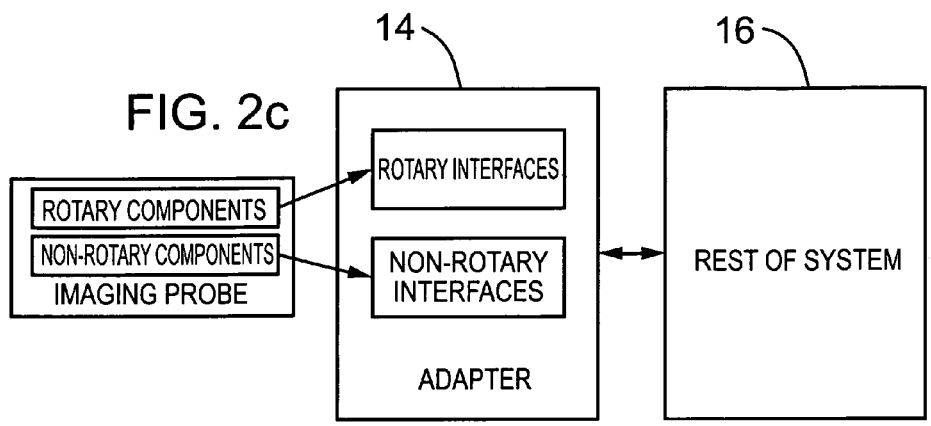
FIG. 2c shows a schematic of how the rotary and non-rotary components of the imaging probe can be coupled with an adapter to the rest of an imaging system.
Figure 2D:
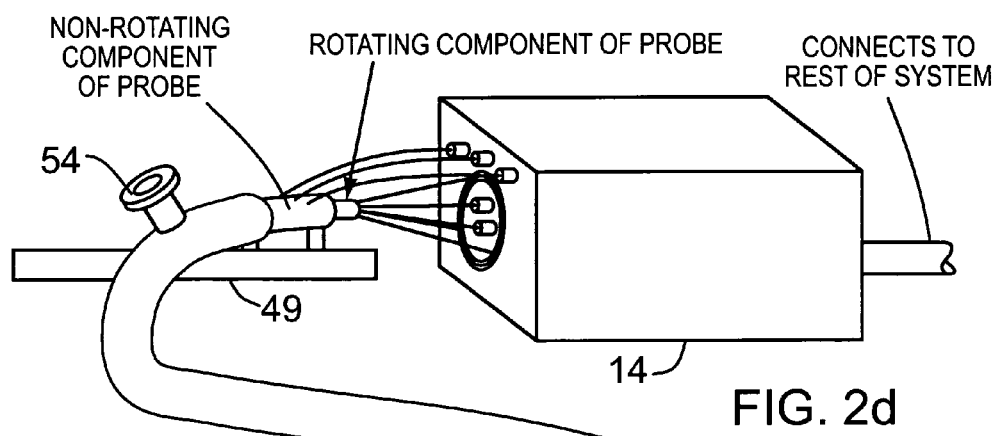
FIG. 2d is a perspective drawing of an example of the coupling of the rotary and non-rotary components of the probe to an adapter.

FIG. 2c shows a schematic of how the rotary and non-rotary components of the imaging probe can be coupled with an adapter to the rest of an imaging system. FIG. 2d schematically shows how the rotating components of the imaging probe can be coupled to the rotating components of an adapter. The rotating components of each can be electrically, optically and/or mechanically coupled using connectors and other configurations known in the art. Similarly, the non-rotating components of the imaging probe can be coupled to the non-rotating components of the adapter 14. The adapter 14 can include slip rings, optical rotary joints and other such implements for electrically or optically coupling a rotary component to a non-rotary component and enable communication of necessary electrical and optical signals with the rest of the system.

Dual-fiber optical rotary joints are also available but considerably more complex. Electrical coupling between any conductor mounted onto a rotating component in the imaging probe 12 can be coupled to non-rotating conducting elements via metallic slip rings and springs, metallic slip rings and brushes or other commonly known methods of forming conductive contact between a stationary conductor and a rotary conductor.

While the electrical, optical and mechanical connections are shown separately in FIG. 2d, it is possible to reduce the several connectors that must each be separately connected between the probe and adapter with fewer connectors by combining several connectors into combined connectors, as needed for a specific embodiment.

Figure 3A:
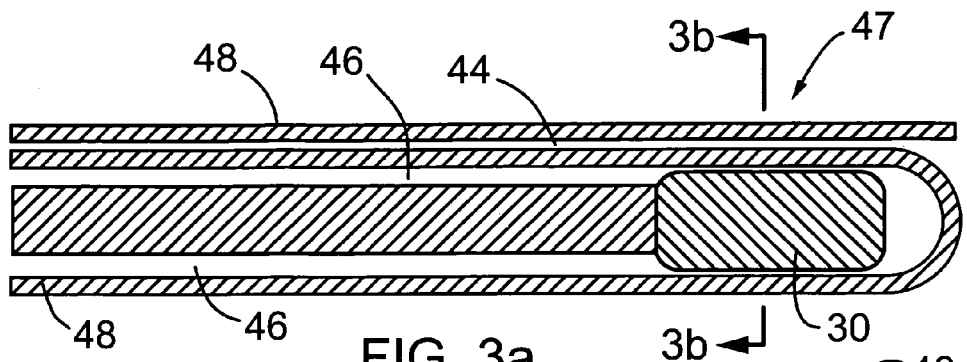
FIGS. 3a to 3e are representative of general imaging catheter configurations described in the prior art.
Figure 3B:
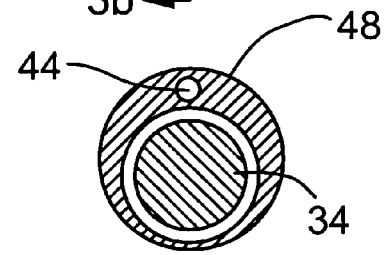

FIG. 3a shows one embodiment of an over-the-wire configuration for an external sheath at 47 and FIG. 3b shows a cross-section of sheath 47 through the portion that contains the imaging assembly 30 along the vertical line 3b-3b in FIG. 3a.

Figure 3C:
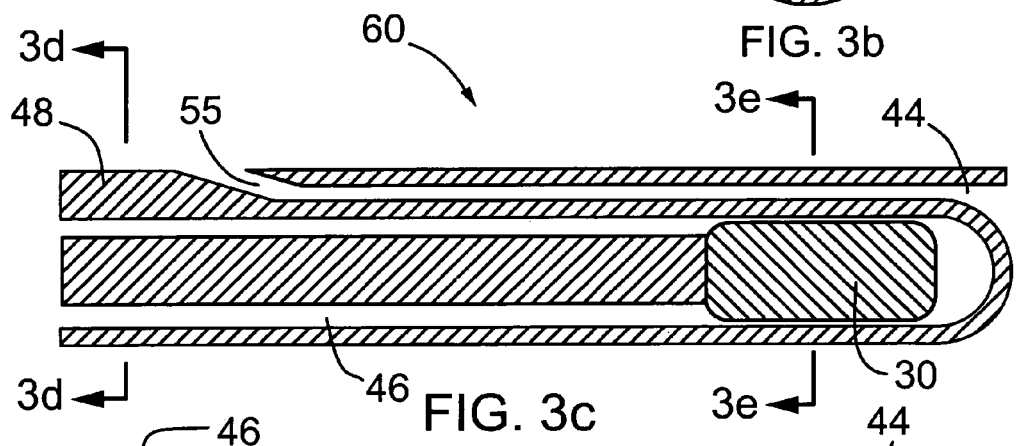
Figure 3D:
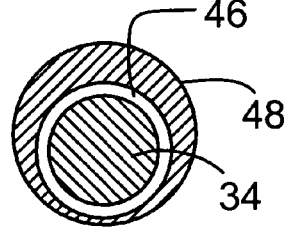
Figure 3E:
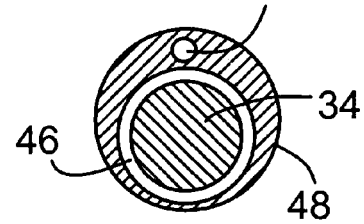

FIG. 3c shows an embodiment at 60 that is a "rapid exchange" configuration for the external sheath that may be incorporated with the imaging probe if a guidewire is required. Sheath 60 in FIG. 3c includes the entry port 55 shown in FIG. 2. FIG. 3d shows a cross-section of the "rapid-exchange" configuration 60 through the portion that is proximal to the entry port 55 for a guidewire along line 3d-3d in FIG. 3c. FIG. 3e shows a cross-section along line 3e-3e in FIG. 3c.

The present invention describes several embodiments by which precisely registered ultrasound and optical images can be formed. The simplest conceptual approach is to have the paths of the ultrasound and optical imaging beams be aligned collinearly with each other.

Referring to FIG. 4a, an imaging probe 399 is provided which is configured to allow imaging by acoustic and optical means in the same direction, so that an acoustic transducer that allows light energy to travel through a channel in the transducer is utilized. Essentially, probe 399 uses an acoustic transducer 402 that is altered to have an optically transmissive channel made through its substrate. The acoustic transducer 402 can be any kind of ultrasound transducer known in the art, such as piezoelectric composition (e.g. PZT or PVDF), a composite transducer or a single crystal transducer.

Electrical conductors 400 are directed to the conducting layers 401 on either side of the transducer's acoustic substrate 402. A fiber optic 403 provides an optical conduit for enabling optical imaging. One or more matching layers can be added to the emission surfaces of the transducer, such as an epoxy layer (such as a silver or copper conductive epoxy layer which may functionally also serve as one or both of the electrodes that drives the transducer), or a polymer (such as parylene or PVDF).

The optically transmissive channel 407 is made by any of several techniques, such as precision drilling, laser ablation, photo-etching, inclusion of a feature in a mold to create the opening and others. Precision drilling may include the use of drill bits, such as diamond or carbide drill bits explicitly designed for cutting through hard materials. A high precision spindle, such as an air spindle, may be helpful for accurate and efficient execution of the drilling technique. A laser source can be used to ablate a channel through the substrate. Exemplary laser sources include YAG or excimer lasers.

Alternatively, if the acoustic transducer 402 is formed from a substrate that is initially viscous, a sacrificial component can be embedded in the piezoelectric during the formation of the piezoelectric transducer 402. The sacrificial component can then be removed by mechanical means or exposure to a solvent. For example, a polystyrene cylinder can serve as the sacrificial component, which can be subsequently sacrificed using dissolution in acetone. Alternatively, if the piezoelectric material 402 is formed from a substrate that is initially viscous, a removable mandrel can be included in the material during the formation of the piezoelectric transducer and removed after the piezoelectric has partially or substantially hardened.

Conductive layers 401 on either side of the piezoelectric material 402 are incorporated as required for applying a voltage to the piezoelectric. The opening 407 is coupled to an optical waveguide 403, either directly, or by means of one or more mirrors 404 or prisms 397 and one or more lenses 405. If any optical components are included within the opening, a dampening, insulating layer of a compliant material 406 (see FIG. 4l), such as silicon or polymer may separate the optical components from the acoustic substrate 402 to act as either an electrical insulator or to minimize the transmission of stresses that are generated by the acoustic substrate 402 to the optical components.

As in FIG. 4b, the light from the fiber can be directed towards a mirror 404 (or prism) that causes the light from the fiber to be deflected through the optically transmissive channel 407. Alternatively, as in FIG. 4c, a prism 397 can be used to deflect the light through the optically transmissive channel. The prism 397 may deflect light either as a result of total internal reflection or be assisted by a reflective coating on its deflecting surface 419. The prism 397 may be a separate optical component that is affixed to the appropriate position along the optical path. For example, it can be glued in place onto the end of a fiber, onto a lens or onto a spacer using bonding methods such as UV cured glue. Alternatively, attaching a no-clad optical fiber along the optical path and cutting the segment of no-clad fiber at a desired length can be performed to make the prism. The segment of clad fiber can be cut and/or polished to achieve the desired angle. Mao describes this method in the previously cited reference.

Also seen in FIG. 4c, an optically transparent window 409 may optionally be found at the end of the optically transmissive channel 407 and any unoccupied space within the channel may be filled with a gas, fluid or optically transparent material such as glass or any of several transparent polymers known in the art. The purpose of the window 409 is to prevent undesired air bubbles from being created or retained in the channel 407 and to protect the components in the optically transmissive channel 407.

As seen in FIG. 4d it may be desirable to have a gas instead of fluid or solid material inside the channel 407 to improve the refractive power of certain optical components such as a contoured lens 424, which may be a ball lens.

Figure 4H:
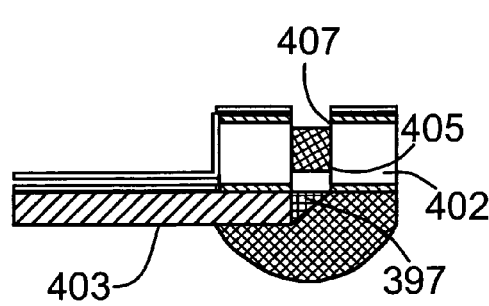
Figure 4J:
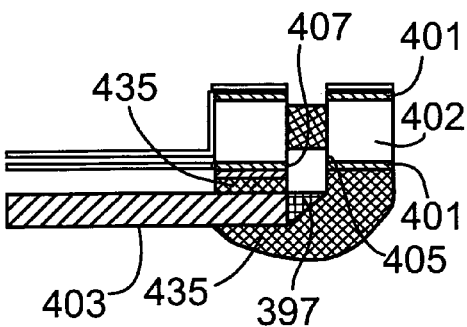

As seen in FIGS. 4e to 4g, the GRIN lens 405 or other optical component can reside adjacent to the distal dip of the optical fiber 403, between the fiber 403 and the deflecting mirror or prism 397 along the optical path. In this case, the opening 407 in the acoustic substrate 402 can be left free of any optical components and simply contain an optically transparent material, or be covered by a window 409. Alternatively, the GRIN lens 405 or other optical component can reside in the optically transmissive channel 407 of the acoustic substrate 402, as seen in FIGS. 4g to 4l. The sleeve of insulating material 406 mentioned above can surround the GRIN lens 405 or other optical component within the opening 407 as shown in FIG. 4l in order to provide either mechanical or electrical insulation from the acoustic substrate 402.

Referring to FIG. 4f an optical spacer 433 is located between the distal end of the optical fiber 403 and GRIN lens 405. The optical spacer element 433 may comprise an optically transparent medium, such as no-clad fiber, glass, plastic, a gas-filled gap or a fluid-filled gap. The use of an optical spacer element 433 may help reduce the required precision for the alignment and sizes of optical components in order to achieve a desired focal length.

Alternatively, as seen in FIG. 4g, the path length of the prism 397 or mirror can act as all or a portion of the optical spacer 433 in between the distal end of the optical fiber and the lens 405. The advantage of using the distance that light must travel through the mirror or prism 397 as a substitute for a portion of a functional optical spacer is that the focusing element (e.g. the GRIN lens 405 or other lens) is closer to the region being imaged, thus improving the effective working distance of the optical imaging system. In some situations, the lens 405 can be offset from either edge of the optically transmissive channel to achieve the desired depth of focus, as in FIG. 4h.

Figure 4I:
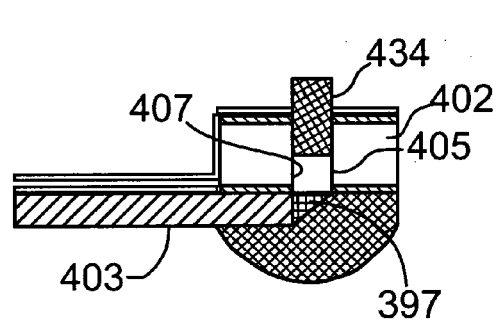

In other embodiments, it may be helpful to have one or more optical elements of the optical path extend beyond the outer surface of the acoustic transducer, such as element 434 as in FIG. 4i, in order to achieve the desired performance of the optical imaging technique. This is particularly important when the acoustic transducer 402 is quite thin (such as a for very high ultrasound frequencies) or when the effective working distance of the optical imaging technique is longer than can be accommodated by having all the optical components reside below the emitting surface of the acoustic transducer.

It is also important to realize that the optical circuit can be distant from the surface of the acoustic transducer 402. By way of example, as seen in the embodiment shown in FIG. 4j, it may be desirable to have some backing material 435 interposed between the fiber optic 403 or other optical components proximal to the deflecting mirror or prism 397 and the acoustic transducer 402 to minimize back-reflections from the optical components.

Figure 4K:
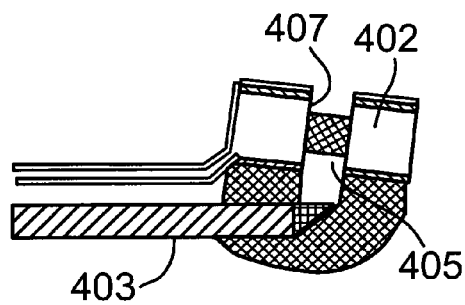
Figure 4L:
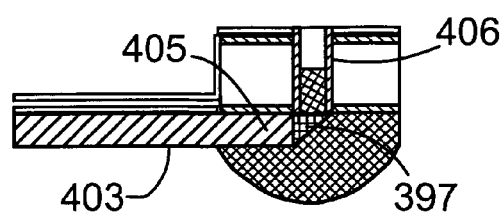

The direction of propagation of the acoustic and optical imaging energy can be in a direction other than perpendicular to the longitudinal axis of the imaging probe. In fact, a slight angular offset of a few degrees is desired to minimize reflections back from the sheath that surrounds the probe. FIG. 4k shows an embodiment of a probe that combines optical and acoustic imaging means aligned at an angle other than normal to the longitudinal axis of the probe.

Figure 5A:
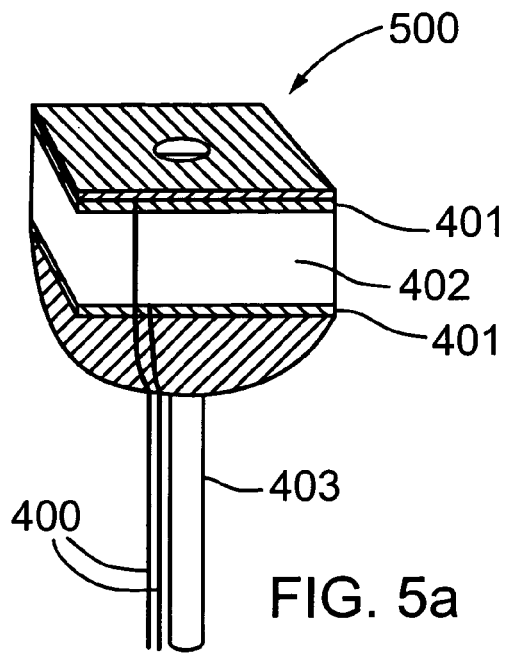
FIGS. 5a to 5f are examples of ultrasound transducers that contain a hole for allowing transmission of optical energy through the transducer that enables optical and acoustic imaging of regions that are precisely aligned with each other, without a means to deflect the path of the imaging light.

The embodiment of the probe 500 shown in FIG. 5a is structurally configured such that both acoustic and optical imaging sensors can be combined for viewing without components such as the mirror 404 of FIG. 4b or prism 397 of FIG. 4c. The head section of probe 500 containing piezoelectric material 402 for the acoustic sensor and the conductive layers 401 on either side of the piezoelectric material 402 is aligned along the longitudinal axis of the fiber optic 403 and the probe is configured so that both acoustic and optical signals are emitted axially relative to the fiber axis, not perpendicular as in FIG. 4a.

Figure 5D:
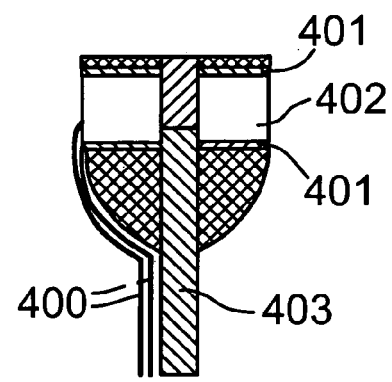
Figure 5B:
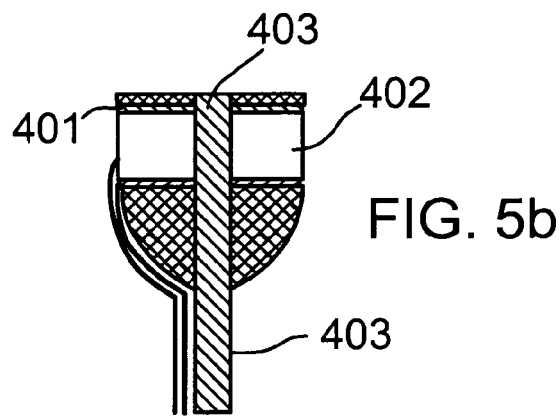
Figure 5E:
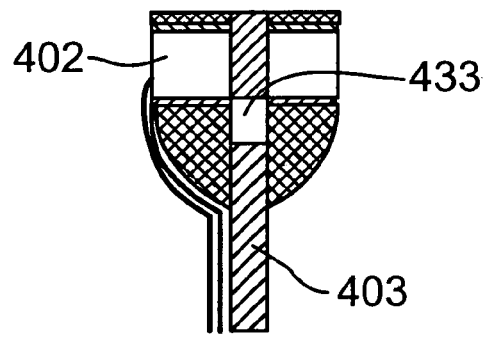
Figure 5C:
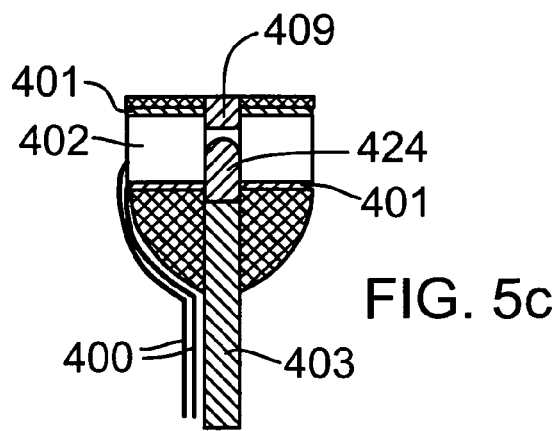
Figure 5F:
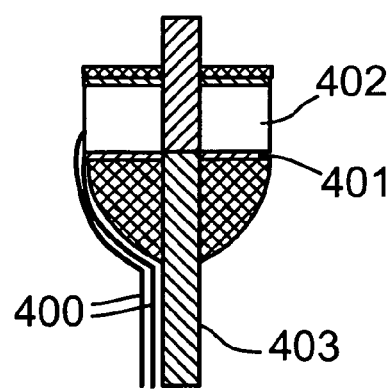

The embodiment shown in FIG. 5b is analogous to the embodiment shown in FIGS. 4b and 4c. FIG. 5c is analogous to the embodiment shown in FIG. 4d. The embodiment shown in FIG. 5d is analogous to the embodiment shown in FIG. 4e. The embodiment shown in FIG. 5e is analogous to the embodiments shown in FIGS. 4f and 4g. The embodiment shown in FIG. 5f is analogous to the embodiment shown in FIG. 4i.

Figure 6A:
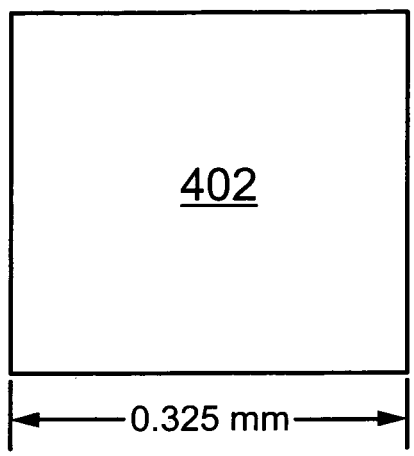
FIGS. 6a to 6c demonstrate representative acoustic transducer configurations, with FIG. 6a not having a hole in the transducer.
Figure 6B:
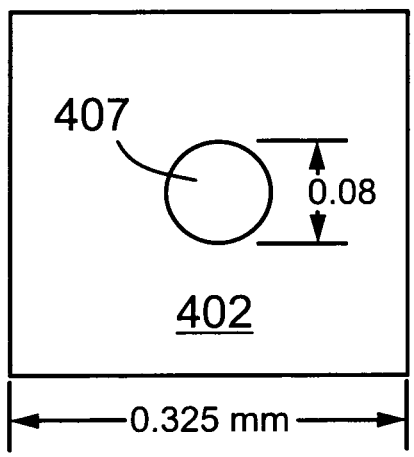

FIG. 6a shows the geometry of an emitting surface of a square transducer 402. It should be noted that the geometry of the emitting-surfaces of the acoustic transducers 402 are not limited to being in square in shape and may be any of several shapes, such as rectangular, circular, ellipsoid, and any other desirable shape. FIG. 6b shows a square transducer with the hole 407 in the center, while FIG. 6c shows a square transducer with a glass rod 501 in the hole 407.

Figure 6C:
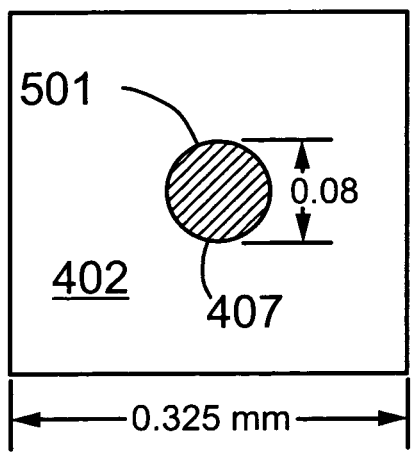
Figure 6D:
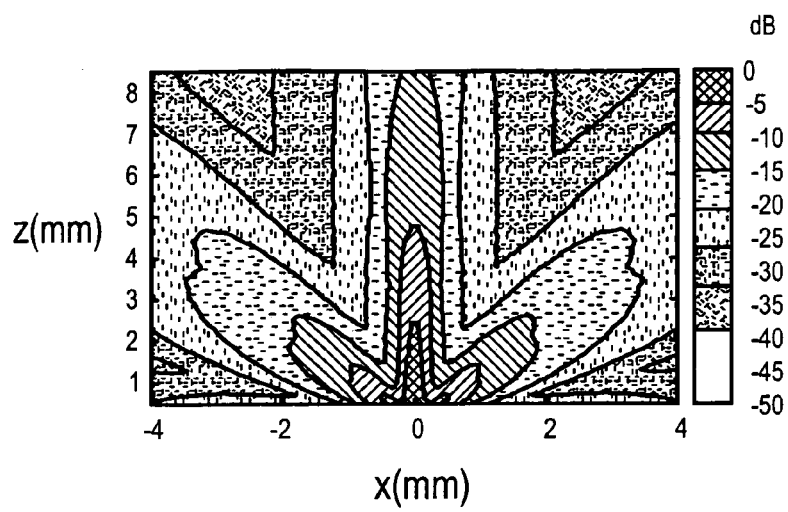
FIGS. 6d to 6f demonstrate representative simulation results of the effects of placing a hole through an ultrasound transducer on the acoustic beam pattern produced by the ultrasound transducer with FIG. 6d not having a hole.
Figure 6E:
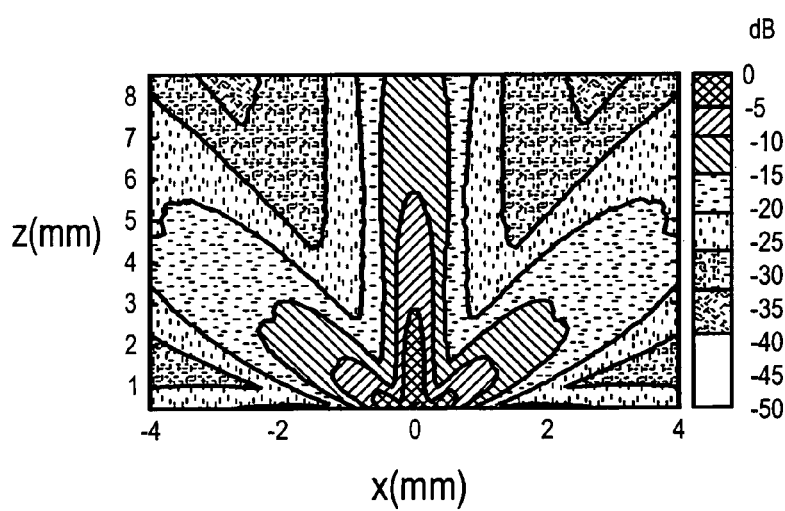
Figure 6F:
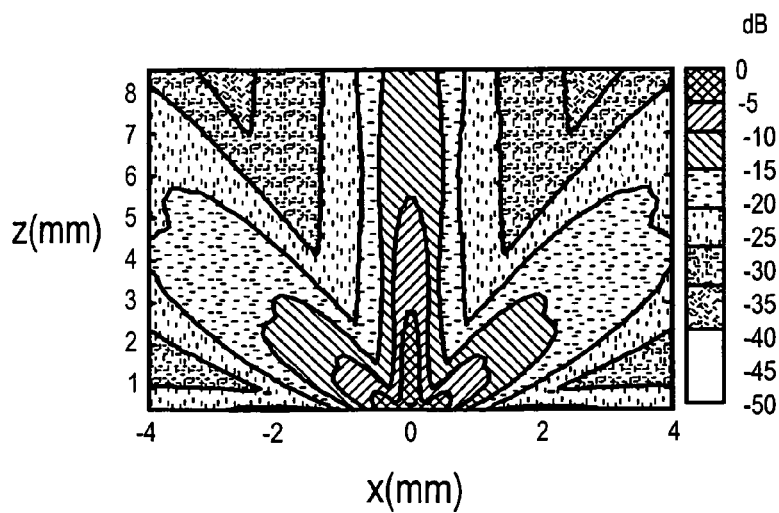

Results of a simulated beam profile using acoustic beam simulation software are shown in FIGS. 6d through 6f, corresponding to the transducer geometries in FIG. 6a through 6c respectively. As can be seen, there is considerable similarity in the beam profiles of the various configurations, providing evidence that ultrasound transducers adapted to allow a channel for optical transmission are capable of producing an acceptable ultrasound beam profile suitable for imaging purposes.

A simpler method for aligning the optical and acoustic imaging means would be to place the fiber optic adjacent to the surface of the acoustic transducer 402 without going through the transducer 402 itself. FIG. 7A shows an imaging probe 510 comprised of an acoustic transducer 402 with the distal end of an optical imaging circuit 428 placed on top of the acoustic transducer 402. The distal end portion of the optical imaging circuit 428 comprises the distal end of fiber 403 and any optical components, such as an optical spacer 433, a lens, such as a GRIN lens 405, mirror 404 or prism 397, that enable emission or collection of optical imaging energy. The distal end of an optical imaging circuit 428 can be affixed directly to the acoustic transducer 402 or supported by a support next to the acoustic transducer 402. The distal end of optical imaging circuit 428 would affect acoustic signals generated and/or received by the acoustic transducer 402 as it lies directly in the path of a portion of the acoustic beam emitted by transducer 402. However, a significant portion of the energy of the acoustic beam would not travel through the optical imaging means 403 and therefore would remain relatively unaffected.

Furthermore, the signal processing means preferably includes signal subtraction methods for discarding the portion of the signal that represents the early time portion of an echo signal to cancel reflections from interfaces close to the acoustic transducer's surface.

FIG. 7b shows a perspective view of imaging probe 512 which is a modification of the system in FIG. 7a where the distal end of optical imaging circuit 428 is recessed into the surface of the transducer 402 thus rendering the recessed portion of the transducer non-functional, so that acoustic beams transmitted or sensed by the acoustic transducer 402 do not substantially propagate through the overlying imaging fiber 403. A top view of this embodiment is shown in FIG. 7c. The portion of the transducer 402 rendered non-functional can be rendered non-functional by either removing the portion of the transducer 402 that lies underneath the distal end of optical imaging circuit 428 as shown in FIG. 7b, or by electrically isolating the portion of the electrode underneath the optical imaging means. Removal may be done by several methods, including the use of a dicing saw to cut a channel through the transducer 402. Furthermore, removal of a channel makes it possible to consider recessing the distal portion of the optical imaging means within a channel.

FIG. 7c shows a top view of the emitting/receiving surface of the probe 510 shown in FIG. 7b surrounding the distal end of optical imaging circuit 428.

FIG. 7d shows an imaging probe 516 that employs a composite transducer for the acoustic imaging means. In this case the composite transducer is a transducer comprising more than one signal generating element, or pillars 520. The composite transducer in FIG. 7d comprises four pillars 520. The channels 522 in between the pillars 520 leave a channel 522 for one or more distal ends of optical imaging circuit 428 to be placed within the confines of the composite acoustic transducer. The distal end of an optical imaging circuit 428 need not necessarily be recessed within channels 522, and can alternatively rest on or above the surface of the acoustic transducer 402. Conducting connections 400 between the upper conducting surfaces of the pillars 520 allows for the pillars to be simultaneously activated. The channels 522 can be filled with a filler material, such as a polymer or epoxy, to increase the mechanical stability of the composite transducer, or to help affix the optical imaging means in place.

FIG. 7e shows a top view of the imaging probe 516 with the distal end of the optical imaging circuit 428 placed within the center of the pillars 520. Any of the implementations for the distal portion of the optical imaging circuit 428 (e.g. any combination of fiber optics, spacers, GRIN lenses, Ball lenses, air gaps, transparent windows), such as those shown in FIG. 4, can be used in the implementations described in FIGS. 7a to 7e.

As part of most mechanical scanning mechanisms for imaging, there is a predominant motion associated with the scanning mechanism that defines the geometric path through which the imaging beam will sweep. For example, in an imaging system that uses a rotary motion to scan a region, there will typically be a circular or conical surface, through which the imaging beam sweeps, with the circular or conical surface being centered approximately on the axis of rotation, as occurs in current implementations of mechanical scanning intravascular ultrasound. The predominant motion in this case is the rotational motion.

Alternatively, if the imaging emitter/receiver is translated along the longitudinal axis, then the imaging beam will sweep through a planar surface and the plane defined by that surface will include the axis of translation. This predominant motion in this case is a longitudinal translation.

If the imaging emitter/receiver is simultaneously rotated around a longitudinal axis of a probe and translated along a path that is generally parallel to the longitudinal axis of the probe, then the imaging beam will sweep through a surface defined by a helicoid geometry.

It is possible to generate co-registered images with good precision from multiple acoustic and/or optical imaging means without having to have the two or more imaging beams be simultaneously collinear. This can be accomplished by having one or more imaging beams follow the path of a leading beam. Software or electronic circuitry can use knowledge of the speed and direction of the scanning mechanism's motions over time to then register the images generated from one of the imaging means onto one another.

For example, if the path of one imaging beam closely follows the path of another imaging beam (the leading beam) in a short time period, then it is possible to assume that the region scanned by the two means is similar enough to accurately co-register the two images with each other. The accuracy of the registration between the two images can be affected by the time delay in which the second beam follows the first beam. If the time delay is relatively small, then inaccuracies in the co-registration of the two images that could potentially develop in that time period are likely to be minimal. Such inaccuracies might include those caused by tissue motion (such as that induced by cardiac or respiratory motion), unintentional probe motion, physiologic changes such as blood flow and imprecision in the fidelity of the scanning mechanism. The time delay (which itself can vary over time) can be used for the process of registering the different images.

FIG. 8a shows an example of an imaging assembly 530 that contains both an acoustic imaging means and an optical imaging means. The predominant scanning motion is a rotational motion around a longitudinal axis that lies along the length of the imaging probe. As illustrated, the acoustic imaging beam 532 and optical imaging beam 534 sweep through a path that is circular in nature. If the imaging beams are not aligned normal to the longitudinal axis, but rather at an angle other than 90 degrees from the longitudinal axis, than the path through which the imaging beams sweep will be conical in nature. If a longitudinal translation were to be applied in combination with the rotary motion, the two beams would follow a roughly helicoid path.

It will be understood that the in all embodiments disclosed herein the imaging assembly may be translationally movable within the hollow shaft and may emit anywhere along its length and is not restricted to the distal end of the hollow shaft.

FIG. 8b shows a side view of the combined imaging probe 530 where the acoustic beam 532 travels in one direction (upwards in the diagram) and the optical imaging beam 534 travels out of the page (towards the reader). In this case, the optical beam 534 and acoustic beam 532 at any instant are oriented 90 degrees apart from each other.

FIGS. 8c through 8e represent a time series of the rotational motion of the imaging probe 530 as it would appear from the distal end of the imaging probe. In this example, the optical imaging beam 534 leads the acoustic imaging beam 532 by 90 degrees of rotation. At a constant frame rate of 30 frames per second, the time delay that it would take for the trailing beam to become collinear with a prior position of the leading beam would under 9 milliseconds, which is a short period of time with respect to artifacts that might occur due to cardiac motion experienced by an intravascular catheter.

Given the importance of miniaturizing the space occupied by components and assemblies in minimally invasive imaging means, it may be desirable to recess some of the components. For example, as seen in FIG. 9a, an imaging probe 540 has been configured to recess the distal end of the optical imaging circuit 428 into the backing 435 of the acoustic transducer 402. Recessing may not only accomplish efficiency of space use, but it may also provide a method of fixing the distal end of an optical imaging circuit 428 to the acoustic transducer 402.

The purpose of the backing material 435 on the acoustic transducer 402 is to attenuate signals generated from the back surface of the piezoelectric 402 so that an image is not formed by the energy that is emitted from the back surface of acoustic transducer 402 on which the optical emitter/receiver 403 is located, but rather only from the primary emitting surface for acoustic signals (top surface) of the transducer 402. Recessing an optical or other component in the backing material 435 may potentially cause the optical or other component to reflect signals back to the acoustic transducer 402 that would potentially create imaging artifacts.

FIG. 9b shows a deflecting surface 544 in which the optical emitter/receiver 403 is cradled that acts to deflect acoustic energy that might otherwise reach the optical emitter/receiver 403 and deflects that energy laterally (substantially parallel to the surface of the acoustic transducer 402) to minimize the amount of energy that is reflected back towards the transducer 402. This deflecting surface 544 may be made of a hard substance such as glass or steel.

FIG. 9c shows an implementation where the distal end of an optical imaging circuit 428 itself has a surface 545 that substantially deflects acoustic energy laterally without the need of an additional deflecting material as seen in FIG. 9b.

For embodiments of imaging probes where the imaging beams scan as a result of rotational motion, it is not necessary that the rotational velocity be a constant or even remains in the same direction. It is possible to have a reciprocating motion where the imaging assembly rotates in one direction and then stops and rotates in the opposite direction. In this situation, the leading and trailing beams swap roles with each other.

Figure 10A:
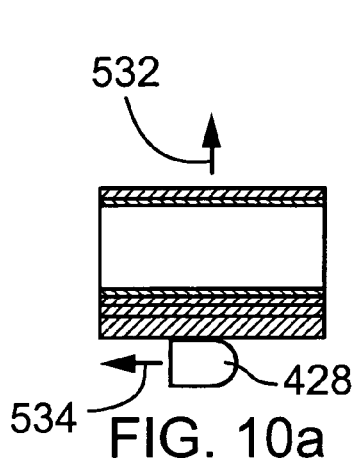
FIGS. 10a to 10e are similar to FIGS. 8b to 8e showing the imaging assembly being rotated in a reciprocating fashion rather than in a single rotational direction.
Figure 10B:
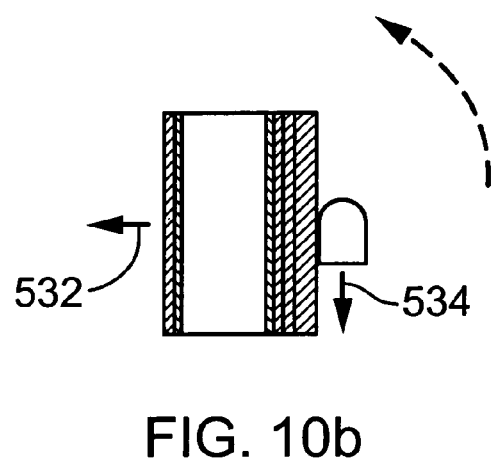
Figure 10C:
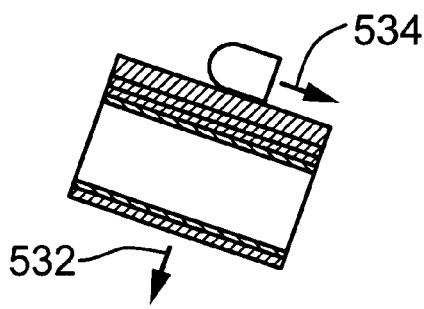
Figure 10D:
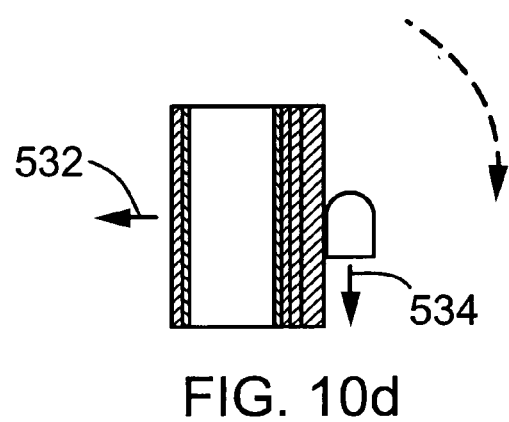
Figure 10E:
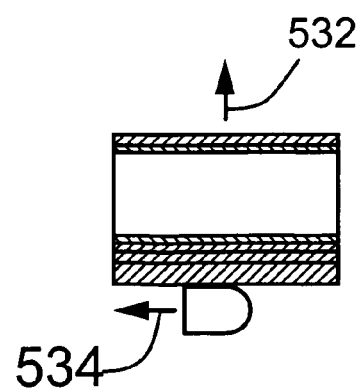

For example, in FIG. 10a, the acoustic beam 532 initially follows the optical beam 534 as the imaging assembly rotates in a counter clockwise direction. The acoustic beam 532 continues to follow the sweep path of the optical beam 534 as shown in FIG. 10b until the rotational velocity of the imaging probe reaches zero, (as in FIG. 10c). Once the direction of rotation changes to the opposite direction, the acoustic beam 532 becomes the leading beam and the optical beam follows (as in FIGS. 10d and 10e). The motion can change direction as many times as desired with a concomitant change in the definition of the leading and trailing sensor beams.

Figure 11:
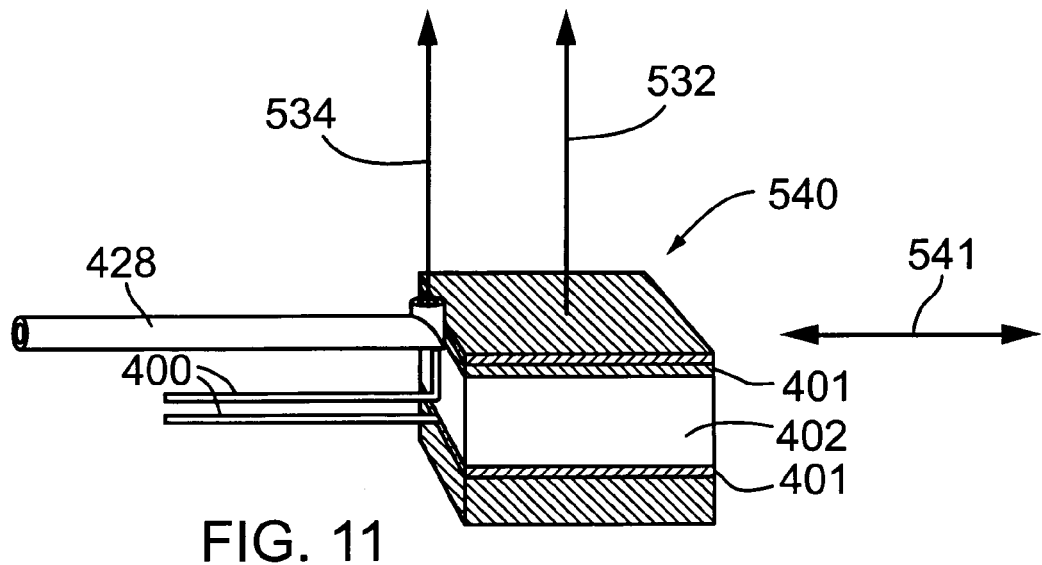
FIG. 11 shows a perspective view of an imaging probe where the predominant motion is a longitudinal motion where the surface swept by the optical beam and the acoustic beam are two co-planar rectangles.

FIG. 11 shows an imaging probe 540 where the predominant motion is a longitudinal motion back and forth along arrow 541 where the surface swept the optical beam 534 and the acoustic beam 532 are two co-planar rectangles. As the imaging assembly is translated proximally (to the left in FIG. 11) the optical imaging beam 534 leads the acoustic imaging beam 532. The opposite is true for distal translation (to the right in FIG. 11). The longitudinal motion can be reciprocated as well.

With either longitudinal or rotational predominant motions, it is understood that additional motions can be combined with the predominant motion. For example, a slow translation (such as 10 mm/s or less, and typically 1 mm/s or less) can be added to a rapid rotational scanning motion (such as 360 degrees per second or more and typically 3600 degrees per second or more) in order to acquire 2D cross-sectional images at different longitudinal positions.

Similarly, a slow rotational motion (e.g. less than 360 degrees per second and typically less than 30 degrees per second) can be added to a sequence of rapidly reciprocating longitudinal motions (averaging over 0.1 mm/s and more typically more than 1 mm/s) to create a series of longitudinal images acquired at different orientations around the longitudinal axis of the imaging probe. The alignment of the various imaging elements at the distal end is configured such that the one of the imaging beams will follow the other during the predominant motion, but the ability to accurately register the images on top of each other would not be significantly affected by the addition of a relative slow secondary motion. While absolute numbers for slow and rapid motions in the rotational and translation motions are provided above, it is the relative magnitude of these motions that is more important.

Figure 12:
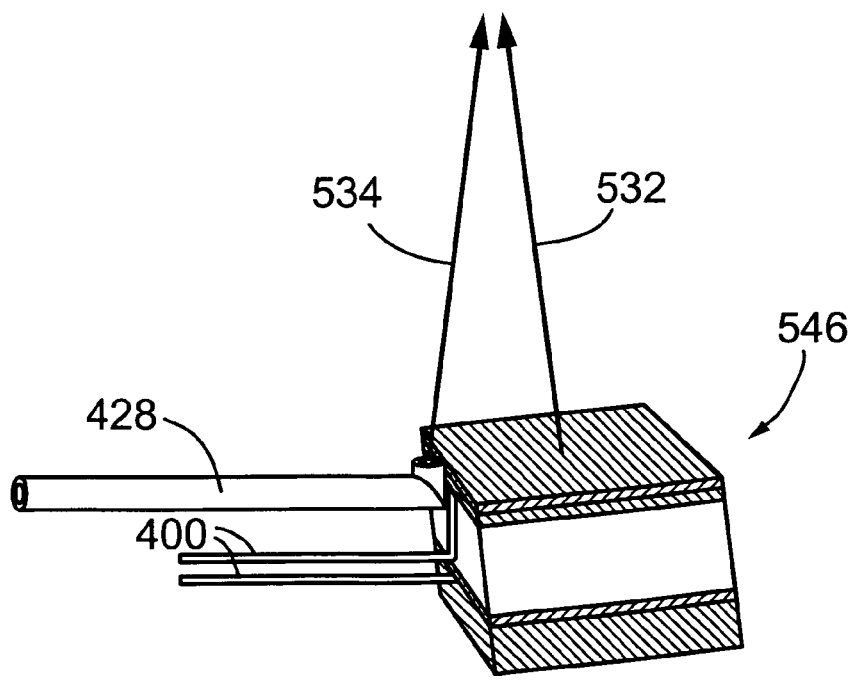
FIG. 12 shows a perspective view of an embodiment of an imaging probe where the optical imaging system is configured such that the optical imaging beams are angled such that these imaging beams substantially converge or overlap.

Collinear alignment of the optical and acoustic beams (as shown in the embodiments shown from FIGS. 4a to 5f) provide very accurate registration of the optical and acoustic images. An alternative embodiment of the probe is configured to have the optical and acoustic beams substantially overlap each other by angling either the optical imaging emitters/receivers towards the path of the acoustic beam or by angling the acoustic imaging emitter towards the path of the optical imaging beam. FIG. 12 shows such an embodiment of an imaging probe 546 where the distal end of an optical imaging circuit 428 is configured such that the optical imaging beam 534 is angled towards the acoustic imaging beam 532 and vice versa. This provides a simpler method of construction than aligning the optical and imaging beams as seen in FIGS. 4a to 5f, but allows the two imaging means to provide what may be a reasonably precise overlap over a portion of the two imaging beams. In particular, embodiments whereby the beams are aligned such that they overlap over a substantial portion of their focal ranges would be useful.

Figure 13:
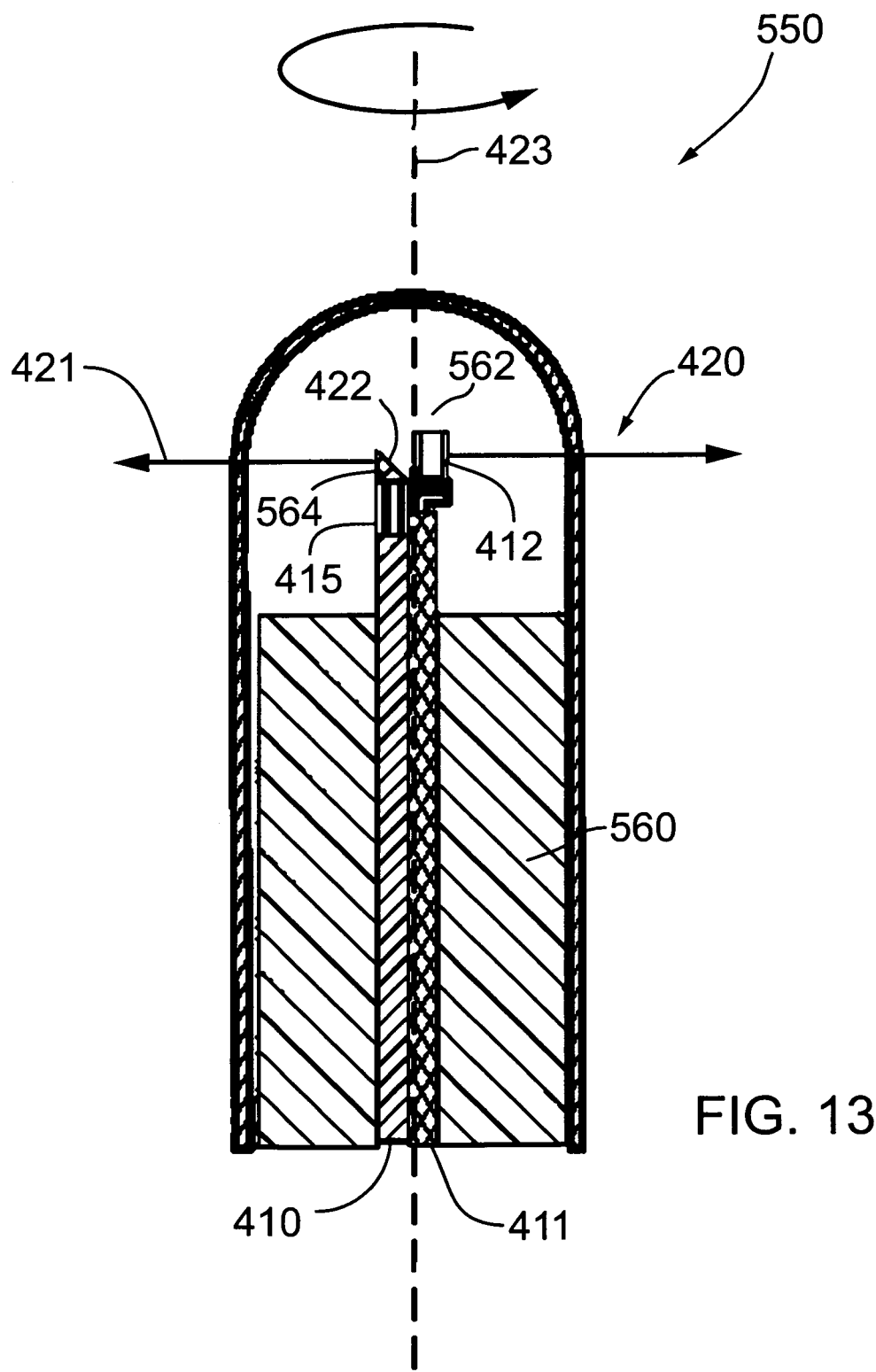
FIG. 13 is a cross sectional view of an imaging assembly suitable for side viewing with both acoustic and optical imaging.

FIG. 13 shows an embodiment of the imaging probe 550 configured to image simultaneously in the same general orientation and from the same general origin with both acoustic and optical means. At least one fiber optic 410 and one electrical conduit 411, such as a pair of coaxial conductors, reside within the imaging conduit 560 and travel to the imaging assembly 562. The imaging assembly 562 comprises an acoustic transducer 412 configured for imaging in a substantially side-viewing direction indicated by arrow 420. The imaging assembly 562 also includes distal end of an optical imaging circuit 564 configured for imaging in a substantially side-viewing direction indicated by arrow 421.

The acoustic transducer 412 and distal end of an optical imaging circuit 564 are configured such that they allow imaging in two or more separate directions at any instant within the same cross-sectional plane that is substantially perpendicular to the axis 423 around which the imaging assembly 562 rotates. Thus, assuming minimal translation of the imaging assembly 562 while the imaging assembly is rotated, the imaging data collected by the optical emitters/receivers 564 can be co-registered with the imaging data collected by the acoustic transducer 412. For example, if the acoustic and optical means are configured to image in directions that are 180 degrees opposite of each other around the longitudinal axis, as shown in FIG. 13, then the region imaged by the acoustic transducer 412 at one point in time will be substantially the same region that is imaged by the distal end of an optical imaging circuit 564 after the imaging assembly 562 has been rotated by half a revolution. Similarly, if the imaging beams 420 and 421 have a similar angle from the longitudinal axis other than 180 degrees, they will both sweep through paths of substantially coincident cones, and can therefore be co-registered.

Figures 14A, 14B:
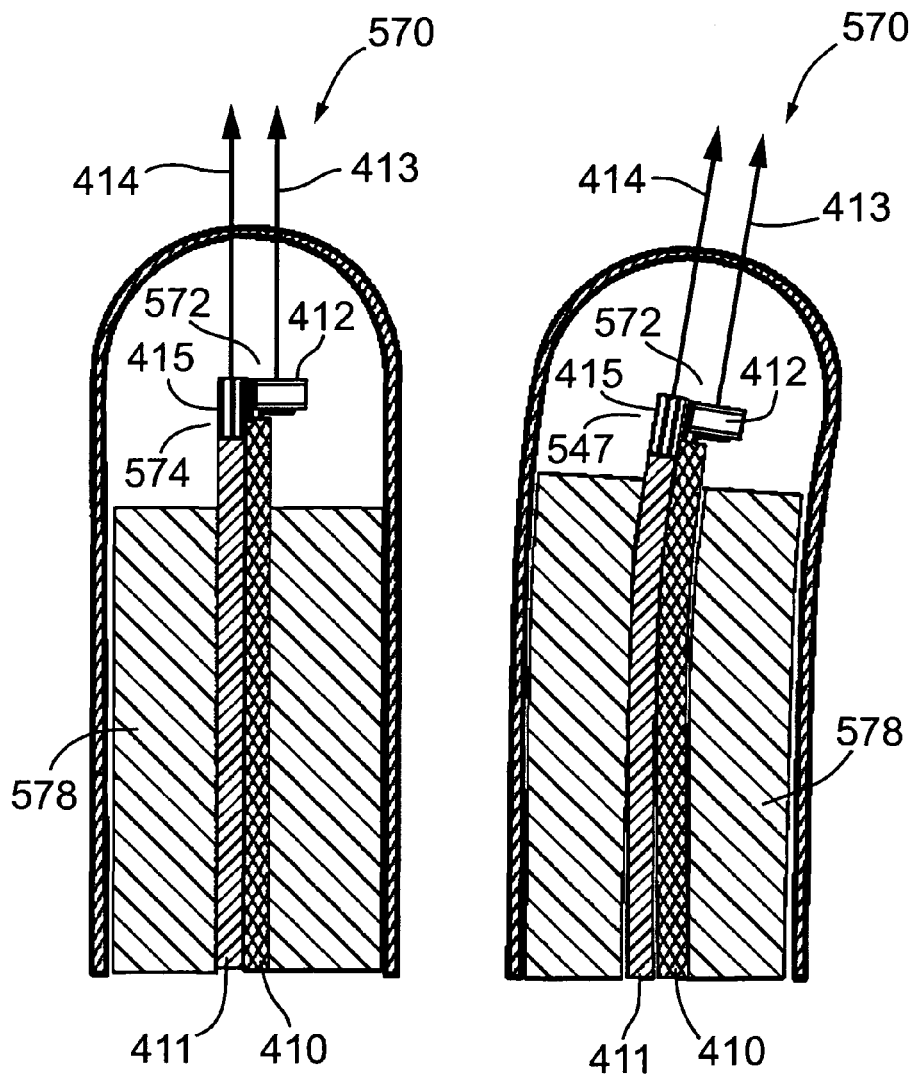
FIG. 14a is a cross sectional view of an imaging assembly suitable for forward viewing with both acoustic and optical imaging.
FIG. 14b is a cross sectional view of an imaging assembly suitable for forward viewing with both acoustic and optical imaging in which an artificial muscle polymer can be used to deform the distal region of the imaging probe.

The embodiment of the probe 570 shown in FIGS. 14a and 14b is configured such that both IVUS and OCT can be combined for forward viewing with a deformable component. At least one fiber optic 410 and one electrical conduit 411, such as a pair of coaxial conductors reside within the imaging conduit 578 and travels to the imaging assembly 572. The acoustic transducer 412 is configured for imaging in a substantially forward-looking direction indicated by arrow 413. A distal end of an optical imaging circuit 574 is configured for imaging in a substantially forward-looking direction indicated by arrow 414.

The distal end of an optical imaging circuit 574 typically comprises a distal end of a fiber optic 410 combined with a lens 415, such as a GRIN lens and an optional spacer (not shown). The imaging conduit 578 comprises an artificial muscle actuator that has the property of being able to deform upon the application of an electrical charge. FIG. 14b illustrates how the imaging angle would be changed if an artificial muscle actuator achieved a deformation while FIG. 14a shows the shape of the probe without application of a voltage to actuator.

Embodiments of the present imaging probe may be configured to make use of a deflector to allow for a larger transducer to be used within the imaging probe. Alternatively, the deflector may be pivotable and coupled to a pivoting mechanism to enable an additional degree of freedom in the scanning mechanism. For example, the scanning mechanism may facilitate 2D imaging, or may augment a 2D imaging system into a 3D imaging system. Alternatively, the deflector may be translated along the longitudinal axis in order to change the focal depth of the imaging system.

Figure 15A:
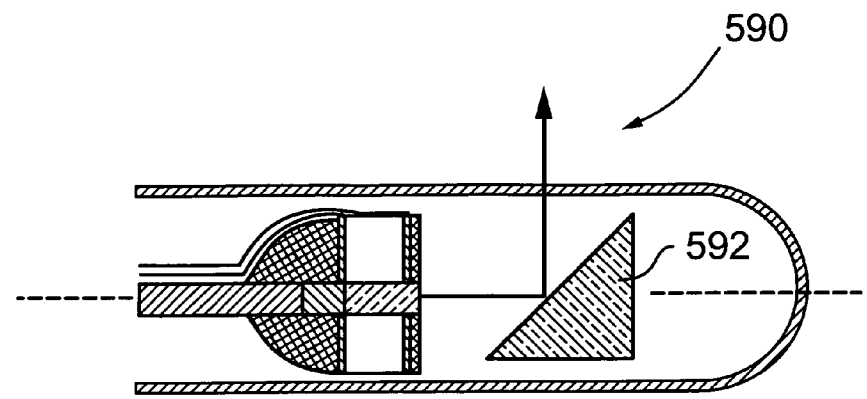
FIG. 15a is a cross sectional view of an imaging assembly suitable for side viewing with both acoustic and optical imaging using a reflective component to direct the optical and acoustic beams in the sideways direction.

FIG. 15a illustrates an embodiment of an imaging assembly 590 that comprises a deflector 592 used to deflect optical and/or acoustic imaging energy into a generally radial direction. The deflector 592 is made of one or more reflective materials. Optically reflective materials include polished or sputtered metals, such as stainless steel, gold, silver and platinum.

Figure 15B:
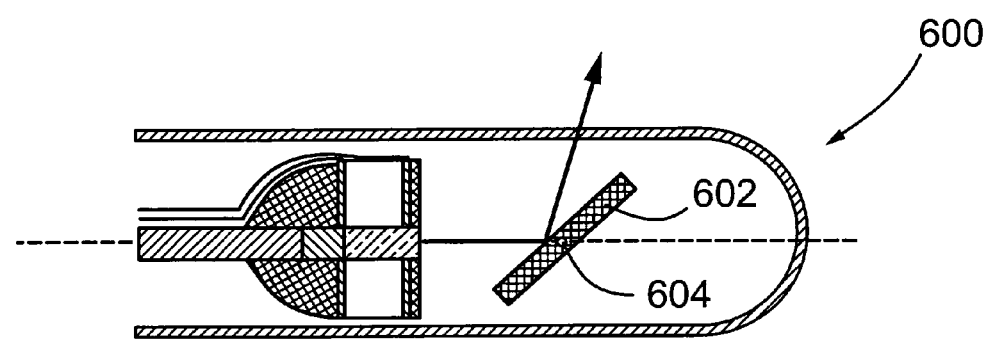
FIGS. 15b and 15c are similar to FIG. 15a but in which the reflective component is mounted about a pivot point so the optical and acoustic beams can be scanned in the sideways direction at a variable angle.

Acoustically reflective materials include stainless steel and other metals, quartz and other crystals, glass and hard polymers. FIG. 15b shows another embodiment of an imaging assembly 600 which comprises a deflector 602 that pivots around a pivot point 604 and thus allows the angle between the imaging beam and the longitudinal axis of the imaging probe to vary. The imaging assembly 600 may be configured so that deflector 602 can change position by being coupled to a variety of mechanisms, including mechanisms which utilize centripetal motion, magnetic forces, cable mechanisms, rheologic forces, piezoelectric drivers, miniaturized motors and others.

Figure 15C:
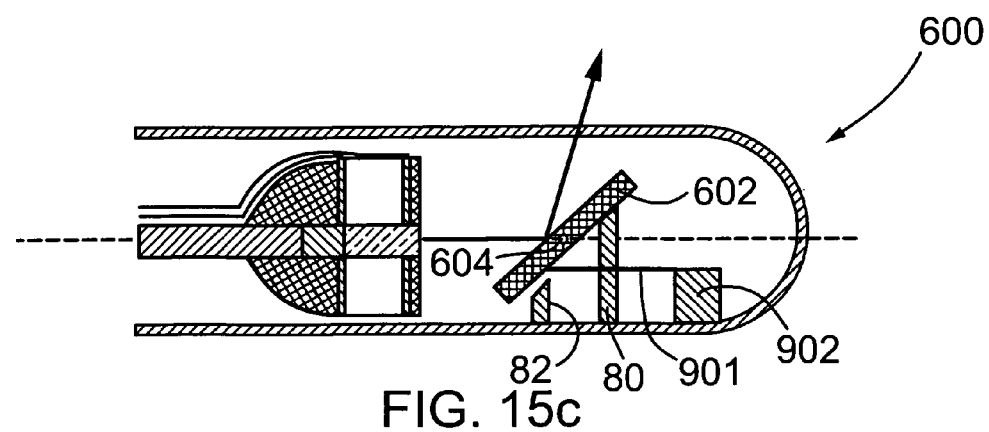

FIG. 15c illustrates an embodiment of the arrangement in FIG. 15b wherein a cantilever 901 mounted on a cantilever mount 902 and the deflector's range of motion is limited by a minimum stop 82 and a maximum stop 80. This embodiment has the property of having the imaging angle change as a result of changes in the rotational motion of the imaging assembly around the longitudinal axis of the probe. At rest or low rotational speeds, the cantilever wire forces the deflector 602 around its pivot point such that it comes into contact with stop 80. At higher rotational speeds, centripetal acceleration causes the deflector 604 to pivot away from stop 80. As centripetal acceleration continues to overpower the restoring force exerted by cantilever 901 on deflector 602, the deflector eventually comes into contact with stop 82. In such an embodiment, an imaging assembly 600 with a 3D scanning mechanism is implemented.

Figure 16A:
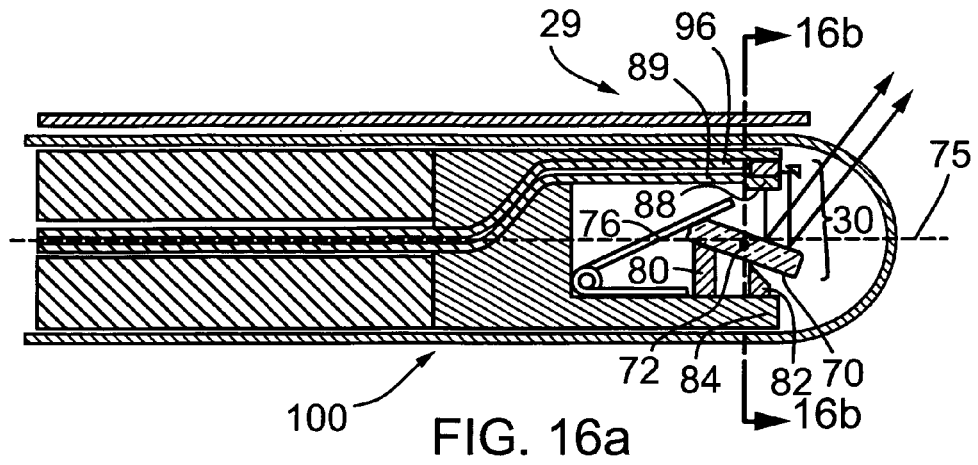
FIG. 16a is a cross section of an embodiment of an imaging probe using a tiltable component where the tilting action is modulated by centripetal acceleration due to the rotational motion of the imaging assembly around the longitudinal axis.
Figure 16B:
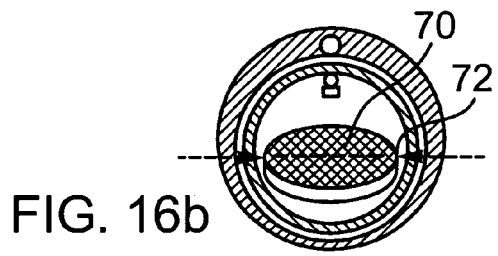

FIG. 16a illustrates an embodiment of the distal portion of an imaging probe 100 capable of both acoustic and optical imaging in a generally forward-looking direction. FIG. 16a shows an embodiment of a distal end 29 of an imaging probe containing an imaging assembly 30 that includes a tiltable component 70 where the tiltable component is a disc mounted on a pivoting mechanism such as a pin 72 that extends through the disc 70. The pivoting mechanism 72 defines the tilting axis of the tiltable disc 70. When the imaging assembly 30 is at rest, the disc 70 will remain in an arbitrary starting position. However, as the imaging assembly 30 rotates, the disc 70 will align itself such that the normal of the planes defined by the faces of the disc 70 are substantially parallel with the longitudinal axis 75. The disc 70 has two preferred orientations when the imaging assembly 30 is rotated, that are separated by a rotation around the tilting axis of 180 degrees.

For the purposes of this description, the tilt angle will be referred to as the angle between the longitudinal axis 75 and an imaginary axis through the tiltable component 70 that is parallel to the longitudinal 75 axis when the tiltable component 70 is in one of its preferred orientations. By way of example, when the tiltable component 70 is in a preferred orientation, the tilt angle is approximately zero. If the tiltable component 70 is tilted away from its preferred orientation by an external force, such as gravity, magnetic forces, electrostatic forces, friction with another moving part or fluid, compressive forces, normal forces or any other source of incompletely opposed torque on the tiltable component 70 around the tilt axis, the tilt angle will increase.

Figure 16C:
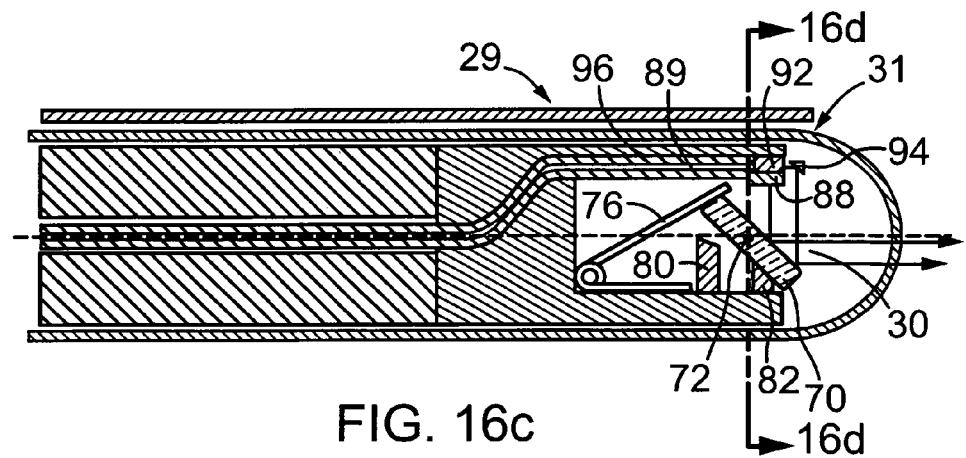
FIG. 16c is a cross section of the imaging probe of FIG. 16a but with the tiltable component at a different angle during use.
Figure 16D:
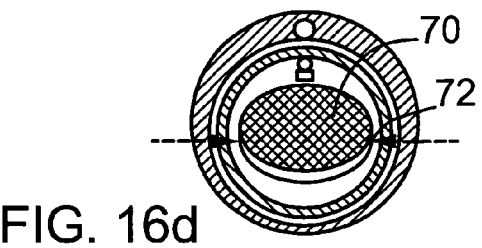
FIG. 16d is a view along the line 16d-16d of FIG. 16c.

One or more mechanisms may be included in the imaging assembly 30 that tends to cause the tiltable component 70 to have its tilting angle increase. For the purposes of this invention, such a mechanism is referred to as a restoring mechanism. A torsion spring 76 (as shown in FIGS. 16a and 16c), a cantilever or a compression spring can be used as a restoring mechanism, where one end of the spring 76 is mechanically in contact with tiltable component 70 and the other end is mechanically in contact with another part of the imaging probe 100, such as the body of the imaging assembly 30.

Alternatively, magnetic, electrostatic, hydraulic or other mechanisms that apply a torque on the tiltable component around the tilting axis could be applied. Other examples of mechanisms that could be used to provide a restoring force include tension from an elastomer (such as rubber, polyurethane, silicone, fluoroelastomers, thermoplastics and many others) or by use of a cantilever spring or foil, such as springs or foils made of platinum, nitinol, steel or other suitable materials. In very small embodiments of the imaging device, where intermolecular forces such as electrostatic forces and Van der Waals forces between components in the imaging assembly may become quite significant even without the application of an external voltage. Therefore, the innate intermolecular forces between the tiltable component and structures close to the tiltable component, such as the stops 80 and 82 described below, may be sufficient to provide a net restoring force. For example, a stop comprising a surface made of PVC, nylon or LDPE could provide sufficient attraction between the tiltable component and the stop.

One or more stops 80 and 82 may limit the range of the tilt angle of the tiltable component 70. For example, a post or lip 80 can extend from the shell 84 of the imaging assembly 30 as a stop to prevent the tilting component from further changing its tilt angle while it makes contact with the stop 80. Therefore, a stop can be used to limit the tilt angle from exceeding a maximum value determined by the position of the stop. In many embodiments, this maximum tilt angle is the tilt angle that is achieved when the imaging assembly 30 is at rest and at low rotational speeds.

An additional or alternative stop 82 can be included to create a minimum tilt angle that the tiltable component will achieve at rotational speeds in the upper end of the operating range. Indeed, there are many situations in which there is no significant benefit in allowing the tilt angle to reach zero, as will become apparent in the following descriptions of specific embodiments. FIG. 16c shows the tiltable component hitting the second stop to limit its range of motion at higher rotational speeds of the imaging assembly.

The imaging assembly may include both optical emitters and associated optics and ultrasound transducers. The ultrasound transducer 88 is mounted at the end of small coaxial cable 89 and lens 92 and mirror 94 are mounted at the end of a fiber optic cable 96 in the imaging assembly 30 in FIGS. 16a to 16d with the optical and ultrasonic emitters configured to focus imaging energy onto the tiltable component 70. The ultrasound transducer 88 and optical emitter can direct imaging energy towards the tiltable component 70. Alternatively, one of the embodiments that enables collinear optical and acoustic imaging, as seen in FIGS. 4a through 4k or FIGS. 5a through 5f can direct imaging energy towards the tiltable component 70.

The imaging energy is then deflected by an energy-deflecting component mounted on the tiltable component 70. For ultrasound imaging, the energy-deflecting component (the tiltable component 70) may comprise an acoustically reflective surface, such as a solid metal surface (e.g. stainless steel) or crystalline surface, such as quartz crystal or glass. For optical imaging, the energy deflecting component (tiltable component 70) can comprise an optically reflective surface such as a mirror surface made from polished metal, metallized polymer such as metallized biaxially oriented polyethylene terephthalate (Mylar), sputtered or electrochemically deposited metal or metal foil. Metals commonly used to make mirrors include aluminum, silver, steel, gold or chrome.

Alternatively, the energy-deflecting component could be made of a transparent refractive material, such as glass, clear polymers, and many others, and deflect the imaging energy in a manner similar to a prism. Preferably, the emitter and/or receiver is mounted on a component of the imaging assembly that rotates with the imaging assembly. However, it is also possible that the emitter and/or receiver is mounted on a component of the imaging probe that does not rotate with the imaging assembly while the energy deflecting mechanism within the imaging assembly does rotate. This could be achieved by mounting the emitter and/or receiver on an external sheath for example, or by having the imaging assembly divided into two or more sub-assemblies, one of which rotates and includes the tiltable component.

For ultrasound and optical coherence tomography, the ability to adjust the angle of propagation of the emitted and/or received imaging energy, when combined with the rotational motion of the imaging assembly, allows a 3D volume to be scanned. For angioscopy and infrared imaging, the ability to adjust the angle of propagation of the emitted and/or received imaging energy, when combined with the rotational motion of the imaging assembly, allows an image to be produced using a single fiber optic rather than requiring a bundle of fibers. Such an improvement can result in greater flexibility and/or miniaturization of the imaging device.

Further details of various scanning mechanisms that may be used in the imaging probe disclosed herein are disclosed in copending application Serial No. 12/020,206 entitled SCANNING MECHANISMS FOR IMAGING PROBE, filed concurrently herewith, which his incorporated herein by reference in its entirety.

In the case where the energy-deflecting component comprises a reflective surface it is not necessary that the reflective surface be planar. For example, in the case of acoustic imaging, it may be advantageous for an acoustically reflective surface to have a contour to it, such as a parabolic or spheroid contour, so that the acoustic beam can be focused by the reflective surface and improve lateral resolution of the acoustic imaging system as a result. Furthermore, in the case where the tilting component is used to deflect both acoustic and optical energy using reflection, the acoustic reflector need not be the same surface that reflects the optical energy.

For example, while it might be advantageous to have a contour such as a parabolic contour for the acoustically reflective surface, it may be preferable to have a planar surface for the redirection of the optical imaging energy. This can be accomplished by having an acoustically reflective surface such as a stainless steel disc with one of its faces contoured to have a parabolic shape to it as in FIGS. 17a through 17d which show a tiltable deflecting component that has an optically reflective surface that is distinct from the acoustically reflective surface.

FIG. 17a is a perspective drawing of a deflector that has holes on its side for receiving pins on which the deflector can pivot within an imaging assembly. FIG. 17b shows a cross-section through the deflector near the center of the deflector. The holes for receiving pins 465 are seen. The top layer is a flat, optically reflective layer 461. Under the optically reflective layer 461 is a generally acoustically transparent layer 462, which lies between the optically reflective layer 461 and an acoustically reflective substrate 463. FIGS. 17c and 17d show cross-sectional images of such a deflector at different points away from the center of the disc.

Such a deflector can be constructed by taking a disc of an acoustically reflective material such as stainless steel and drilling the necessary holes or indentations so that the deflector can eventually be mounted into an imaging assembly. A parabolic or spheroid indentation can be made into one face of the disc. The indented surface can then be filled with an acoustically transparent medium, such as polymethylpentene (TPX). A thin layer of gold, silver or chrome can be sputter deposited onto the exposed planar polymer surface to act as an optically reflective surface. Such a layer may be on the order of 300 Angstroms to 20,000 Angstroms such that it is thin enough that its mechanical properties to allow acoustic energy to transmit through it, while simultaneously providing an optically reflective surface.

The result of such a fabrication process is to create a layered reflector that reflects acoustic energy from the contoured surface to achieve the desired focusing effect, while the optical energy is reflected from a planar surface. It is a further advantage of this construct that the optical and acoustic imaging can occur in a configuration where the optical and acoustic imaging energy travels through the same general space, facilitating co-registration of optical and acoustic images and minimizing the amount of space required within the imaging assembly to accommodate more than one modality of imaging.

In some embodiments, such as the assembly shown in FIGS. 16a and 16c, it may be helpful to use one of the imaging modalities solely to measure a parameter useful for the reconstruction of 2D and 3D images. For example, in the case of a volumetric imaging probe that uses a deflectable component, it may be desirable to use OCT to accurately measure the tilt angle of the deflectable component. Thus, an ultrasound image could be generated with knowledge of the tilt angle derived from OCT data, such as the tilt angle of tiltable component 70 in FIG. 16a without necessarily using the OCT data to generate corresponding OCT images of the region outside of the imaging probe.

Figure 18A:
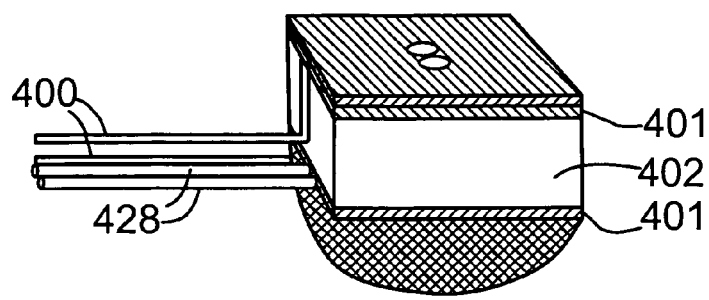
FIG. 18a is a perspective view of an ultrasound imaging transducer with two (2) optical imaging emitters/receivers through two (2) separate optically transmissive channels in the acoustic transducer.
Figure 18B:
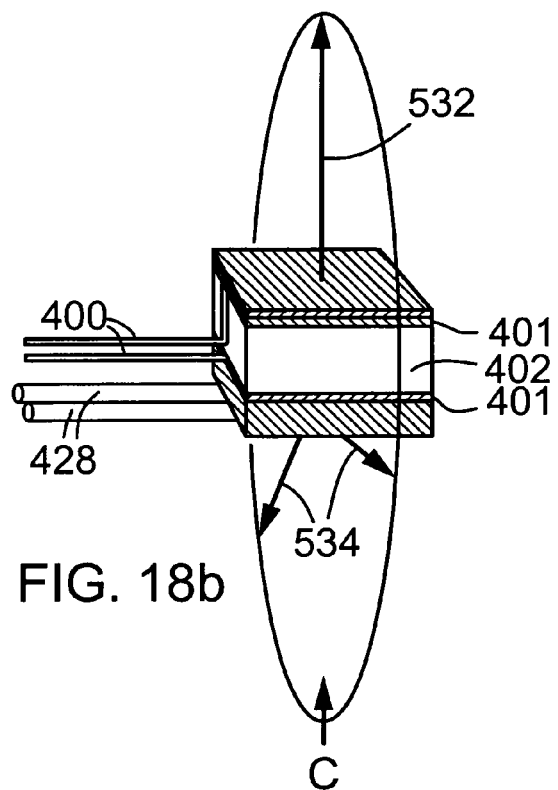
FIG. 18b is a perspective view of an embodiment of an imaging probe having an ultrasound imaging transducer with two (2) optical imaging emitters/receivers arranged in a manner such that they are aligned with the predominant rotary motion of the imaging assembly.
Figure 18C:
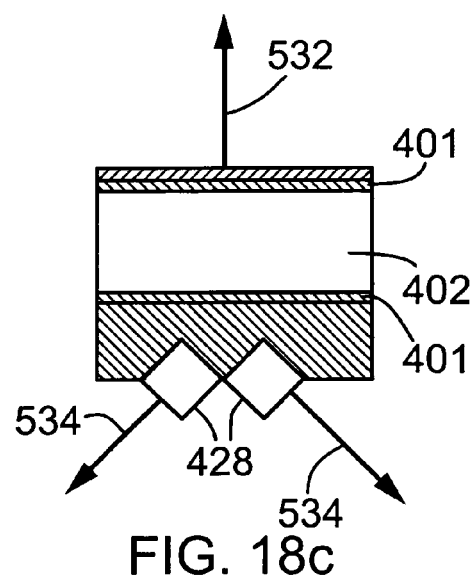
FIG. 18c is a view along arrow C of FIG. 18b.

In some embodiments, it will be desirable to have more than one method for optical imaging in an intravascular imaging system. For example, OCT and angioscopy may be a useful combination. FIG. 18a shows an ultrasound imaging transducer 402 with two (2) distal ends of optical imaging circuits 428 through two (2) separate optically transmissive channels in the acoustic transducer. FIGS. 18b and 18c show an acoustic imaging transducer with two (2) distal ends of optical imaging circuits 428 arranged in a manner such that they are aligned along the predominant rotary motion of the imaging assembly. These are examples of using more than one optical imaging emitter/receiver at the distal end of the imaging probe. If the imaging probe uses extensive rotary motion around its longitudinal axis as part of the scanning mechanism, such embodiments may require the use of a multi-channel optical rotary joint.

Alternatively, the optical imaging light sources and/or detectors for some of the imaging systems may be mounted on the rotary portion of the imaging probe and be coupled to the imaging system using electrical slip rings or wireless communication. A battery may optionally be used as a source of electrical energy on the rotary portion of the probe or adapter to minimize the number of slip rings required. Illuminating sources and photodetectors can be placed at the proximal end of the imaging probe and may be configured such that they rotate around the longitudinal axis of the probe with the rest of the imaging conduit 34 so that further optical couplers are not required between the imaging probe and the adapter. This is done because the complexity of rotary optical joints increases substantially if more than one fiber is involved to connect the probe to the rest of the system.

If the imaging probe uses only reciprocal rotary motion over a short range of angles (such as less then two full revolutions), or no rotary motion at all, then the use of an optical rotary joint is not necessary, simplifying the task of coupling the optical elements of the imaging probe to the image processing and display hardware.

The imaging probe may include a motion detector for detecting movement of the movable member (tiltable or bendable members) relative to a remainder of the imaging assembly. The motion detector may be based on any of optical coherence based detection means, reflection intensity detection means, and a strain gauge based detection means.

The pivotally mountable members may be pivotally mounted on a low friction pivot mechanism. The restoring mechanism is provided by any one or combination of a spring and a magnetic/elelctromagnetic assembly as discussed above. The restoring mechanism may also include a surface exhibiting electrostatic properties which interact with the movable member. It will be understood that the hollow shaft may be an external catheter sheath which may have memory properties.

All embodiments of the imaging probe disclosed herein may be fitted to existing control and image processing system and display systems to which the probe is connectable. The processing and display system would be configured to process the received energy signals and produce images of interior surfaces or adjacent structures of said bodily lumens and cavities or exterior surfaces or adjacent structures of a body.

Figure 19:
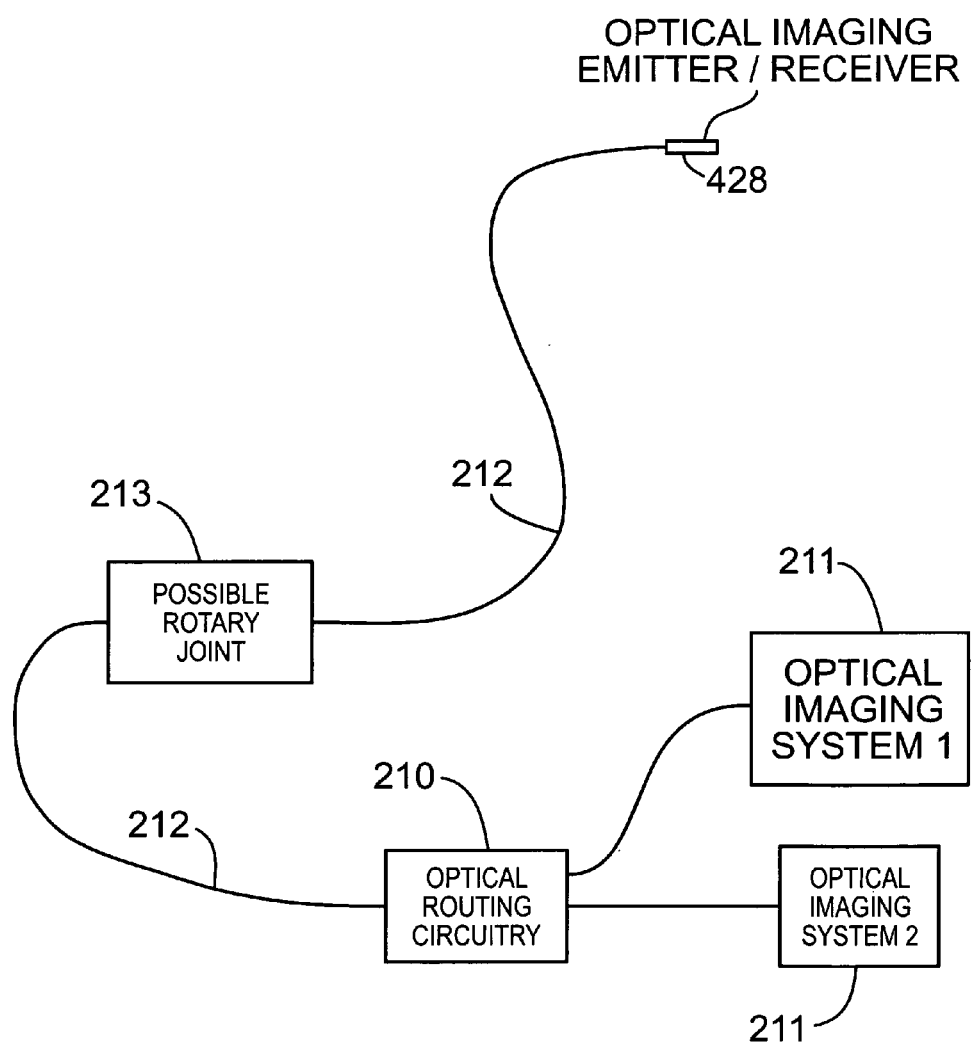
FIG. 19 is a schematic of a system where there are two optical imaging systems that are coupled to the same optical imaging waveguide via optical routing circuitry.

In another embodiment, it is possible to using the same optical imaging emitter/receiver at the distal end of the imaging probe and use optical routing circuitry such as switches, multiplexers, demultiplexers, prisms, diffraction gratings, couplers and/or circulators to use the same fiber and distal optical components for more than one imaging modality. FIG. 19 shows a schematic of a system where there are two (2) optical imaging systems 211 that are coupled to the same optical imaging waveguide 212 via optical routing circuitry (comprising one or more of the components listed above). The waveguide may be coupled to the imaging probe via an optical rotary joint 213 if the image probe 12 requires a large range of rotary motion as part of its scanning mechanism. The distal end of optical imaging circuit 428 may comprise any of the combinations of optical fiber, spacers, mirrors, prisms, ball lenses, GRIN lenses, air gaps and transparent windows mentioned elsewhere in the present invention to enable optical imaging. While many optical imaging elements, such as the waveguide and lenses, are designed to operate optimally for particular ranges of wavelengths (e.g. infrared vs visible spectrum), the performance of a fiber optic or other optical component designed for one range is often still adequate to provide information using light in the other spectrum.

Therefore, imaging using more than one range of wavelengths can occur simultaneously. Alternatively, the imaging waveguide can be used at different time intervals for different imaging modalities by means of optical switches, multiplexers and demultiplexers within the optical routing circuitry 210, or by simply timing the use of the optical waveguide at different time intervals for different imaging modalities.

While a fiber optic would be a preferred optical waveguide 212 for most embodiments, it may be desirable to use an alternative form of optical waveguide that is potentially more space efficient than an optical fiber. For example, a thin optical channel, on the order of 3 to 500 microns in maximal diameter and preferably on the order of 4 to 125 microns can be formed in a catheter at the time of extrusion. A fluid medium with a high index of refraction can be introduced into the optical channel, such as by means of injection. Such a fluid medium may include an epoxy or adhesive specifically designed for optical components.

The fluid medium may also be curable, such as in the case of UV curable adhesives. The creation of an optically transparent channel filled with a material with a high index of refraction surrounded by the extruded catheter material with a lower index of refraction would essentially replicate the functionality of including a fiber optic, but may allow for slightly more efficient use of space in the catheter by not requiring a separate cladding layer. The optimal use of space in a catheter is often important given their minimally invasive nature and the limited space available in the regions in which these catheters are deployed.

Yet another mode of operation for the present invention is the use of a transducer that combines acoustic transduction with an optical transducer where the transmitted energy is of one form and the received energy is of another. For example, photoacoustic imaging comprises delivery of light-based energy to an imaged region. The photons interact with the imaged region and create acoustic energy as part of their interaction with the medium in which they propagate. This acoustic energy is often in the form of ultrasound waves, and can be detected by an ultrasound transducer. It should be apparent that the use of an optical emitter aligned and in combination with an acoustic receiver would be a good configuration to enable photoacoustic imaging. An ultrasound transducer with an opening for optical imaging or that allows substantial overlap in the acoustic and optical imaging regions, such as those shown in FIGS. 4a through 4k, 5a through 5F or FIG. 12, would enable photoacoustic imaging.

Similarly, sonoluminescent imaging comprises delivery of ultrasound-based energy to an imaged region (Daniels and Price, Ultrasound in Medicine and Biology 1991:17(3):297-308). The acoustic energy interacts with the imaged region and creates photons as part of its interaction with the medium in which it propagates. Some of these photons are directed back toward the source of the acoustic energy. It should be apparent that the use of an ultrasound transducer aligned in combination with an optical receiver would be a good configuration to enable sonoluminescent imaging.

Implementations of acoustic and optical imaging elements where the imaging beams are collinear, or substantially overlap, such as those shown in FIGS. 4a through 4k, 5a through 5f or FIG. 12, would enable sonoluminescent imaging.

Referring to FIG. 1 again, imaging probe 12 (which may include any of the embodiments of the acoustic and optical sensors discussed herein) and its components may be of several dimensions and properties depending on the anatomic location and purpose of use for the imaging that is enabled by the imaging probe 12. For example, for the purposes of use in the cardiovascular system, including the cardiac chambers, the imaging probe 12 would preferably be elongate and flexible, with a length ranging from 5 to 3000 mm, preferably with a length ranging from 300 mm to 1600 mm. The imaging conduit 34 and imaging assembly 30 may have a maximum cross-sectional dimension ranging from 200 microns to 10 mm, preferably ranging from 500 microns to 5 mm. An external sheath 48 may surround both the imaging conduit 34 and imaging assembly 30. This would enable the imaging conduit 34 and imaging assembly 30 to rotate within the external sheath while mechanically isolating the rotational motion of these two components from the surrounding tissues.

In yet another example, the use of the imaging probe 10 in the gastrointestinal system would typically have the imaging probe 10 being elongate and flexible, with a length ranging from 100 mm to 2000 mm and preferably in the range of 300 mm to 1500 mm. The maximum cross-sectional dimension would typically range from 3 mm to 20 mm.

In yet another example, the use of the imaging probe 10 to image soft tissue via percutaneous means would have the imaging probe with a rigid shaft. The external sheath would be replaced by a rigid hollow shaft, such as a stainless steel tube although many other polymers, metals and even ceramics would be functionally suitable.

In yet another example, the use of the imaging probe 10 in the intraoperative neurosurgical setting would typically have the imaging probe 10 being short and semi-flexible, with a length ranging from 50 mm to 200 mm. It would be preferable that the surgeon can bend and shape the probe during the procedure to provide optimal passage from extra-cranial space towards the intracranial target being imaged. The maximum cross-sectional dimension would range from 200 microns to 5 mm and preferably from 500 microns to 3 mm.

In yet another example, the use of the imaging probe 10 in the interventional neurovascular setting would typically have the imaging probe 10 being long and ultraflexible, with a length ranging from 200 mm to 4000 mm and preferably ranging from 1300 mm to 2000 mm. The maximum cross-sectional dimension would range from 200 microns to 5 mm and preferably from 500 microns to 3 mm. The distal end of the probe would preferably possess shape memory to enhance navigation through the neurovasculature.

Embodiments of the present invention can be used in conjunction with or incorporated into devices that are used for intervention, such as those used for cardiovascular intervention, such as an angioplasty balloon, atherectomy device, stent delivery system or localized drug delivery system. It can also be used in conjuction with or incorporated into devices that facilitate biopsies, radio-frequency ablation, resection, cautery, localized brachytherapy, cryotherapy, laser ablation or acoustic ablation.

In particular, using the image scanning mechanism to direct higher powers of optical or acoustic energy to a targeted region can facilitate the use of the current device to enable laser or acoustic ablation of tissue. For example, while imaging a region of a blood vessel with an OCT or ultrasound embodiment of an imaging probe described in the present invention a region for the delivery of therapy can be selected through a user interface. Then, powerful pulses of energy can be delivered at times when the scanning mechanism is oriented to delivery energy in the desired direction. For example, pulses of laser energy can be transmitted down the same fiber optic used for optical imaging, be deflected by a deflecting component in those embodiments that include a deflecting component, and travel towards the targeted tissue for the desired effect. The timing of the pulses of laser energy is coordinated with the scanning pattern realized by the imaging probe to direct the energy towards the targeted region.

The opportunity to acquire accurately registered images of two or more high resolution imaging modalities provides significant information that is likely to be more useful than available by a single imaging modality. Maschke et al describe the formation of a composite image whereby the inner portion of an intravascular image is composed of OCT imaging information while the outer portion of an intravascular image is composed of IVUS imaging information. This takes advantage of the higher resolution images acquired by OCT and the higher penetration of IVUS. However, the reliability of this superposition of IVUS and OCT images is limited by the inaccuracy of the registration in the IVUS and OCT images that occurs using the arrangement of the IVUS and OCT imaging elements as described by Maschke and are substantially overcome by many of the embodiments in the present invention.

Figure 20A:
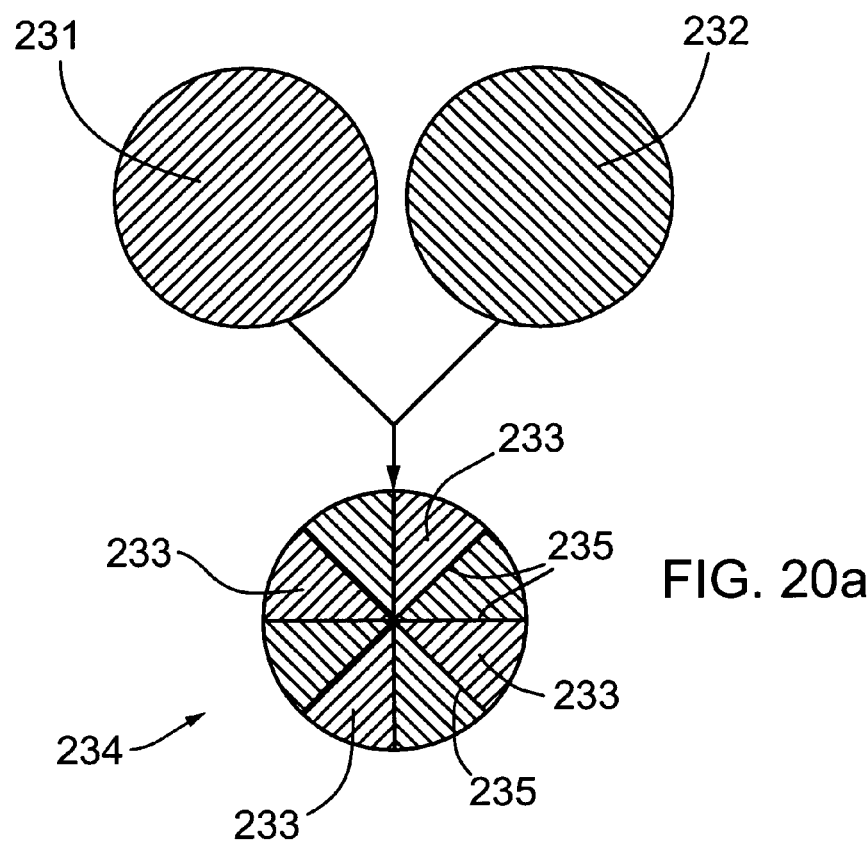
FIGS. 20a and 20b demonstrate sector-shaped patterns for simultaneously demonstrating portions of two (2) or more images that are co-registered with each other.
Figure 20B:
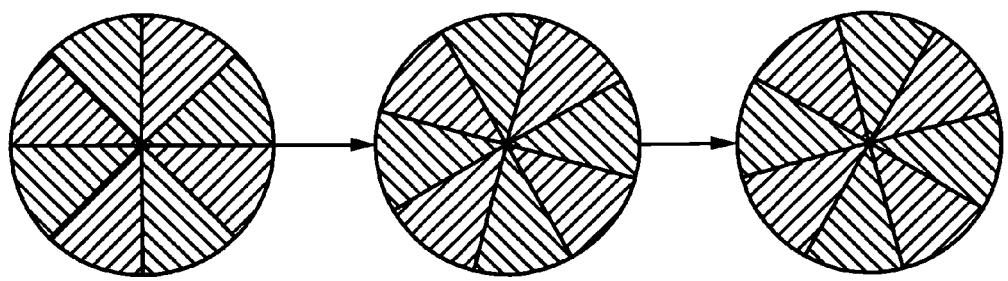

Alternative presentations of combined IVUS and OCT images might include dividing the image into sectors, where alternating sectors are displayed using alternating imaging means, as seen in FIG. 20*a*. First image 231 and second image 232, where the first and second images are co-registered with each other images and acquired by different means, can be used to form a combined image 234 where sectors 233 of the first image replace sectors of the second image. Optionally, the borders 235 defining the sectors 233 can rotate over time around the center of the image to provide a dynamic image for identifying features in both the first and second co-registered images. FIG. 20*b* shows a time progression of the rotations of the borders 235 around the center of the combined image 234.

Figure 21A:
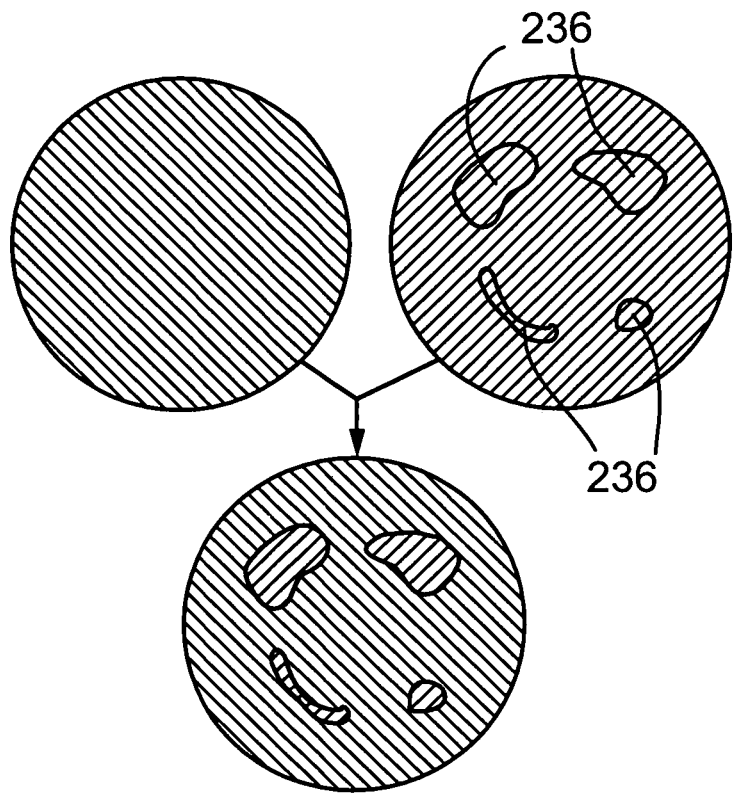
FIGS. 21a and 21b demonstrate arbitrary patterns for simultaneously showing portions of 2 or more images that are co-registered with each other.
Figure 21B:
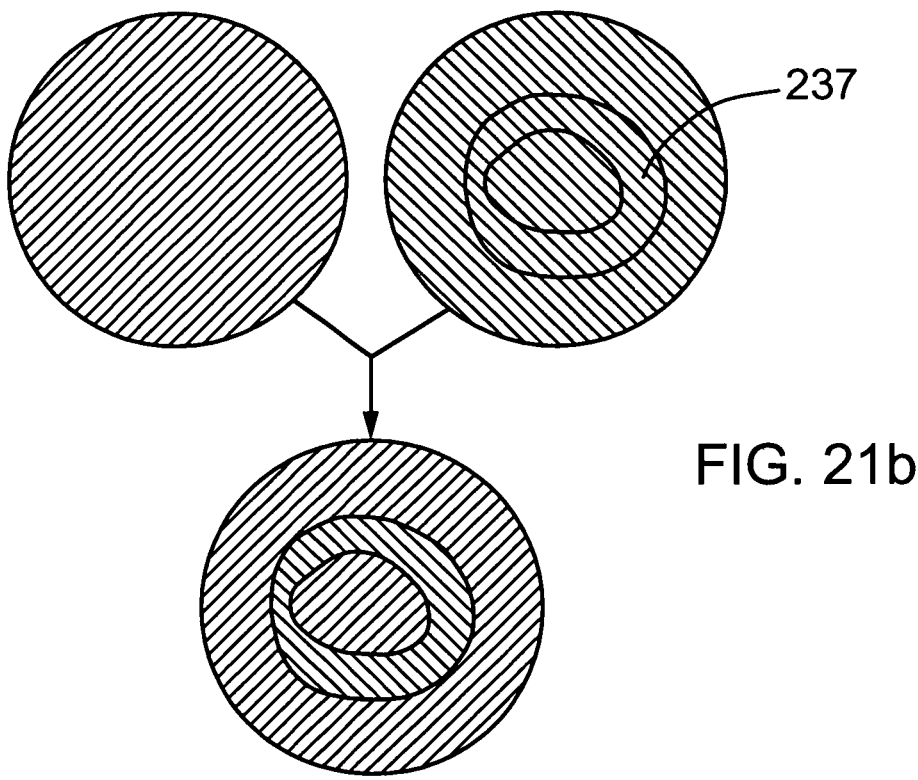

Alternatively, the user can specify which portions they would like to have as one image and which they would like to see as the other by identifying closed contours 236 in the second image as seen in FIG. 21*a* or by identifying a space 237 in between two closed contours in the second image, as seen in FIG. 21*b*.

Figure 22:
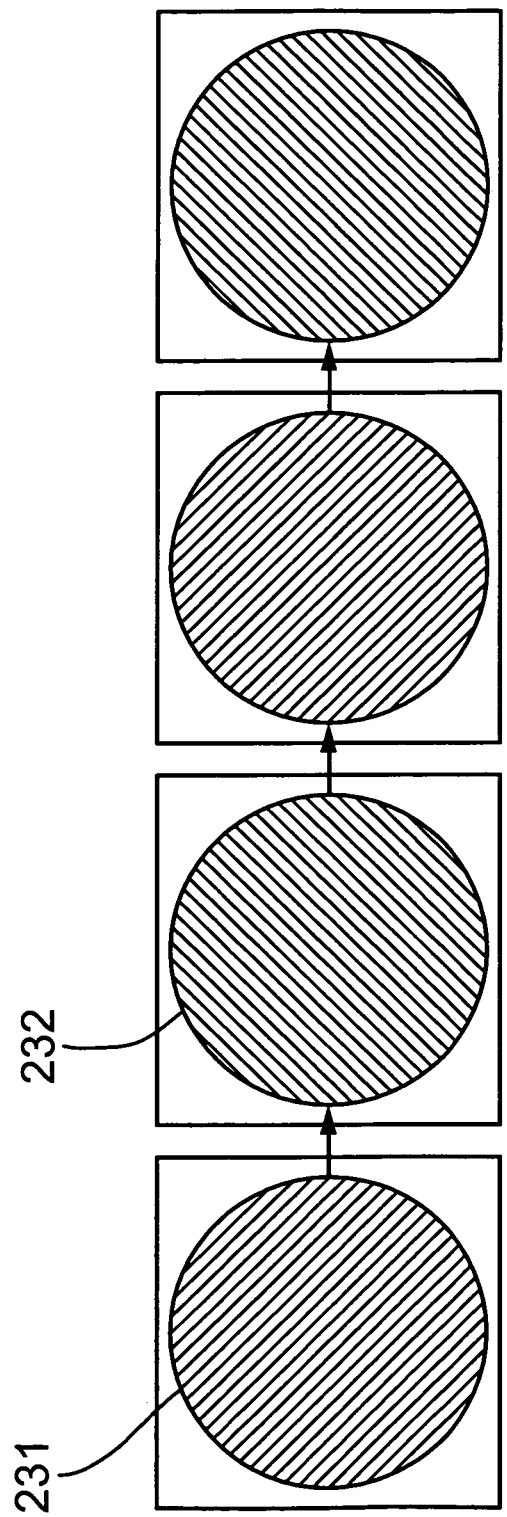
FIG. 22 is a schematic of a display which transitions over time from one image to another, co-registered image.

Alternatively, displaying the first image 231 and second image 232 at the same position on the screen as separate layers and varying the transparency of the layer in the foreground can effectively provide a means for combining the images. Alternatively, the order of the layers can be varied over time, such as by having the IVUS image in the foreground for one time interval and then transitioning to having the OCT image in the foreground for a subsequent time interval, as seen in FIG. 22.

Figure 23A:
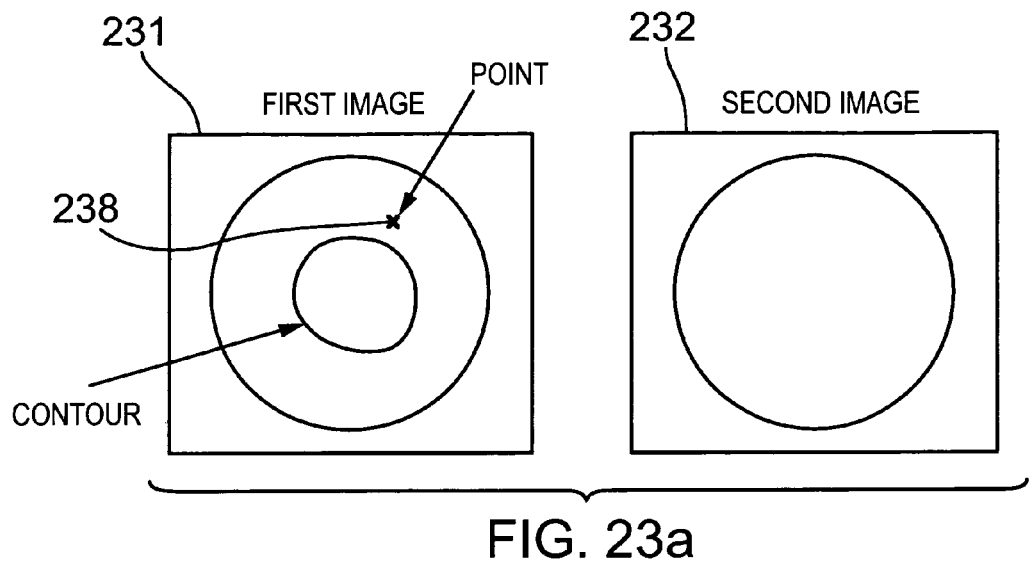
FIGS. 23a and 23b demonstrate how a feature in a first image can be mapped onto a feature in another image that is co-registered with the first image.
Figure 23B:
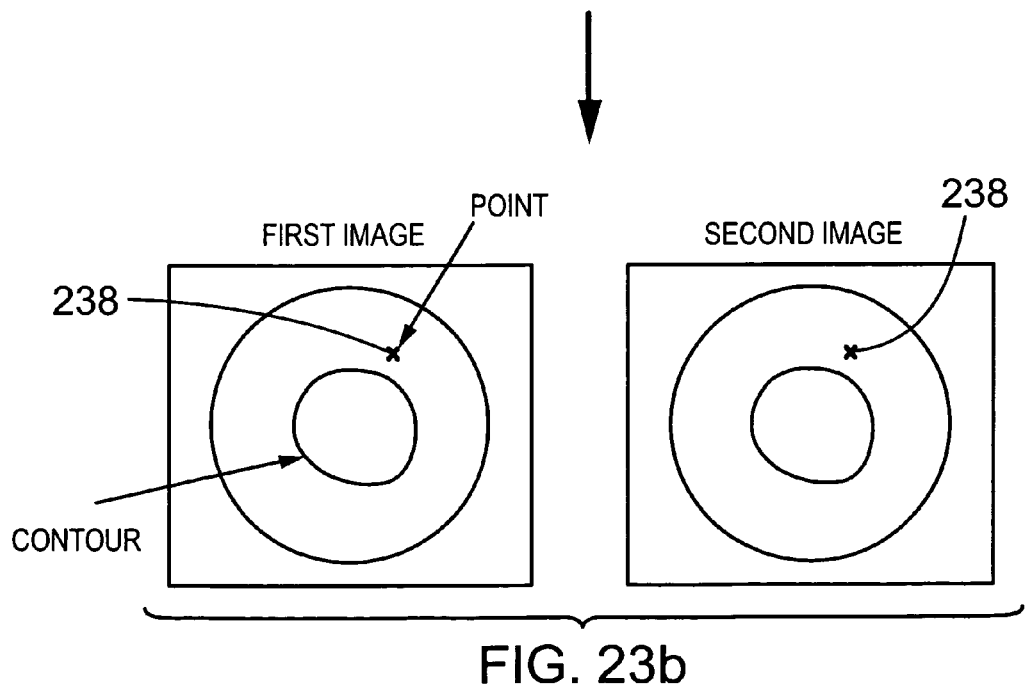

It is an object of the present invention to be able to identify certain features of interest in a first image 231 and transfer knowledge of that feature (such as its position, shape, signal properties or composition) to a second image 232 that is accurately co-registered with the first image 231. Geometric features include specific points, contours or 2D regions in an image. As seen in FIG. 23*a*, a user can identify a point 238, contour or region in a first image 231 manually, through the user interface of the imaging system (such as with a mouse or keyboard) and have that geometric point 238 appear in a second image 232 co-registered with the first image 231 as in FIG. 23*b*. The availability of one or more other images that are accurately co-registered with the first image makes it possible to superimpose any or all of the geometric features from the first image to any of the other images.

By way of example, the user might identify the inner boundary of a blood vessel or the trailing edge of a fibrous cap in an OCT image. FIG. 24*a* shows the contour representing the inner border 241 identified in a schematic representation of an OCT image (the first image). Similarly, the outer boundary 242 of the vessel wall (usually defined by the external elastic lamina) can be identified in an IVUS image (the second image). The contours representing the inner boundary 241 of the blood vessel or the trailing edge of the fibrous cap can then be superimposed onto the corresponding IVUS image. Similarly, the outer boundary 242 of the vessel wall (usually defined by the external elastic lamina) can be identified in an IVUS image. The contour representing the outer boundary as assessed in the IVUS image can be superimposed onto the OCT image. FIG. 24*b* shows the inner and outer boundaries on both the first and second images.

While the inner boundary of the blood vessel is readily identified on most IVUS images, the OCT generated contour would be more accurate in most circumstances. Furthermore, OCT is thought to be much better for identifying the fibrous cap of a plaque, in part due to its higher resolution. However, IVUS can see much further into most vascular tissues and can provide a better assessment of the outer vessel wall.

A geometric feature can include features observed in 3D data sets, such as surfaces or volumes. A surface or volume observed in a 3D imaging dataset can be superimposed into another 3D imaging dataset if the two imaging datasets are accurately registered.

The geometric features of interest need not be manually identified. It is possible that features in an imaging dataset can be identified by automated or semi-automated means to minimize user intervention. For example, there are several border detection methods cited in the literature on IVUS (e.g. Klingensmith, IEEE Transactions on Medical Imaging, 2000; 19:652-662). Automated border detection methods analyze an image to identify a contour of some pre-determined significance. Semi-automated methods are similar, but require some user intervention to either provide a starting point for the border detection algorithm or to refine the results produced the algorithm.

Other feature detection algorithms can be conceived of to identify features other than a border. For example, a hyperintense/bright region in an ultrasound image followed a dark region in the same direction of the imaging beam is often referred to as "shadowing" and occurs most commonly when the area being imaged includes either calcium (such as from advanced atherosclerosis or malignant processes) or metal (such as from stents or other implants). Similarly, a highly intense region in an OCT image of a blood vessel, followed by a rapid but continuous attenuation of the signal acquired along the same imaging path is suggestive of necrotic material in the vessel wall. It is possible to detect such regions algorithmically and identify them in their respective images. Once such features are identified in their respective images, their position and shape can be superimposed into other images that are accurately co-registered.

In certain embodiments of the present invention, it will be desirable to do some adjustment to one or more of the images to further improve the co-registration. While many of the embodiments of the present invention improve the precision of acquiring imaging data with one or more imaging methods, there may be some advantage to further adjusting the images to improve the accuracy of the co-registration process. For example, ultrasound images are generated assuming a constant speed of sound through all tissues, while OCT assumes a constant speed of light through all tissues.

In reality however, there are small changes in these speeds depending on the composition of the tissue in which each of the imaging energies propagate. Therefore, prior to completing the co-registration process for one or more images, it may be desirable to morph or warp one or more of the images by identifying certain features in the two or more images that are to be co-registered and using those features to guide the morphing process. Any point, contour or other feature identified in all of the images to be co-registered can be used to drive the morphing process. An ultrasound image is most commonly formed by displaying a grayscale representation of the intensity of the ultrasound signal reflected back from the approximate anatomic location that corresponds to each pixel in the image. Similarly, an OCT image is most commonly formed by displaying a grayscale representation of the intensity of the light reflected back from the approximate anatomic location that corresponds to each pixel in the image.

Aside from the intensity information at each location in either an ultrasound or OCT image, there are several other features from ultrasound or OCT images that can be very helpful for analysis derived from combined imaging.

The display of an image derived from ultrasound signals based on a feature other than then intensity of a sample in the image is well known in the art. Nair et al (Circulation 2002; 106(17):2200-2206 and U.S. Pat. No. 6,200,268) published results of an algorithm that measures several parameters of an ultrasound signal in discrete regions of IVUS images of blood vessels. Each region was also assigned a tissue category based on histological analysis of the vessel. The ultrasound derived parameters and the histological classification of each region were input into a pattern recognition engine to generate an algorithm that is subsequently applied in an attempt to classify tissue in vivo based on its many ultrasound signal properties. Some of the properties used for analysis include frequency domain parameters over a defined range of frequencies such as maximum power, frequency of maximum power, minimum power, frequency of minimum power, slope, y-intercept, mid-band fit and integrated backscatter. The image generated comprises a topographical map of the vessel cross-section and a discrete number of colors, with each color representing a single tissue category. Wilson et al demonstrated the use of measuring the frequency domain attenuation of an ultrasound signal in regions of an IVUS images and overlaying a color map of the attenuation slope onto the conventional IVUS image to identify areas thought to correspond to specific pathological types.

Similarly, features of interest can be measured or identified in optical images in order to generate images other than intensity-based images. Parameters or other features that can be used to generate such images include attenuation, polarization sensitivity, detected edges, spectroscopic information and others.

As a result of the high degree of accuracy of co-registration enabled by the present invention, it is possible to generate images based on features or signal properties measured with more than one imaging modality. For example, a composite image can be made using an inner border 245 identified by OCT, an outer border 246 identified by IVUS and a color map of the most likely tissue components within the vessel wall using a pattern recognition system that combines optical signal properties with acoustic signal properties within focal regions of the imaging datasets to generate a composite image that will improve the ability to identify important components within the vessel wall, such as calcified, fibrous, atheromatous, thrombotic, metallic and non-diseased regions.

Figure 25A:
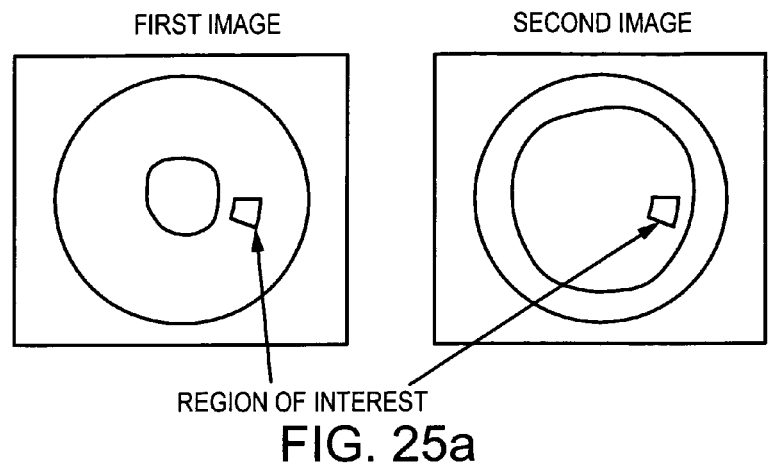
FIGS. 25a and 25b provide a schematic for how a composite image can be constructed from two (2) or more co-registered imaging datasets.
Figure 25B:
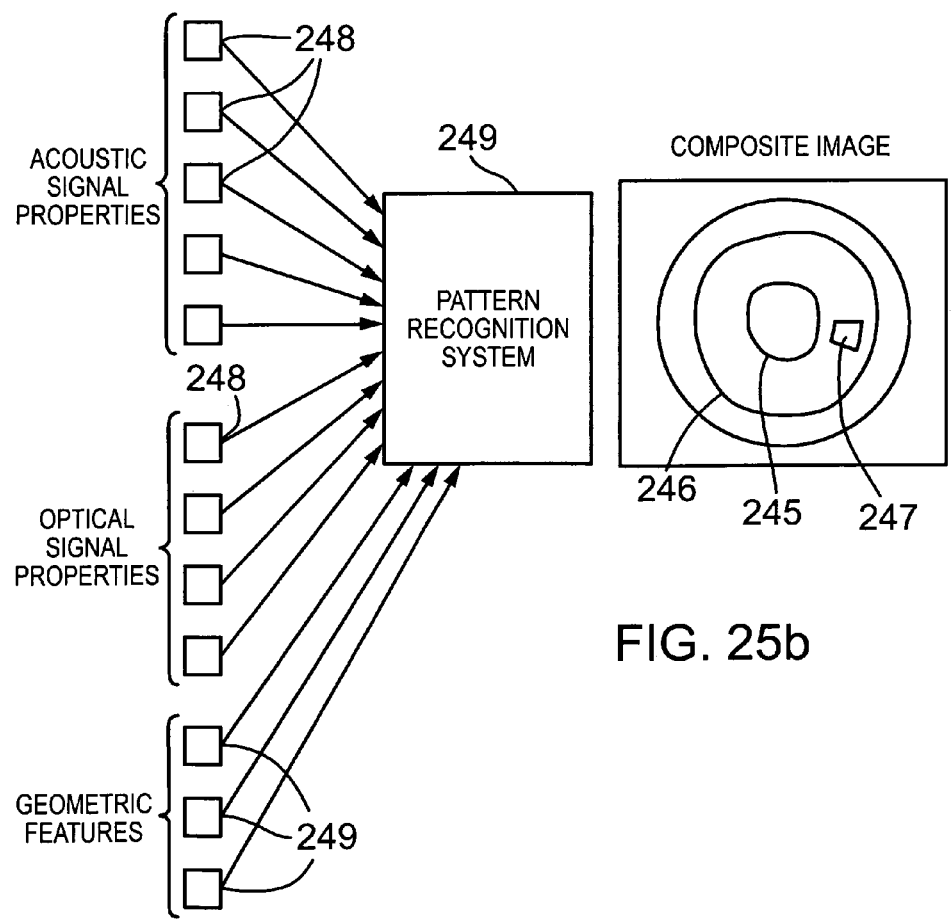

FIG. 25a shows a schematic representation of an inner border 245 identified by OCT, an outer border 246 identified in the second image by IVUS and a region of interest 247 used for analysis of the OCT and ultrasound signal properties. As shown in FIG. 25b, the signal properties 248 from the more than one modalities of imaging in the co-registered region of interest are used to generate an assessment of the composition of one or more pixels in the composite image that correspond to the region of interest analyzed. The assessment may be formed by a pattern recognition system 249 trained using methods known in the art. The geometric features 249 identified in the co-registered images are also optionally included in the composite image. The process of assessing the composition of a region of interest can be repeated several times over for different regions of interest to generate a composite image.

In addition, the software and image processing algorithms that enables such analysis of the combined imaging means need not be on the acquisition station. Once the imaging data is acquired, the imaging data can be transferred to allow analysis to occur offline on a separate set of one or more processing units.

The combined IVUS/OCT scanning devices disclosed herein may include a rotary encoder. Further details of optical encoders which may used with the combined IVUS/OCT scanning devices are disclosed in copending application Ser.

No. 12/020,207, filed concurrently herewith, entitled MEDICAL IMAGING DEVICE WITH ROTARY ENCODER, which is incorporated herein by reference in its entirety.

Briefly, referring to FIGS. 26a to 26c, the imaging probes may incorporate an encoder which is designed be used with an elongate imaging probe that uses a rotary shaft such as the imaging conduit 34 as part of its scanning mechanism, its use can be generalized for use with any device that makes use of a long, flexible cable used for transmission of torque where non-uniform rotational distortion may occur and an accurate estimation of rotary motion is required. In particular, it is most suited for use with flexible torque transmission systems where the outer diameter of the torque cable is relatively small (e.g. less than 4 mm) and long (e.g. longer than 5 cm) such that conventional rotary encoding systems would not provide the desired angular resolution or be adequately compact for the intended use.

FIG. 26a demonstrates a longitudinal cross-section of the proximal and distal ends of an elongate imaging device 450 with a torque transmission shaft 451, mechanically coupled to a torque source 452. The torque source 452 can be a motor, a handle that is manually turned by the operator or any other such device. The torque transmission shaft 452 transmits torque to the functional end 454 of the device, which can be an energy delivery device, a needle, an atherectomy head or any of several other implements. In FIG. 26c, the wall of an external sheath 453 is shown to surround the transmission shaft and is shown to enclose the functional end of the device although embodiments where the external sheath is open or has openings near the functional end are possible. An optical fiber 455 is shown to be included as part of the external sheath 453 for the purposes of enabling either the emitting light, detecting light or both to travel to or from the encoding interface 104 that is remote to the proximal end of the transmission sheath. In FIG. 26a the cylindrical encoding interface body 180 in this case is attached to a rotating portion of the device while the fiber is relatively stationary. The optical fiber 455 may be included as part of the extrusion of the external sheath 453, as shown, or may be added to the inner or outer surface of the sheath and anchored to the sheath 453 by methods well known in the art, such as bonding or surrounding the fiber and sheath with an additional layer of heat shrinkable material. The optical fiber 455 is terminated with any necessary distal optics 115, such as an optical spacer, lens and/or deflecting mechanism 172 (such as a prism or mirror) to direct light towards the encoding interface 104. The encoding interface 104 in FIG. 26a may be similar to that on the cylindrical encoding interface body disclosed in copending application Ser. No. 11/020,207, filed concurrently herewith, entitled MEDICAL IMAGING DEVICE WITH ROTARY ENCODER The encoding interface 104 in FIG. 26b is similar to that on the cylindrical encoding interface body in the above mentioned copending application. As the encoding optical circuit used in the embodiments of FIGS. 14a and 14b are not mounted onto or directly coupled with the torque transmission shaft, there is no need for an optical rotary joint along the optical encoding circuit.

FIG. 26c shows a cross-sectional image of a representative cross-section through the device 450 in FIG. 26b through line 14c-14c. One or more fiber optics 455 for the encoding system may be incorporated with the external sheath 453.

Thus the rotary encoder embodiments disclosed in copending application Ser. No. 12/020,207 filed concurrently herewith, entitled MEDICAL IMAGING DEVICE WITH ROTARY ENCODER , mentioned above can be incorporated into an imaging probe 12 by substituting the functional end of any of the embodiments in FIGS. 26a to 26d for an imaging assembly 30 and substituting the torque transmission shaft 451 for an imaging conduit 34 suitable for carrying either electrical or optical signals.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An imaging probe, comprising:
a hollow shaft;
an imaging conduit at least partially residing within said hollow shaft, said imaging conduit including a fiber optic and an electrical conductor, wherein said imaging conduit is connectable, at a proximal end thereof, to a hardware image processing system, a source of light, and an ultrasound signal generator;
an imaging assembly mechanically coupled to said imaging conduit at a location remote from a proximal portion of said imaging conduit, said imaging assembly including:
an optical emitter/collector including an optical deflecting element, wherein said optical deflecting element is in optical communication with a distal end of said fiber optic for directing light imaging energy out of said distal end of said fiber optic and directing reflected light energy signals into said distal end of said fiber optic; and
an ultrasound transducer for emitting ultrasound imaging energy and receiving reflected ultrasound imaging energy signals, said ultrasound transducer comprising an acoustic substrate and a backing, wherein said ultrasound transducer is connected to said electrical conductor, and wherein at least a portion of said optical deflecting element resides within said backing;
wherein said imaging assembly is configured to deliver the light imaging energy from said optical emitter/collector and the ultrasound imaging energy from said ultrasound transducer out of said hollow shaft; and
wherein said ultrasound transducer and said optical deflecting element are positioned and oriented relative to each other to enable co-registration of the reflected light energy signals and the reflected ultrasound imaging energy signals during scanning of a region of interest.

2. The imaging probe according to claim 1 wherein said imaging conduit is connectable to a drive mechanism for imparting motion to said imaging conduit.

3. The imaging probe according to claim 2 wherein said imaging conduit is rotatable.

4. The imaging probe according to claim 2 further comprising said drive mechanism, wherein said drive mechanism is configured for providing reciprocating translational movement of said imaging conduit.

5. The imaging probe according to claim 3 wherein said optical deflecting element and said ultrasound transducer are positioned and oriented relative to each other so that the reflected light energy signals and reflected ultrasound imaging energy signals are received from the same direction.

6. The imaging probe according to claim 3 wherein said optical deflecting element and said ultrasound transducer are positioned and oriented relative to each other to enable imaging of the region of interest with a time delay between obtaining the reflected ultrasound imaging energy signals and the reflected light energy signals, where the path scanned by a first beam of imaging energy is followed in a predominant manner by a second beam of imaging energy, where the first beam of imaging energy is one of a beam of light imaging energy and a beam of ultrasound imaging energy, and where the second beam of imaging energy is the other of the beam of light imaging energy and the beam of ultrasound imaging energy, where said predominant manner is such that during a delay interval starting at an initial time point a beam axis of the second beam of imaging energy does not align itself further from an initial axis of the first beam of imaging energy, wherein the delay interval ends when the beam axis of the second beam of imaging energy is aligned with said initial axis.

7. The imaging probe according to claim 3 wherein said optical emitter/collector includes an optical focusing element for focusing light emitted from said distal end of said fiber optic to the region of interest being imaged and for collecting light reflected therefrom.

8. The imaging probe according to claim 7 wherein the light imaging energy is used to enable imaging by optical coherence tomography.

9. The imaging probe according to claim 7 wherein said ultrasound transducer and said optical emitter/collector are positioned and oriented relative to each other such that when rotating said imaging conduit, a region imaged by said ultrasound transducer at a first point in time is imaged by said optical emitter/collector at a second point in time, and wherein said optical focusing element is positioned so that an outer surface thereof is closer to the region that is being imaged at the second point in time than a primary emitting surface of said ultrasound transducer at the first point in time.

10. The imaging probe according to claim 3 wherein said ultrasound transducer has a surface from which the ultrasound imaging energy is emitted, and wherein said ultrasound transducer has an optically transmissive channel located therein and wherein said optical deflecting element resides along said optically transmissive channel to transmit the light imaging energy via said optically transmissive channel through said surface such that the light imaging energy is collinear with the ultrasound imaging energy.

11. The imaging probe according to claim 3 wherein said ultrasound transducer has a surface from which ultrasound signals are emitted, and wherein said optical deflecting element is mounted with respect to said ultrasound transducer to emit light at a pre-selected angle with respect to the direction in which the ultrasound imaging energy is emitted such that the ultrasound imaging energy and the light imaging energy image the region of interest at different times.

12. The imaging probe according to claim 11 wherein said pre-selected angle is selected from the group consisting of 90 degrees, 135 degrees and 180 degrees.

13. The imaging probe according to claim 3 wherein said optical emitter/collector is a first optical emitter/collector, said imaging assembly including a second optical emitter/collector configured to emit light at a pre-selected angle with respect to the first optical emitter/collector, so that light imaging energy emitted by the first optical emitter/collector and light imaging energy emitted by said second optical emitter/collector scan the region of interest.

14. The imaging probe according to claim 13 wherein at least a portion of said second optical emitter/collector resides within said backing.

15. The imaging probe according to claim 3 wherein said imaging assembly includes a reflective member mounted to reflect the light imaging energy from said optical emitter/collector and ultrasound signals from said ultrasound transducer, and wherein said reflective member is a movable member for delivering an energy beam along an energy beam path from said movable member out of said hollow shaft at a variable imaging angle with respect to a rotational axis of said imaging assembly, wherein said movable member is mounted so that the variable imaging angle is varied by adjusting an angular velocity of said imaging assembly about said rotational axis.

16. The imaging probe according to claim 15 wherein said reflective member comprises an acoustically reflective surface and an optically reflective surface, wherein said acoustically reflective surface and said optically reflective surface are provided in separate layers.

17. The imaging probe according to claim 16 wherein said acoustically reflective surface is contoured to focus the ultrasound imaging energy.

18. The imaging probe according to claim 16 wherein said optically reflective surface is acoustically transparent.

19. The imaging probe according to claim 15 wherein said movable member is pivotally mounted in said imaging assembly along a pivot axis perpendicular to said rotational axis of said imaging assembly.

20. The imaging probe according to claim 3 wherein the light imaging energy is visible light.

21. The imaging probe according to claim 3 wherein the light imaging energy is infrared light.

22. The imaging probe according to claim 3 further comprising a rotary encoder mechanism coupled to said imaging assembly for detecting rotational motion of said imaging assembly.

23. The imaging probe according to claim 3 wherein said optical emitter/collector and said ultrasound transducer are positioned and oriented relative to each other so that the ultrasound imaging energy and the light imaging energy are transmitted in a collinear direction from said optical emitter/collector and said ultrasound transducer.

24. The imaging probe according to claim 3 wherein said optical emitter/collector and said ultrasound transducer are positioned and oriented relative to each other such that the space occupied by an acoustic beam emitted from said ultrasound transducer overlaps the space occupied by an optical beam emitted from said optical emitter/collector and wherein the orientation of said optical beam from said optical emitter/collector is parallel to the orientation of said acoustic beam emitted from said ultrasound transducer.

25. The imaging probe according to claim 3 further comprising said hardware image processing system, wherein said hardware image processing system is configured to process ultrasound images and optical images obtained from ultrasound imaging and optical imaging during scanning of the region of interest and to co-register the ultrasound images and optical images and to display co-registered images.

26. The imaging probe according to claim 3 wherein at least a portion of said optical deflecting element is embedded within said backing.

27. The imaging probe according to claim 3 wherein one or more optical elements of said optical emitter/collector extend beyond an outer surface of said ultrasound transducer.

28. The imaging probe according to claim 3 wherein said imaging assembly is configured such that the light imaging energy delivered from said optical emitter/collector and the ultrasound imaging energy emitted from said ultrasound transducer propagate without further reflection prior to reaching an inner surface of said hollow shaft.

29. The imaging probe according to claim 3 wherein said imaging assembly is configured such that the light imaging energy delivered from said optical emitter/collector and the ultrasound imaging energy emitted from said ultrasound transducer propagate without encountering an additional reflective element prior to reaching an inner surface of said hollow shaft.

30. The imaging probe according to claim 3 wherein said optical emitter/collector is configured to deliver the light imaging energy and wherein said ultrasound transducer is configured to emit the ultrasound imaging energy in a direction that is oriented away from a rotational axis of said imaging assembly.

31. The imaging probe according to claim 3 wherein an outer diameter of a distal portion of said hollow shaft in which the imaging assembly can reside is less than approximately 2 mm.

32. The imaging probe according to claim 3 wherein said optical emitter/collector and said ultrasound transducer are configured for side-viewing and wherein said optical emitter/collector and said ultrasound transducer are tilted for reducing reflections from said hollow shaft.

33. An imaging probe, comprising:
a hollow shaft;
an imaging conduit at least partially residing within said hollow shaft, said imaging conduit including a fiber optic and an electrical conductor, wherein said imaging conduit is connectable, at a proximal end thereof, to a hardware image processing system, a source of light, and an ultrasound signal generator;
an imaging assembly mechanically coupled to said imaging conduit at a location remote from a proximal portion of said imaging conduit, said imaging assembly including:
an optical emitter/collector including an optical deflecting element, wherein said optical deflecting element is in optical communication with a distal end of said fiber optic for directing light imaging energy out of said distal end of said fiber optic and directing reflected light energy signals into said distal end of said fiber optic; and
an ultrasound transducer for emitting ultrasound imaging energy and receiving reflected ultrasound imaging energy signals, said ultrasound transducer including an acoustic substrate and a backing, wherein said ultrasound transducer is connected to said electrical conductor;
wherein said ultrasound transducer includes an optically transmissive channel having a first portion and a second portion, wherein said first portion resides at least partially within said backing, and wherein said second portion is in optical communication with said first portion, said second portion extending through said acoustic substrate of said ultrasound transducer and through an emitting surface of said ultrasound transducer, and wherein said optical deflecting element resides along said optically transmissive channel for deflecting an optical beam between said first portion and said second portion;
wherein said imaging assembly is configured to deliver the light imaging energy from said optical emitter/collector and the ultrasound imaging energy from said ultrasound transducer out of said hollow shaft; and
wherein said ultrasound transducer and said optical deflecting element are positioned and oriented relative to each other to enable co-registration of the reflected light energy signals and the reflected ultrasound imaging energy signals during scanning of a region of interest.

34. The imaging probe according to claim 33 wherein at least a portion of said optically transmissive channel includes an acoustic damping layer.

35. The imaging probe according to claim 34 wherein said acoustic damping layer includes a compliant material for reducing the transmission of stresses generated by said acoustic substrate to optical elements residing within said optically transmissive channel.

36. The imaging probe according to claim 33 wherein at least a portion of said optically transmissive channel includes an electrically insulating layer.

37. The imaging probe according to claim 33 further comprising an optical focusing element, wherein at least a portion of said optical focusing element resides within said optically transmissive channel.

38. The imaging probe according to claim 37 wherein said optical focusing element resides within said acoustic substrate within said second portion of said optically transmissive channel.

39. The imaging probe according to claim 38 wherein said optical focusing element extends beyond an outer surface of said ultrasound transducer.

40. The imaging probe according to claim 37 wherein said optical deflecting element is a prism having a path length suitable for acting as an optical spacer for said optical focusing element.

41. The imaging probe according to claim 37 wherein said optically transmissive channel includes an optical spacer residing therein, wherein said optical spacer is located along an optical beam path between said distal end of said fiber optic and said optical focusing element.

42. The imaging probe according to claim 37 wherein said optical focusing element resides within said second portion of said optically transmissive channel.

43. The imaging probe according to claim 33 wherein a distal portion of said second portion of said optically transmissive channel includes an optically transmissive window.

44. The imaging probe according to claim 43 wherein a region within said optically transmissive channel that is unoccupied by an optical component is filled with a gas or fluid.

45. The imaging probe according to claim 33 wherein a distal portion of said fiber optic is embedded within said first portion of said optically transmissive channel.

46. The imaging probe according to claim 33 wherein at least a portion of the backing is interposed between said first portion of said optically transmissive channel and said acoustic substrate.

47. The imaging probe according to claim 33 wherein at least a portion of said backing is provided behind said first portion of said optically transmissive channel, on a side opposite to that of said acoustic substrate.

48. The imaging probe according to claim 33 wherein said first portion of said optically transmissive channel is adjacent to said acoustic substrate.

49. An imaging probe, comprising:
a hollow shaft;
an imaging conduit at least partially residing within said hollow shaft, said imaging conduit including a fiber optic and an electrical conductor, wherein said imaging conduit is connectable, at a proximal end thereof, to a hardware image processing system, a source of light, and an ultrasound signal generator;

an imaging assembly mechanically coupled to said imaging conduit at a location remote from a proximal portion of said imaging conduit, said imaging assembly including:
an optical emitter/collector including an optical deflecting element, wherein said optical deflecting element is in optical communication with a distal end of said fiber optic for directing light imaging energy out of said distal end of said fiber optic and directing reflected light energy signals into said distal end of said fiber optic;
an ultrasound transducer for emitting ultrasound imaging energy and receiving reflected ultrasound imaging energy signals, wherein said ultrasound transducer is connected to said electrical conductor,
said ultrasound transducer including an acoustic substrate and a backing, wherein at least a portion of said optical emitter/collector resides within a channel provided in said backing, and further including a deflecting feature configured to deflect ultrasound energy that would otherwise be reflected towards said acoustic substrate by said portion of said optical emitter/collector that resides within said channel;
wherein said imaging assembly is configured to deliver the light imaging energy from said optical emitter/collector and the ultrasound imaging energy from said ultrasound transducer out of said hollow shaft;
wherein said ultrasound transducer and said optical deflecting element are positioned and oriented relative to each other to enable co-registration of the reflected light energy signals and the reflected ultrasound imaging energy signals during scanning of a region of interest.

50. The imaging probe according to claim 49 wherein an external surface of said channel is shaped to deflect ultrasound energy in one or more directions that are not oriented towards said acoustic substrate.

51. The imaging probe according to claim 49 wherein said deflecting feature is an acoustically reflective element that is configured to deflect ultrasound energy in one or more directions that are not incident upon said acoustic substrate.

52. The imaging probe according to claim 51 wherein said acoustically reflective element is positioned adjacent to at least a portion of said channel.

* * * * *